(12) United States Patent
Lieberman et al.

(10) Patent No.: US 8,168,601 B2
(45) Date of Patent: May 1, 2012

(54) METHOD OF DELIVERING RNA INTERFERENCE AND USES THEREOF

(75) Inventors: Judy Lieberman, Brookline, MA (US); Erwei Song, Guangzhou (CN)

(73) Assignee: Immune Disease Institute, Inc., Boston, MA (US)

( * ) Notice: Subject to any disclaimer, the term of this patent is extended or adjusted under 35 U.S.C. 154(b) by 0 days.

(21) Appl. No.: 11/659,386

(22) PCT Filed: Aug. 15, 2005

(86) PCT No.: PCT/US2005/029111
§ 371 (c)(1),
(2), (4) Date: May 9, 2007

(87) PCT Pub. No.: WO2006/023491
PCT Pub. Date: Mar. 2, 2006

(65) Prior Publication Data
US 2008/0153737 A1    Jun. 26, 2008

Related U.S. Application Data

(60) Provisional application No. 60/601,950, filed on Aug. 16, 2004.

(51) Int. Cl.
*A61K 48/00* (2006.01)
*C07H 21/02* (2006.01)
*C07H 21/04* (2006.01)
*C07K 16/00* (2006.01)

(52) U.S. Cl. ...... 514/44; 536/23.1; 536/24.5; 530/387.1

(58) Field of Classification Search .................. None
See application file for complete search history.

(56) References Cited

U.S. PATENT DOCUMENTS

| | | | |
|---|---|---|---|
| 5,177,196 A | 1/1993 | Meyer, Jr. et al. | |
| 5,288,854 A | 2/1994 | Diamond et al. | |
| 5,734,039 A * | 3/1998 | Calabretta et al. | ........... 536/24.5 |
| 5,877,295 A | 3/1999 | Diamond et al. | |
| 6,030,954 A | 2/2000 | Wu et al. | |
| 6,667,318 B2 | 12/2003 | Burdick et al. | |
| 7,160,541 B2 | 1/2007 | Springer et al. | |
| 7,241,869 B2 | 7/2007 | Springer et al. | |
| 7,544,374 B2 | 6/2009 | Margalit et al. | |
| 7,674,604 B2 | 3/2010 | Springer et al. | |
| 2002/0132990 A1 | 9/2002 | Huston | |
| 2004/0023902 A1 | 2/2004 | Marasco et al. | |
| 2004/0037775 A1 | 2/2004 | Siahaan | |
| 2004/0204377 A1 * | 10/2004 | Rana ................. | 514/44 |

FOREIGN PATENT DOCUMENTS

| WO | WO 95/22618 | 8/1995 |
|---|---|---|
| WO | 2004039957 | 5/2004 |
| WO | 2005002516 | 1/2005 |
| WO | 2005079515 | 9/2005 |
| WO | 2006017195 | 2/2006 |
| WO | 2006023491 | 3/2006 |
| WO | 2006133099 | 12/2006 |

OTHER PUBLICATIONS

Simeoni et al., Insight into the mechanism of the peptide-based gene delivery system MPG: implications for delivery of siRNA into mammalian cells, 2003, Nucleic Acids Research, vol. 31, No. 11, pp. 2717-2724.*
Novina et al., siRNA-directed inhibition of HIV-1 infection, 2002, Nature Medicine, vol. 8, No. 7, pp. 681-686.*
Chen et al., Design of a genetic immunotoxin to eliminate toxin immunogenicity, 1995, Gene Ther., 2(2), pp. 116-123.*
Weiss, HIV-1 gp41: mediator of fusion and target for inhibition, 2003, AIDS Rev., 5(4), pp. 214-221.*
Sorensen et al., Gene Silencing by Systemic Delivery of Synthetic siRNAs in Adult Mice, 2003, J. Mol. Biol., 327, 761-766.*
Astriab-Fisher, et al. "Conjugates of Antisense Oligonucleotides with the Tat and Antennapedia Cell-Penetrating Peptides: Effects on Cellular Uptake, Binding to Target Sequences, and Biologic Actions" pp. 744-754, 2002.
Song, et al. "Antibody mediated in vivo delivery of small interfering RNAs via cell-surface receptors" pp. 709-717, 2005.
Cutrona, et al. "Effects in live cells of a c-myc anti-gene PNA linked to a nuclear localization signal" pp. 300-303, 2000.
Zhang, Y. et al., Clinical Cancer Research, 10:3667-3677 (2004). "Intravenous RNA interference gene therapy targeting the human epidermal growth factor receptor prolongs survival in intracranial brain cancer."
Anderson et al., Pharm Res 20(10):1523-1532, 2003.
Baulcombe, Science, 297; 2002-2003, 2002.
Beglova et al., Nat. Struct. Biol. 9:282-289, 2002.
Carman et al., Curr. Opin. Cell Biol. 15:547-556, 2003.
Chirathaworn et al., J. Immunol. 166: 5530-5537, 2002.
Coffey et al., J. Pharmacol. Exp. Ther. 310(3): 96-904, 2004.
Constanin et al., Immunity 13:758-769, 2000.
deFougerolles, "Integrins in Immune Inflammatory Disease," Chapter 12, I Domains in Integrins, Gullberg, 2003.
Dustin et al., Nat. Immunol. 5:363-372, 2004.
Fabbri et al., Mol. Biol. Cell 16(12):5793-5803, 2005.
Gamper et al., Nucleic Acids Res. 21:145-150, 1993.
Goffinet et al., FASEB J. 20:500-502, 2006.
Guccione et al., IEEE Eng. Med. Biol. Mag 23(5):50-56, 2004.
Hargreaves et al., Trends Mol Med 10:130-135, 2004.
Haskard et al., J. Immunol. 137:2901-2906, 1986.
Hood et al., Science 296 (5577): 2404-2407, 2002.
Huang et al., J. Leukocyte Biol. 80:905-914, 2006.

(Continued)

*Primary Examiner* — Amy Bowman
(74) *Attorney, Agent, or Firm* — Nixon Peabody LLP

(57) ABSTRACT

The invention provides a method of RNA interference, which comprises contacting the cell with a fusion protein-double stranded RNA complex, the complex comprising the double stranded RNA segment containing a double stranded RNA of interest and a fusion protein, the fusion protein comprising (1) a targeting moiety, which will specifically binds to a site on a target cell, and (2) a binding moiety, which will bind to the double stranded RNA, wherein the double stranded RNA segment initiates RNA interference in the cell.

15 Claims, 30 Drawing Sheets

OTHER PUBLICATIONS

Kim, Mol. Cells 19:1-15, 2005.
Kinashi et al., Immunology 116(2):164-71, 2005.
Kinashi et al., Immunol. Lett. 93:1-5, 2004.
Krawetz et al. Genomics 5: 639-635, 1988.
Krutzfeldt et al. Nature 438 (7068):685-689, 2005.
Langerak et al., Blood 98(1):165-73, 2001.
Lu et al. J. Immunol. 166(9):5269-5637, 2001.
Ma et al., J. Biol Chem 277:10638-10641, 2002.
Marodon et al., Blood, 101:3416-3423, 2003.
Melikov et al., Cell Mol. Life Sci. 62:2739-2749, 2005.
Huang et al., J. of Biol. Chem. vol. 276. No. 8, Jul. 14, 2000, pp. 21514-21524.
Perez et al., Nat Immunol. 4:1083-1092, 2003.
Ratcliff et al., Science, 276:1558-1560, 1997.
Reed et al., Bioconjugate Chem 2:217-225, 1991.
Salas et al., Immunity, 20:393-406, 2004.
Shimaoka et al., Proc. Natl. Acad. Sci. USA 98:6009-6014, 2001.
Shimaoka et al., Cell 112:99-111, 2003.
Shimaoka et al., Immunity 19:391-402, 2003.
Shimaoka et al., Proc. Natl Acad Sci USA 103:13991-13996, 2006.
Smith et al., J. Cell Sci Epub, 2003.
Smith et al., J. Cell Biol. 170:141-151, 2005.
Song et al., Nature Medicine 9:347-351, 2003.
Sugamura K. et al, Nat. Rev. Immunol 4:420-431, 2004.
Tonneson et al., J. Clin Invest. 83(2):637-646, 1989.
Waterhouse et al., Nature 411:834-842, 2001.
Wolfraim, Immunol. Ther Exp (Warsz) 54:1-13, 2006.
Li et al., Cancer Gene Therapy, vol. 8, No. 8, 2001, pp. 555-565.
Lu et al., J. of Immunol., 173, 3972-3978, 2004.
Peer et al., Selective gene silencing in activated leukocytes by targeting siRNAs to the integrin lymphocyte function-associated antigen-1, PNAS, Mar. 6, 2007, vol. 104, No. 10, 4095-4100.
Vornlocher et al., Trends in Molecular Medicine, vol. 12, No. 1, Jan. 2006.
Wagner, et al., Biochemistry, vol. 87, pp. 3410-3414, 1990.
Xie, et al., PNAS, Oct. 26, 2004, vol. 101, No. 43, 15422-15427.

\* cited by examiner

SEQUENCE LISTING

```
<160> NUMBER OF SEQ ID NOS: 30

<210> SEQ ID NO 1
<211> LENGTH: 126
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 1
gcggccgcac gcagccagag ccggagcaga tattaccgcc agagacaaag aagtcgcaga      60
cgaaggaggc ggagctgcca gacacggagg agagccatga gatctcatca tcaccaccac    120
cattaa                                                               126

<210> SEQ ID NO 2
<211> LENGTH: 147
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 2
gcggccgcaa tggccaggta cagatgctgt cgcagccaga gccggagcag atattaccgc      60
cagagacaaa gaagtcgcag acgaaggagg cggagctgcc agacacggag gagagccatg    120
agatctcatc atcaccacca ccattaa                                        147

<210> SEQ ID NO 3
<211> LENGTH: 168
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 3
gcggccgcac gcagccagag ccggagcaga tattaccgcc agagacaaag aagtcgcaga      60
cgaaggaggc ggagctgcca gacacggagg agagccatga ggtgttgtcg ccccaggtac    120
agaccgagat gtagaagaca cagatctcat catcaccacc accattaa                 168
```

```
<210> SEQ ID NO 4
<211> LENGTH: 102
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 4
gcggccgcac gcagccagag ccggagcaga tattaccgcc agagacaaag aagtcgcaga      60
cgaaggaggc ggagcagatc tcatcatcac caccaccatt aa                       102

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 5
gcggccgccg gcggaggagg atctcatcat caccaccatt aa                        42

<210> SEQ ID NO 6
<211> LENGTH: 123
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 6
gcggccgcaa tggccaggta cagatgctgt cgcagccaga gccggagcag atattaccgc      60
cagagacaaa gaagtcgcag acgaaggagg cggagcagat ctcatcatca ccaccaccat    120
taa                                                                  123

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      siRNA

<400> SEQUENCE: 7
gcuucggaac aagagacuct t                                               21

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      siRNA

<400> SEQUENCE: 8
uaagcguaag caguguuggt t                                               21

<210> SEQ ID NO 9
<211> LENGTH: 21
<212> TYPE: DNA
```

```
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      siRNA

<400> SEQUENCE: 9
ccaacacugc uuacgcuuat t                                                   21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      siRNA

<400> SEQUENCE: 10
uaagcguaag caguguuggt t                                                   21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      siRNA

<400> SEQUENCE: 11
aagaagcuug aauuaagcgt t                                                   21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      siRNA

<400> SEQUENCE: 12
cgcuuaauuc aagcuucuut t                                                   21

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 13
gaacaucauc auccaggac                                                      19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
                                           siRNA

<400> SEQUENCE: 14
guccuggaug augauguuc                                                    19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 15
acucgaacag cuucgaaac                                                    19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 16
guuucgaagc uguucgagu                                                    19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 17
cgaugaagcc cuggagugc                                                    19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA

<400> SEQUENCE: 18
gcacuccagg gcuucaucg                                                    19

<210> SEQ ID NO 19
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic siRNA
<220> FEATURE:
<223> OTHER INFORMATION: Description of Artificial Sequence: Synthetic
      siRNA

<400> SEQUENCE: 19
acggaucuga cuacucacuc att                                               23

<210> SEQ ID NO 20
<211> LENGTH: 23
<212> TYPE: DNA
<213> ORGANISM: Artificial Sequence
<220> FEATURE:
```

```
<223> OTHER INFORMATION: Description of Combined DNA/RNA Molecule:
      Synthetic siRNA
<220> FEATURE:
<223> OTHER INFORMATION: Description of Artificial Sequence: Synthetic
      siRNA

<400> SEQUENCE: 20
ugagugagua gucagauccg utt                                          23

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttcaccacca tggagaaggc                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggcatggact gtggtcatga                                              20

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cccctggtgc tccatgag                                                18

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcctcctcag agtcgc                                                  16

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tttgcccaga ctcgagctcc tg                                           22

<210> SEQ ID NO 26
<211> LENGTH: 22
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 26
gggtgcaggt tcgggattca ac                                              22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggaggttgca gtgccaacga ag                                              22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tggaagggag gcagggcata ac                                              22

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctggagcagc tgaatggaaa g                                               21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cttgaagtcc gccctgtagg t                                               21
```

METHOD OF DELIVERING RNA INTERFERENCE AND USES THEREOF

CROSS-REFERENCE TO RELATED APPLICATIONS

This application is a 371 National Phase Entry Application of co-pending International Application PCT/US2005/029111, filed Aug. 15, 2005, which designated the U.S. and claims the benefit under 35 U.S.C. §119(e) of U.S. Provisional Application No. 60/601,950, filed Aug. 16, 2004, the entire contents of which are incorporated herein by reference.

GOVERNMENT SUPPORT

This invention was supported by National Institutes of Health (NIH) Grant No. AI056900; the government of the United States has certain rights thereto.

FIELD OF THE INVENTION

The present invention is directed to methods of RNA interference, particularly the delivery of small interfering RNAs (siRNAs) into target cells.

BACKGROUND OF THE INVENTION

Much attention has been paid recently to RNA interference (RNAi), a technique in which exogenous, double-stranded RNAs (dsRNAs) are introduced into a cell to specifically destroy a particular mRNA or block its expression, thereby diminishing or abolishing gene expression (A. Fire et al., "Potent and specific genetic interference by double-stranded RNA in *Caenorhabditis elegans*," *Nature*, 391:806-11, 1998). Specific types of RNAs, such as small interfering RNAs (siRNAs) and micro interfering RNAs (miRNAs) have been shown to inhibit expression of a number of specific genes effectively and the technique has proven effective in *Drosophila, Caenorhabditis elegans*, plants, and recently, in mammalian cell cultures (S. M. Elbashir et al., "Duplexes of 21-nucleotide RNAs mediate RNA interference in cultured mammalian cells," *Nature*, 411:494-8, 2001). Because small interfering RNA molecules are directed to a specific target and thereby silence a specific gene, they have been suggested to be useful in treatment of diseases as well as for screening new pharmaceuticals and disease mechanisms for pharmaceutical target determination. However, while a number of applications, both therapeutic and screening methods, have been suggested, delivery of RNA interfering agents, including siRNAs and miRNAs, into cells has proven to be the bottleneck.

Currently known methods to deliver RNA interference into cells include chemical transfection using lipid-based, amine-based and polymer-based techniques, and combinations thereof (see, for example, products from Ambion Inc., Austin, Tex.; and Novagen, EMD Biosciences, Inc, an Affiliate of Merck KGaA, Darmstadt, Germany). Unfortunately, efficient transfer of RNA interfering agents, including siRNAs into primary cells by chemical transfection seems to be restricted to a few cell types (Ovcharenko D (2003) "Efficient delivery of siRNAs to human primary cells." Ambion TechNotes 10 (5): 15-16).

Other described ways to deliver siRNAs include expressing short hairpin RNA molecules from vectors, such as lentiviral constructs, and introducing siRNA molecules into cells using electroporation. However, feline FIV lentivirus vectors which are based on the feline immunodeficiency virus (FIV) retrovirus and the HIV lentivirus vector system, which is base on the human immunodeficiency virus (HIV), carry with them problems related to permanent integration. Electroporation is often a relatively harsh treatment and cannot generally be used to deliver siRNAs into cells in vivo.

An additional problem with all the traditional gene delivery methods discussed above for the use of delivering RNA interference is that they target all cells non-specifically. Therefore, it would be useful to develop gene delivery methods that could be targeted to specific cells thereby minimizing or avoiding potential side effects caused by delivery of RNA interference into non-target cells. Additionally, effective interference RNA delivery methods that could avoid viral vectors and could be used for both in vivo and in vitro delivery of RNA interference, including siRNA, would be desirable.

Moreover, several cell types have proven extremely difficult to transduce with siRNAs using traditional vectors, including viral vectors, liposomes and the like. Such cell types include immune system cells such as lymphocytes and dendritic cells, and stem cells.

Therefore, to utilize fully the potential in treatment and drug screening of the discovered RNA interference, including siRNAs, it is necessary to develop ways to deliver siRNAs into cells both in vitro and in vivo.

SUMMARY OF THE INVENTION

Accordingly, the present invention provides a novel method of targeted delivery both in vitro and in vivo of small interference RNAs into desired cells thus avoiding entry of the siRNA into other than intended target cells. Therefore, the method of the present invention allows treatment of specific cells with RNA interference limiting potential side effects of RNA interference caused by non-specific targeting of RNA interference. Moreover, by specific targeting, the amount of RNA interference administered into a subject in need of treatment can be minimized because the effect of the RNA interference is concentrated into the specific target cells. Specific target cells include, but are not limited to cancer cells, virus-infected cells and cells susceptible for a certain type of virus. Any cell type or group of cell types expressing unique cell surface molecules, such as proteins, carbohydrates or lipids, can be targeted using the method of the invention.

The methods of the present invention are based on the discovery, that a complex or a fusion molecule comprising a cell targeting moiety and an RNA interference binding moiety can be used to deliver RNA interference effectively into cells. We have shown, for example, that an antibody-protamine fusion protein when mixed with siRNA, binds siRNA and selectively delivers the siRNA into cells expressing an antigen recognized by the antibody, resulting in silencing of gene expression only in those cells that express the antigen.

Using the fusion protein comprising a cell targeting moiety and an siRNA binding moiety mixed or complexed with siRNA, we also demonstrated delivery of siRNA molecules to cells that are normally hard to transduce.

Additionally, we demonstrated that not only cells in culture but also cells in an organism can be transduced using this method and used therapeutically. We showed efficient delivery using both subcutaneous and intravenous delivery in vivo.

Accordingly, in one embodiment, the invention provides a method of RNA interference in a cell, comprising contacting the cell with a fusion protein-double stranded RNA complex, the complex comprising: (a) an RNA molecule comprising a double stranded RNA segment, wherein one of the strands is complementary and the other strand identical to an RNA interference target RNA; and (b) a fusion protein, comprising (1) a targeting moiety, which specifically binds to a site on a target cell, and (2) a binding moiety, which binds to the double stranded RNA segment, wherein the double stranded RNA segment initiates RNA interference in the cell. In one preferred embodiment, the double stranded RNA is an siRNA.

As indicated, the fusion protein used to deliver RNA interference according to the method of the invention consists of a targeting moiety and an siRNA binding moiety.

In one preferred embodiment, the targeting moiety is a ligand for a cell surface receptor present on the cell surface. In one embodiment, the cell surface receptor is CD4, CCR5 or CXCR4. For example, in one embodiment, the ligand is a CD4 receptor ligand, which can be used to specifically target CD4+ T cells. Because HIV infects specifically CD4+ T cells, siRNA molecules that silence expression of HIV genes can be selectively and effectively delivered into the cells using a CD4 receptor ligand targeting moiety. In a preferred embodiment, the ligand useful according to the present invention is F105. F105 can be used to direct siRNAs into HIV-infected cells.

The term "F105" as used herein and throughout the specification refers to a monoclonal antibody F105, identified in an HIV-infected individual, that binds to a discontinuous epitope on the HIV-1 gp120 envelope glycoprotein and blocks the binding of gp120 to the CD4 cell surface receptor. The sequence of the F105 is described in Marasco et al., J. Clin Invest 90: 1467-1478, 1992.

In another preferred embodiment, the target moiety is an antibody. For instance, the target moiety is an antibody recognizing a viral envelope protein, a cellular receptor, an extracellular domain of an activated receptor, a cell surface carbohydrate or a cell surface lipid. The antibody is preferably a single chain antibody, a Fab portion of an antibody or a (Fab')$_2$ segment. In one embodiment, the antibody recognizes ErbB2.

In one embodiment, the binding moiety is a protein or the nucleic acid binding domain of a protein, and the binding moiety is fused to the carboxy portion of the targeting moiety. The location of the targeting moiety may be either in the carboxyl-terminal or amino-terminal end of the construct or in the middle of the fusion protein. Alternatively, the fusion protein may comprise more than one siRNA binding moieties and one or more targeting moieties.

In one preferred embodiment, the binding moiety is the nucleic acid binding domain of a protein selected from the group of nucleic acid binding domains present in proteins selected from the group consisting of protamine, GCN4, Fos, Jun, TFIIS, FMRI, yeast protein HX, Vigillin, Mer1, bacterial polynucleotide phosphorylase, ribosomal protein S3, and heat shock protein. In one preferred embodiment, the binding moiety is the protein protamine or an RNA interference-inducing molecule-binding fragment of protamine.

The target organism can be any single or multicellular organism. If the target animal or cell is a human or a human cell, the RNA interference-inducing molecule, preferably siRNA, binding moiety should preferably be a human RNA binding moiety, such as protamine or an RNA-binding fragment of protamine.

In one embodiment, the siRNA targets mRNA encoding c-myc, VEGF, CD4, CCR5, gag, MDM2, Apex, Ku70, or ErbB2.

In one embodiment, the cell is a cultured cell. Alternatively, the cell is part of an organ. Alternatively, the cell is part of a subject animal. In one embodiment, the cell is selected from the group consisting of hepatocytes, myocytes, neural cells, lipocytes, lymphocytes, macrophages, cardiac cells, endothelial cells, and epithelial cells. In another embodiment, the cell is a malignant cell including a lung cancer cell, a retinal cancer cell, a breast cancer cell, a ovarian cancer cell, a prostate cancer cell, a head and neck cancer cell, a lymphoma cell, a melanoma cell, a glioma cell, a bladder cancer cell, a genital-urinary cancer cell, a stomach cancer cell, a pancreatic cancer cell, a liver cancer cell, a kidney cancer cell, or a gastrointestinal cancer cell. In another embodiment, the cell is a stem cell, including, for example, an adult stem cell or an embryonic stem cell.

In another preferred embodiment, the invention provides a method of delivering RNA interference into a cell, the method comprising contacting the cell with a fusion protein-double stranded RNA complex, the complex comprising (a) an RNA molecule comprising a double stranded RNA segment, wherein one of the strands is complementary and the other strand identical to an RNA interference target RNA; and (b) a fusion protein, comprising (1) a targeting moiety, which specifically binds to a site on a target cell, and (2) a binding moiety, which binds to the double stranded RNA segment, wherein the double stranded RNA segment initiates RNA interference in the cell. Preferably, the double stranded RNA is an siRNA.

In one embodiment, the targeting moiety is an antibody, including antibodies recognizing a viral envelope protein, a cellular receptor, or an extracellular domain of an activated receptor. Preferably, the antibody is a single chain antibody, a Fab portion of an antibody or a (Fab')$_2$ segment. Preferably, the antibody recognizes ErbB2, gp120 or gp160.

In another preferred embodiment, the targeting moiety is a cell surface receptor ligand including ligands to the cell surface receptors CD4, CCR5 and CXCR4.

In one embodiment, the binding moiety is a protein or the nucleic acid binding domain of a protein, and the binding moiety is fused to the carboxyl portion of the targeting moiety. Preferably, the binding moiety is the nucleic acid binding domain of a protein selected from the group of nucleic acid binding domains present in proteins selected from the group consisting of GCN4, Fos, Jun, TFIIS, FMRI, yeast protein HX, Vigillin, Mer1, bacterial polynucleotide phosphorylase, ribosomal protein S3, and heat shock protein. Preferably, the binding moiety is the protein protamine or an RNA interference-inducing molecule-binding fragment of protamine.

In one embodiment, the siRNA targets mRNA encoding c-myc, VEGF, CD4, CCR5, gag, MDM2, Apex, Ku70, or ErbB2.

In one embodiment, the cell is a cultured cell. Alternatively, the cell is part of an organ. Alternatively, the cell is part of a subject animal. In one embodiment, the cell is selected from the group consisting of hepatocytes, myocytes, neural cells, lipocytes, lymphocytes, macrophages, cardiac cells, endothelial cells, and epithelial cells. In another embodiment, the cell is a malignant cell including a lung cancer cell, a retinal cancer cell, a breast cancer cell, a ovarian cancer cell, a prostate cancer cell, a head and neck cancer cell, a lymphoma cell, a melanoma cell, a glioma cell, a bladder cancer cell, a genital-urinary cancer cell, a stomach cancer cell, a pancreatic cancer cell, a liver cancer cell, a kidney cancer cell, or a gastrointestinal cancer cell. In another embodiment, the cell is a stem cell, including, for example, an adult stem cell or an embryonic stem cell.

In one embodiment, the invention provides a method of delivering siRNA into cells in vivo. In one preferred embodiment the siRNA-containing complex is delivered into cells via direct injection of the complex in a pharmaceutically acceptable carrier into tumors. In another embodiment, siRNA-containing complex is delivered by injecting it intravenously in a pharmaceutically acceptable carrier into the subject. One preferred method is a topical administration of the siRNA-containing complex. In one embodiment, the siRNA complex is delivered intravaginally.

In one embodiment, the invention provides a method for treatment of tumor cells. The method comprises fusing a target moiety comprising a tumor cell specific antibody or tumor cell specific receptor ligand with the desired siRNA binding protein, for example protamine, and preparing a mixture comprising siRNA combined with the fusion protein and delivering such complex into a subject in need of tumor cell specific inhibition of gene expression.

In another embodiment, the invention provides a method for treating viral diseases. The method comprises preparing a fusion protein comprising a target-specific moiety comprising a viral envelope protein specific antibody and an siRNA binding moiety, preferably protamine, and combining the fusion protein with the desired siRNA and delivering such complex into a subject in need of virus infected cell specific inhibition of gene expression.

In yet another embodiment, the invention provides a method of treating a parasitic disease, such as malaria. The method comprises preparing a fusion protein comprising a target-specific moiety comprising a parasite protein specific antibody with an siRNA-binding moiety, preferably protamine and combining the fusion protein with the desired siRNA and delivering such complex into a subject in need of parasite specific inhibition of gene expression.

In one embodiment, the invention provides a method for screening targets of pharmaceutical intervention. The method comprises delivering a plurality of different siRNAs into cells in parallel cell culture environments using a fusion protein comprising a target moiety and an siRNA binding moiety that is combined or mixed with the specific different siRNAs, and measuring the effects of silencing the siRNA targeted genes. The method may additionally comprise addition of test agents, such as small organic and/or inorganic molecules, drugs, modified and unmodified nucleic acids and the like into the cells first treated with the siRNA and measuring the effects of the addition of the test agent on the function of the cells wherein the specific genes have been silenced using siRNA.

BRIEF DESCRIPTION OF FIGURES

FIG. 2A shows control Jurkat cells uninfected (left) or infected (right) with HIV IIIB, and evaluated for infection by intracellular staining for HIV gag p24.45% of the cells are productively infected with HIV. FIG. 2B shows that siRNA is delivered into approximately half of the infected cells (21% of total cells) only by F105-protamine but not by itself or by F105 without protamine. There is no uptake by uninfected cultures. As a positive control, cells were transfected with Oligofectamine. There was no difference in uptake between infected and uninfected cells when the siRNAs were transfected.

FIG. 8D shows green fluorescent staining only in the tumor nest, while FIG. 8F shows green fluorescent staining in the tumor nest as well as in the surrounding tissue.

(FIG. 9A) into the right flank, where the tumor cells were implanted, or i.v. (FIG. 9B) with either a combination of siRNA (2 duplexes of c-myc siRNA, mdm2 siRNA and VEGF siRNA at 20 μg/duplex) complexed with F105-P at 6:1 molar ratio, or with siRNAs alone or PBS at a volume of 100 μl. Tumor size was followed daily from day 5 after inoculation. Parental B16 cells not expressing gp160 were not inhibited.

FIG. 10A shows that each F105-P molecule can bind approximately 6 FITC-labeled siRNA molecules. A fixed amount of FITC-siRNA was incubated with varying amounts of F105-P bound to anti-protamine-coupled beads and binding of bead-bound FITC-siRNA measured by fluorescence intensity compared to a standard curve. FIG. 10B shows that F105-P delivers FITC-labeled siRNA only into HIV-infected Jurkat cells. Jurkat cells were either uninfected (top row, left) or infected (top row, right) with HIV IIIB. About 82% of cells became productively infected as assessed by intracellular staining for HIV p24. HIV env antibody coupled to protamine (F105-P), but not uncoupled antibody (F105), protamine (P), irrelevant ErbB2 single chain antibody coupled to protamine (ErbB2-P) or medium alone, delivers FITC-labeled siRNA only into gated infected Jurkat cells. Approximately 40% of the HIV-infected cells took up FITC-labeled siRNA, while the uninfected cells did not. There was no difference in uptake between infected and uninfected cells when the siRNAs were transfected. FIG. 10C shows that F105-P delivers gag-siRNA into HIV env-expressing gp160-B16 cells, but not into env-negative B16 cells. Cells were analyzed 2 d after treatment by modified Northern blot probed with gag siRNA antisense strand. Transfected cells serve as a positive control for delivery.

FIGS. 13D-13G show proliferation of gp160-B16 cells treated with F105-P-delivered siRNAs directed against two c-myc sequences (FIG. 13D), MDM2 (FIG. 13E), VEGF (FIG. 13F) or combinations of siRNAs (FIG. 13G). The effect of transfecting 100 pmol siRNA (100 T) in (FIG. 13D-13F) is comparable to F105 delivery of 100-300 pmol siRNA. Additional simultaneous controls performed for (FIGS. 13D-13F) showed no difference in proliferation with GFP-siRNA or when cells were treated with only siRNA or FP105. Combinations of siRNAs were more efficient at inhibiting tumor growth than single agents. FIG. 13H shows siRNAs complexed with F105-P had no effect on the growth of B16 cells not expressing HIV env. * denotes $P<0.001$, while # denotes $P<0.001$ as compared with untreated control. FIG. 13I shows IFN-β and the interferon response genes STAT1 and OAS1, measured by quantitative RT-PCR, were not significantly induced 1 day following mock treatment (left bars—difficult to see above abscissa) or exposure to F105-P-delivered GFP-siRNA, but were induced by poly(I:C). Gene expression normalized to GAPDH mRNA.

FIG. 14A shows nine days after implanting gp160-B16 (left) or B16 melanoma cells (right) into the flanks of mice, FITC-siRNAs complexed with F105-P or oligofectamine were injected into the subcutaneous tumors. No staining was observed in gp160-B16 cells for FITC-siRNAs delivered alone. No staining was observed in B16 cells for FITC-siRNAs complexed with F105-P or delivered alone. FIG. 14B shows a high power image of tumor cells injected with F105-P and FITC-siRNA shows fluorescent staining in the cytoplasm. FIG. 14C shows F105-P loaded with FITC-siRNA was injected intravenously. The tumors were harvested 12 hr later for fluorescence microscopy (upper row) and hematoxylin and eosin staining (lower row). No staining was observed for gp160-B16 cells for FITC-siRNAs delivered alone or for B16 cells for FITC-siRNAs complexed with F105-P. F105-P specifically delivers FITC-siRNA in vivo only into gp160-B16 tumors, but not into surrounding normal tissue or B16 tumors lacking env, while oligofectamine delivers FITC-siRNA into both tumor and neighboring tissues. Naked siRNAs do not efficiently get into any cells. Intratumoral injection is more efficient than intravenous injection. F105-P-delivered siRNAs targeting c-myc, MDM2 and VEGF suppress the outgrowth of gp160-B16 tumors in vivo. Mice were treated by intratumoral (FIG. 14D, FIG. 14E) or intravenous (FIG. 14F, FIG. 14G) injection on days 0, 1, and 3 after implanting B16 (dotted lines) or gp160-B16 cells (continuous and dashed lines) into the right flank in groups of 8 mice. A cocktail of siRNAs (c-myc no. 1 and no. 2, MDM2 and VEGF) complexed with F105-P (■) or siRNAs alone (□) was injected. Mice mock treated with PBS (Δ) served as a control. Tumor size (FIG. 14D, FIG. 14F) was measured daily and tumors were weighed (FIG. 14E, FIG. 14G) on day 9 when the animals were sacrificed. The antitumor siRNAs suppressed tumor growth only when delivered by F105-P and only for tumors expressing HIV env. * denotes $P<0.001$, # denotes $P<0.01$ and & denotes $P<0.05$ as compared with PBS-injected controls. Injection of F105-P without siRNA provided no protection.

FIG. 15A shows the single chain ErbB2 antibody protamine fusion protein ML39 ScFv-P binds to EbrB2$^+$ SKBR3 cells, but not to EbrB2$^-$ MCF7 cells (top row). Binding of the fusion protein is detected with His-tag antibody (red); isotype control-stained cells shown in white peak. ML39 ScFv-P delivers 100 pmol FITC-siRNA to 32% of SKBR3 cells but does not transduce MCF7 cells. The unmodified antibody, protamine alone, or medium does not deliver FITC-siRNA. FITC-siRNA is introduced into both cell lines by transfection. FIG. 15B shows delivery of Ku70-siRNA by ML39 ScVf-P reduces Ku70 expression only in ErbB2$^+$ cells. In the flow plots, the white histogram represents isotype antibody-stained cells; the red histogram, mock treated cells; and the grey histogram cells treated as indicated. Transfection of Ku70 siRNA equivalently reduces Ku70 expression in MCF7 cells (left) and SKBR3 cells (right). Delivery of Ku70 siRNA (1000 pmol) by ML39 ScVf-P, but not using control proteins or ML39 ScVf-P plus GFP siRNA, silences Ku70. MFI, mean fluorescence intensity. FIG. 15C shows dose response curve for Ku70 silencing using ML39 ScVf-P delivery. Ku70 MFI is shown. To achieve silencing comparable to that achieved with transfected siRNA (100 pmol, 100 T) requires about 1000 pmol of ML39 ScVf-P-delivered siRNA.

DETAILED DESCRIPTION OF THE INVENTION

Figure 1:
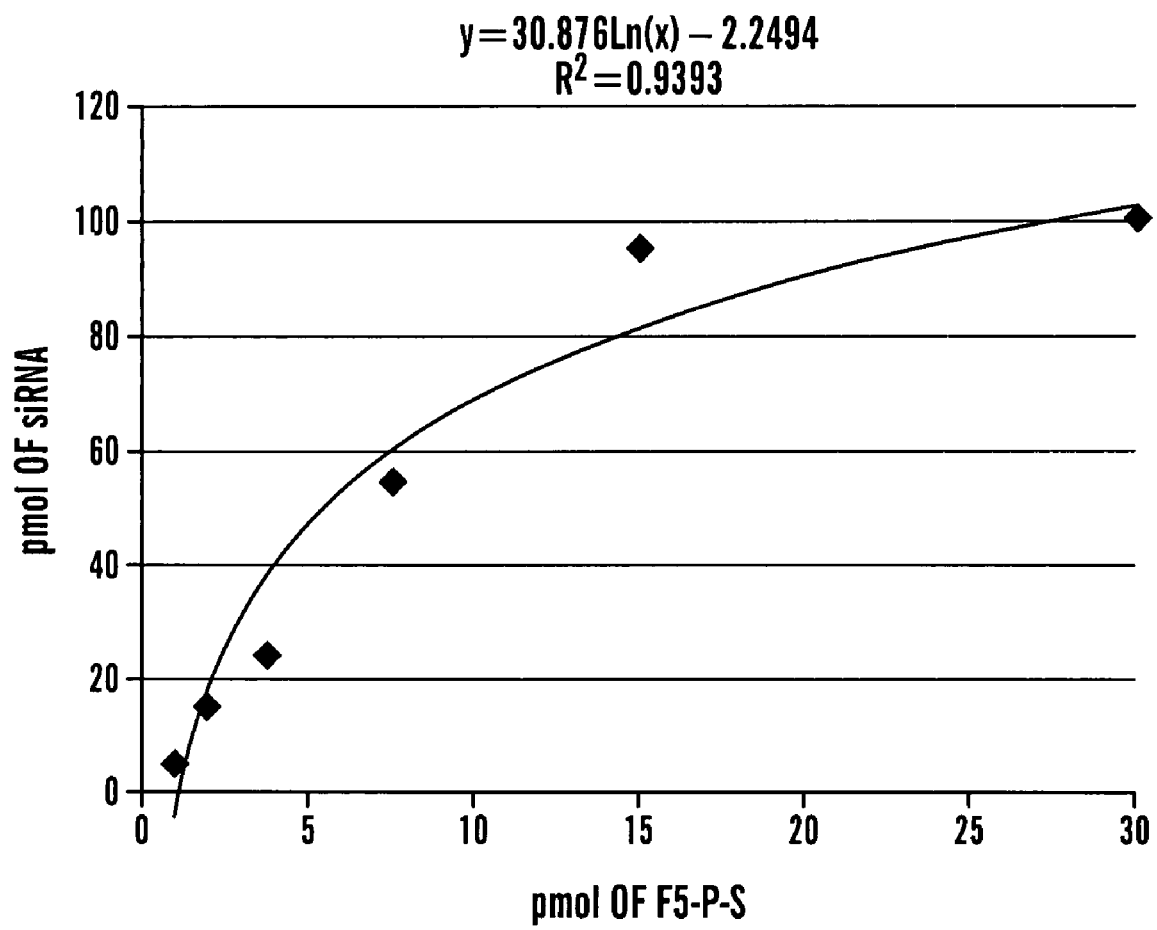
FIG. 1 shows the capacity of F105-protamine to bind siRNA. 100 pmol of FITC-siRNA was incubated for 30 min at room temperature with the indicated amount of F105-protamine attached to L-protein beads. Fluorescence at 488 nm of captured siRNA after washing was measured and compared to a standard curve of FITC-siRNA.

The present invention provides methods for targeted delivery of RNA interference, particularly short interfering RNA (siRNA) molecules or micro RNA molecules (miRNA) into cells both in vitro and in vivo. These methods are useful, for example, in treatment of diseases, wherein cell specific gene silencing is desired.

RNA interference (RNAi) is a mechanism of post-transcriptional gene silencing (PTGS) that has been described in plants, invertebrates, and mammalian cells (Sharp P. A. Nature Struct. Biol. 8:746-750, 2001; Bernstein et al. Nature 409:363-366, 2001, Hannon, G. J. Nature 418: 244-251, 2002). In mammals, exposure to shorter than about 30 base pairs (bp) long short interference RNA (siRNA) molecules leads to mRNA degradation with specificity to the target RNA (Elbashir et al., Genes Dev. 15:188-200, 2001; Elbashir et al. EMBO J. 20:6877-6888, 2001).

The advantage of RNAi lies in its high specificity and potent gene silencing, coupled with the fact that every gene is a potential target and every cell has the necessary machinery (reviewed in [1]). Although some questions remain about specificity and activation of off-target effects[2-4], none of these problems has yet been documented in vivo. Moreover, some potential untoward events can likely be avoided by judicious choice of sequences or chemical modification of siRNAs.

The main obstacle to developing siRNA as a small molecule drug is delivering it in vivo across the cell membrane to the cytoplasm where it can enter the RNAi pathway and guide the sequence-specific mRNA degradation. In the absence of transfection reagents or high pressures that may damage the plasma membrane, most cells, including cells that actively sample their environment, such as macrophages, do not take up siRNAs. An exception may be pulmonary epithelial cells, since protection against respiratory syncytial virus infection in the lung was achieved in one report by nasal instillation of siRNAs administered without any transfection reagent[5]. Early studies validating the therapeutic potential of siRNAs in mice used high-pressure (so-called hydrodynamic) intravenous injection to force siRNAs into cells[6]. However, hydrodynamic injection, which causes right-sided heart failure, is not practical for systemic human use. Although transfection can deliver siRNAs locally, a systemic method to deliver siRNAs to specific cells via cell surface receptors would provide a means to introduce siRNAs into desired cells to achieve maximal therapeutic benefit, decrease the amount of drug required and avoid non-specific silencing and toxicity in bystander cells.

We took advantage of the nucleic acid binding properties of protamine, which nucleates DNA in sperm, to deliver siRNAs via an antibody Fab fragment-protamine fusion protein[7]. The Fab fragment was used to avoid potential side effects from interactions of complement and other molecules with the antibody constant region. A Fab antibody fragment directed against HIV envelope (F105) fused to protamine (F105-P), previously shown to carry plasmid DNA into HIV-infected cells[7,8], was used to deliver siRNAs and silence gene expression specifically in HIV-infected cells or cells transfected to express HIV env. siRNAs bound to the fusion protein and did not require covalent coupling for effective delivery. The strategy was effective at delivering siRNAs into primary cells, such as T lymphocytes, which are highly resistant to transfection. Using B16 melanoma cells transfected with an expression vector for HIV env, intravenous or intratumoral injection of F105-P-complexed siRNAs delivered siRNAs only into env-expressing tumors, but not into normal tissues or env-tumors, and inhibited tumor outgrowth when the siRNAs targeted oncogenes. This method can be generalized since we could use an antiErbB2-protamine fusion protein to deliver siRNAs specifically to ErbB2$^+$ breast cancer cells. This fusion protein used a single chain antibody expressed from baculovirus in insect cells.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116: 281-297), comprises a dsRNA molecule.

Double-stranded RNA, such as that used in siRNA, has different properties than single-stranded RNA, double-stranded DNA or single-stranded DNA. Each of the species of nucleic acids is bound by mostly non-overlapping sets of binding proteins in the cell and degraded by mostly non-overlapping sets of nucleases. The nuclear genome of all cells is DNA-based and as such is unlikely to produce immune responses except in autoimmune disease (Pisetsky. Clin Diagn Lab Immunol. 1998 January; 51:1-6). Single-stranded RNA (ssRNA) is the form endogenously found in eukaryotic cells as the product of DNA transcription. Cellular ssRNA molecules include messenger RNAs (and the progenitor pre-messenger RNAs), small nuclear RNAs, small nucleolar RNAs, transfer RNAs and ribosomal RNAs. Single-stranded RNA can induce interferon and inflammatory immune response via TLR7 and TLR8 receptors (Proc Natl Acad. Sci. 2004. 101:5598-603; Science. 2004. 303:1526-9; Science. 2004. 303:1529-3). Double-stranded RNA induces a size-dependent immune response such that dsRNA larger than 30 bp activates the interferon response, while shorter dsRNAs feed into the cell's endogenous RNA interference machinery downstream of the Dicer enzyme. MicroRNAs (miRNAs), including short temporal RNAs and small modulatory RNAs, are the only known cellular dsRNA molecules in mammals and were not discovered until 2001 (Kim. 2005. Mol. Cells. 19:1-15). Response to extracellular RNA in the bloodstream, double- or single-stranded of any length, is rapid excretion by the kidneys and degradation by enzymes (PLOS Biol. 2004. 2:18-20).

Numerous specific siRNA molecules have been designed that have been shown to inhibit gene expression (Ratcliff et al. Science 276:1558-1560, 1997; Waterhouse et al. Nature 411: 834-842, 2001). In addition, specific siRNA molecules have been shown to inhibit, for example, HIV-1 entry to a cell by targeting the host CD4 protein expression in target cells thereby reducing the entry sites for HIV-1 which targets cells expressing CD4 (Novina et al. Nature Medicine, 8:681-686, 2002). Short interfering RNA have further been designed and successfully used to silence expression of Fas to reduce Fas-mediated apoptosis in vivo (Song et al. Nature Medicine 9:347-351, 2003).

It has been shown in plants that longer, about 24-26 nt long siRNA correlates with systemic silencing and methylation of homologous DNA. Conversely, the about 21-22 nt short siRNA class correlates with mRNA degradation but not with systemic signaling or methylation (Hamilton et al. EMBO J. 2002 Sep. 2; 21(17):4671-9). These findings reveal an unexpected level of complexity in the RNA silencing pathway in plants that may also apply in animals. In higher order eukaryotes, DNA is methylated at cytosines located 5' to guanosine in the CpG dinucleotide. This modification has important regulatory effects on gene expression, especially when involving CpG-rich areas known as CpG islands, located in the promoter regions of many genes. While almost all gene-associated islands are protected from methylation on autosomal chromosomes, extensive methylation of CpG islands has been associated with transcriptional inactivation of selected imprinted genes and genes on the inactive X-chromosomes of females. Aberrant methylation of normally unmethylated CpG islands has been documented as a relatively frequent event in immortalized and transformed cells and has been associated with transcriptional inactivation of defined tumor suppressor genes in human cancers. In this last situation, promoter region hypermethylation stands as an alternative to coding region mutations in eliminating tumor suppression gene function (Herman, et al.). The use of siRNA molecules for directing methylation of a target gene is described in U.S. Provisional Application No. 60/447,013, filed Feb. 13, 2003, referred to in U.S. Patent Application Publication No. 20040091918.

It is also known that the RNA interference does not have to match perfectly to its target sequence. Preferably, however, the 5' and middle part of the antisense (guide) strand of the siRNA is perfectly complementary to the target nucleic acid sequence.

The RNA interference-inducing molecule according to the present invention includes RNA molecules that have natural or modified nucleotides, natural ribose sugars or modified sugars and natural or modified phosphate backbone.

Accordingly, the RNA interference-inducing molecule referred to in the specification includes, but is not limited to, unmodified and modified double stranded (ds) RNA molecules including, short-temporal RNA (stRNA), small interfering RNA (siRNA), short-hairpin RNA (shRNA), microRNA (miRNA), double-stranded RNA (dsRNA), (see, e.g. Baulcombe, Science 297:2002-2003, 2002). The dsRNA molecules, e.g. siRNA, also may contain 3' overhangs, preferably 3'UU or 3'TT overhangs. In one embodiment, the siRNA molecules of the present invention do not include RNA molecules that comprise ssRNA greater than about 30-40 bases, about 40-50 bases, about 50 bases or more. In one embodiment, the siRNA molecules of the present invention have a double stranded structure. In one embodiment, the siRNA molecules of the present invention are double stranded for more than about 25%, more than about 50%, more than about 60%, more than about 70%, more than about 80%, more than about 90% of their length.

As used herein, "gene silencing" induced by RNA interference refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without introduction of RNA interference. In one preferred embodiment, the mRNA levels are decreased by at least about 70%, about 80%, about 90%, about 95%, about 99%, about 100%.

The RNA interference as described herein also includes RNA molecules having one or more non-natural nucleotides, i.e. nucleotides other than adenine "A", guanine "G", uracil "U", or cytosine "C", a modified nucleotide residue or a derivative or analog of a natural nucleotide are also useful. Any modified residue, derivative or analog may be used to the extent that it does not eliminate or substantially reduce (by at least 50%) RNAi activity of the dsRNA. These forms thus include, but are not limited to, aminoallyl UTP, pseudo-UTP, 5-I-UTP, 5-I-CTP, 5-Br-UTP, alpha-S ATP, alpha-S CTP, alpha-S GTP, alpha-S UTP, 4-thio UTP, 2-thio-CTP, 2'NH$_2$ UTP, 2'NH$_2$ CTP, and 2' UTP. Such modified nucleotides include, but are not limited to, aminoallyl uridine, pseudo-uridine, 5-I-uridine, 5-I-cytidine, 5-Br-uridine, alpha-S adenosine, alpha-S cytidine, alpha-S guanosine, alpha-S uridine, 4-thio uridine, 2-thio-cytidine, 2'NH2 uridine, 2'NH2 cytidine, and 2'F uridine, including the free pho (NTP) RNA molecules as well as all other useful forms of the nucleotides.

The RNA interference as referred herein additionally includes RNA molecules which contain modifications in the ribose sugars, as well as modifications in the "phosphate backbone" of the nucleotide chain. For example, siRNA or miRNA molecules containing α-D-arabinofuranosyl structures in place of the naturally-occurring α-D-ribonucleosides found in RNA can be used in RNA interference according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotides molecules similar to the oligonucleotides containing 2'-O-methyl ribose, arabinose and particularly α-arabinose (U.S. Pat. No. 5,177,196). Also, phosphorothioate linkages can be used to stabilize the siRNA and miRNA molecules (U.S. Pat. No. 5,177,196). siRNA and miRNA molecules having various "tails" covalently attached to either their 3'- or to their 5'-ends, or to both, are also been known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Various specific siRNA and miRNA molecules have been described and additional molecules can be easily designed by one skilled in the art. For example, the miRNA Database at http://www.sanger.ac.uk/Software/Rfam/mirna/index.shtml provides a useful source to identify additional miRNAs useful according to the present invention (Griffiths-Jones S, NAR, 2004, 32, Database Issue, D109-D111; Ambros V, Bartel B, Bartel D P, Burge C B, Carrington J C, Chen X, Dreyfas G, Eddy S R, Griffiths-Jones S, Marshall M, Matzke M, Ruvkun G, Tuschl T. RNA, 2003, 9(3), 277-279).

An "siRNA" as used herein and throughout the specification refers to a nucleic acid that forms a double stranded RNA, which double stranded RNA has the ability to reduce or inhibit expression of a gene or target gene when the siRNA is expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

siRNAs also include small hairpin (also called stem loop) RNAs (shRNAs). In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand may precede the nucleotide loop structure and the antisense strand may follow.

In one preferred embodiment, the siRNAs useful according to the present invention are selected from the group consisting of:

C-myc #1: 5-GAACAUCAUCAUCCAGGAC-3 (sense, SEQ ID NO: 13); CUUGUAGUAGUAGGUCCUG (antisense, SEQ ID NO: 14, FEBS Lett. 2004 Feb. 27; 560(1-3): 210-4);

C-myc #2: 5-ACUCGAACAGCUUCGAAAC-3 (sense, SEQ ID NO: 15); UGAGCUUGUCGAAGCUUUG (antisense, SEQ ID NO: 16, Id)

VEGF: 5-CGAUGAAGCCCUGGAGUGC-3 (sense, SEQ ID NO: 17); GCACUCCAGGGCUUCAUCG (antisense, SEQ ID NO: 18, Mol Vis. 2003 May 30; 9: 210-6).

MDM2: 5'GCUUCGGAACAAGAGACUCdTdT (sense, SEQ ID NO: 7); 3'dTdTGGUUGUGACGAAUGCGAAU (antisense, SEQ ID NO: 8);

Apex1: 5'-CCAACACUGCUUACGCUUAdTdT-3' (sense, SEQ ID NO: 9); 3'-dTdTGGUUGUGACGAAUGCGAAU (antisense, SEQ ID NO: 10);

pp32: 5'-AAGAAGCUUGAAUUAAGCGdTdT-3' (sense, SEQ ID NO: 11); 3'-dTdTUUCUUCGAACUUAAUUCGC-5' (antisense, SEQ ID NO: 12); and Ku70: 5'-ACGGAUCUGACUACUCACUCAdTdT-3' (sense, SEQ ID NO: 19); 3'-dTdTUGCCUAGACUGAUGAGUGAGU-5' (antisense, SEQ ID NO:20).

In another embodiment, siRNAs useful according the methods of the present invention are found in WO 05/042719, WO 05/013886, WO 04/039957, and U.S. Pat. App. No. 20040248296. Other useful siRNAs useful in the methods of the present invention include, but are not limited to, those found in U.S. Pat. App. Nos. 20050176666, 20050176665, 20050176664, 20050176663, 20050176025, 20050176024, 20050171040, 20050171039, 20050164970, 20050164968, 20050164967, 20050164966, 20050164224, 20050159382, 20050159381, 20050159380, 20050159379, 20050159378, 20050159376, 20050158735, 20050153916, 20050153915, 20050153914, 20050148530, 20050143333, 20050137155, 20050137153, 20050137151, 20050136436, 20050130181, 20050124569, 20050124568, 20050124567, 20050124566, 20050119212, 20050106726, 20050096284, 20050080031, 20050079610, 20050075306, 20050075304, 20050070497, 20050054598, 20050054596, 20050053583, 20050048529, 20040248174, 20050043266, 20050043257, 20050042646, 20040242518, 20040241854, 20040235775, 20040220129, 20040220128, 20040219671, 20040209832, 20040209831, 20040198682, 20040191905, 20040180357, 20040152651, 20040138163, 20040121353, 20040102389, 20040077574, 20040019001, 20040018176, 20040009946, 20040006035, 20030206887, 20030190635, 20030175950, 20030170891, 20030148507, 20030143732, and WO 05/060721, WO 05/060721, WO 05/045039, WO 05/059134, WO 05/045041, WO 05/045040, WO 05/045039, WO 05/027980, WO 05/014837, WO 05/002594, WO 04/085645, WO 04/078181, WO 04/076623, and WO 04/046354.

The RNA interference according to the present invention can be produced using any known techniques such as direct chemical synthesis, through processing of longer double stranded RNAs by exposure to recombinant Dicer protein or Drosophila embryo lysates, through an in vitro system derived from S2 cells, using phage RNA polymerase, RNA-dependant RNA polymerase, and DNA based vectors. Use of cell lysates or in vitro processing may further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836 that teach chemical and enzymatic synthesis of siRNA. Moreover, numerous commercial services are available for designing and manufacturing specific siRNAs (see, e.g., QIAGEN Inc., Valencia, Calif. and AMBION Inc., Austin, Tex.)

The RNA interference, useful in the methods of the present invention include siRNAs that target gene expression of any protein encoded inside a eukaryotic cell. Examples of these proteins include endogenous mammalian proteins, parasitic proteins, viral proteins encoded by an eukaryotic cell after entry of a virus into the cell. Examples of methods of preparing such RNA interference are shown, for example in an international patent application Nos. PCT/US03/34424, PCT/US03/34686, and U.S. provisional patent applications No. 60/488,501, 60/488,155 and 60/516,172 the contents and references of all of these patent applications are herein incorporated by reference in their entirety.

Unlike the siRNA delivery methods described in the prior art, the method of the present invention allows targeting of specific cells to minimize or to avoid completely undesired potential side effects of siRNA therapy.

The target cell types, to which RNA interference can be delivered using the methods of the invention include eukaryotic cells including, but not limited to hepatocytes, myocytes, neural cells, lipocytes, lymphocytes, macrophages, cardiac cells, endothelial cells, epithelial cells, and the like. In one embodiment, the target cell type is a tumor cell or a cancer cell including, but not limited to lung cancer cell, retinal cancer cell, breast cancer cell, ovarian cancer cell, prostate cancer cell, head and neck cancer cell, lymphoma cell, melanoma cell, glioma cell, bladder cancer cell, genital-urinary cancer cell, stomach cancer cell, pancreatic cancer cell, liver cancer cell, kidney cancer cell, gastrointestinal cancer and the like. In one preferred embodiment, the target cells are selected from the group consisting of human lymphocytes, human dendritic cells, human adult stem cells and embryonic stem cells.

Additionally, the methods of the present invention provide means to target malignant or tumor cells specifically, because these cells express typically a variety of specific proteins on their surface and thus can be targeted using the cell targeting moiety of the fusion protein in the RNA interference delivery system of the present invention.

The target moiety specifically brings the delivery system to the target cell. The particular target moiety for delivering the interference RNAs, including siRNAs, can be determined empirically based upon the present disclosure and depending upon the target cell. For example, with somatic cell therapy in vivo with readily accessible cells or tissues such as an intravascular target, immune cell target or the like, the important attributes of the target moiety are affinity and selectivity.

The method of the present invention provides a system to deliver siRNA into a limited number of cells thereby limiting, for example, potential side effects of therapies using siRNA. The particular cell surface targets that are chosen for the targeting moiety will depend upon the target cell. Cells can be specifically targeted, for example, by use of antibodies against unique proteins, lipids or carbohydrates that are present on the cell surface. A skilled artisan is easily able to determine such molecules based on the general knowledge in the art.

For example, if one is targeting an infected cell, such as an HIV infected cell, one can use a monoclonal antibody that will specifically target HIV infected cells. This would include use of an antibody against the envelope glycoprotein. One can use any of a number of known antibodies against HIV-1 gp120 or HIV-2 gp120, such as 15e, 21h (Thali, M., et al., J. Virol. 67:3978-3988 (1993)), F105, 176 and 48d. If one wants to deliver the nucleic acid sequence prophylactically such as a gene for intracellular expression of an antibody, a decoy sequence, etc., one can target highly susceptible cells by targeting receptors present on such cells such as the CD4 or CCR5 receptors for HIV susceptible cells. In such a situation, the protein can be a ligand that will preferentially bind to the cell surface receptor responsible for virus entry, for example, CD4 or CCR5, or an antibody to the receptor, such as an antibody to the CD4 or CCR5 receptor.

This strategy for choosing the targeting moiety is very adaptable. For example, any cell-specific antigen, including proteins, carbohydrates and lipids can be used to create an antibody that can be used to target the siRNA to a specific cell type according to the methods of the present invention. For example, certain tumors frequently possess a large amount of a particular cell surface receptor (e.g. neu with breast cancers), or an abnormal form of a particular protein. Therefore, a tumor antigen can serve as a specific target to deliver siRNA into the tumor cells to inhibit growth and/pr proliferation of the cell or to destroy the cell. Any known tumor antigen expressed on the tumor cell surface can be used for generating an antibody to serve as a targeting moiety. For example, tumor antigens useful according to the present invention include, but are not limited to, mini-MUC; MUC-1 (Marshall et al., J. CLin. Oncol. 18:3964-73 (2000); HER2/neu; HER2 receptor (U.S. Pat. No. 5,772,997); mammoglobulin (U.S. Pat. No. 5,922,836); labyrinthin (U.S. Pat. No. 6,166,176); SCP-1 (U.S. Pat. No. 6,140,050); NY-ESO-1 (U.S. Pat. No. 6,140,050); SSX-2 (U.S. Pat. No. 6,140,050); N-terminal blocked soluble cytokeratin (U.S. Pat. No. 4,775,620); 43 kD human cancer antigen (U.S. Pat. No. 6,077,950); human tumor associated antigen (PRAT) (U.S. Pat. No. 6,020,478); human tumor associated antigen (TUAN) (U.S. Pat. No. 5,922,566); L6 antigen (U.S. Pat. No. 5,597,707); carcinoembryonic antigen (RT-PCR analysis for breast cancer prognosis in Clin Cancer Res 6:4176-85, 2000); CA15-3 (Eur J Gynaecol Oncol 21:278-81, 2000); oncoprotein 18/stathmin (Op18) (Br J. Cancer 83:311-8, 2000); human glandular kallikrein (hK2) (Breast Cancer Res Treat 59:263-70, 2000); NY-BR antigens (Cancer Immun. March 30; 1:4, 2001), tumor protein D52 (Cancer Immun. March 30; 1:4, 2001), and prostate-specific antigen (Breast Cancer Res Treat 59:263-70, 2000); and EEA.

Any known and identifiable viral antigens can be used to generate specific antibodies recognizing cells that are infected with viruses. Specific targets include, for example, viral envelope and other such proteins encoded by viral genomes.

Parasite antigens include, for example, malaria causing *P. falciparum* antigens, and can also be used to generate antibodies useful according to the present invention. Non-limiting examples of *P. falciparum* antigens useful according to the present invention can be found in U.S. Pat. No. 6,663,871 and references cited therein.

Other receptors of interest include those for lymphokines such as interleukins and interferons, for example, the interleukin-2 (IL-2) receptor (IL-2R). The p55, IL-2R alpha chain also referred to as the Tac protein is associated with Ag or mitogen-activated T-cells but not resting T-cells. It is expressed in high levels on malignant cells of lymphoid cancers such as adult T-cell leukemia, cutaneous T-cell lymphoma and Hodgkins disease. The anti-Tac antibody will bind to this protein. Humanized version of such antibodies are known and described in Queen, C., et al., Proc. Natl. Acad. Sci. USA:10029-10039 (1989); Hakimi, J., et al., J. of Immun. 151:1075-1085 (1993) (Mik.beta.1 which is a Mab against IL-2R .beta. chain); Kreitman, R. J., et al., J. of Immun. 149:2810-2815 (1992); Hakimi, J., et al., J. of Immun. 147:1352-1359 (1991).

Antibodies to these various proteins are known and available. These antibodies can readily be adapted for use in this system by following the general procedures described herein, and substituting the gene coding for the desired binding site for the exemplified gene. For example, where the targeted cell is an HIV-infected cell, the targeting moiety can target the HIV envelope glycoprotein. Any number of antibodies to this protein can be used. For instance, a recombinant antibody based on the F105 antibody is made by known teaching techniques. (Posner, M. R., et al., J. Immunol. 146:4325-4332 (1991); Thali, M., et al, J. Virol. 65:6188-6193 (1991); Marasco, W. A., et al., Proc. Natl. Acad, Sci. USA 90:7889-7893 (1993)) other antibodies that can be made include, 15e, 21h, 17b, 48d, etc.

In one preferred embodiment, the targeting moiety of the present invention is F105 antibody. The F105 monoclonal antibody, identified in an HIV-infected individual, binds to a discontinuous epitope of an HIV-1 gp120 envelope glycoprotein and blocks binding of gp120 to the CD4 viral receptor. The nucleotide sequence of the F105 has been determined and can be found, for example in Marasco et al., J. Clin. Invest. 90:1467-1478, 1992. A vector for expressing the antibody can be made as described in the U.S. Patent Application Publication No. 20040023902 and examples therein.

Shortly, a bicistronic mammalian expression vector which expresses the amino terminal (antigen-binding) end (Fd fragment) of the heavy chain of the antibody ($V_H$ and $C_H$) and the binding region of the light chain (e.g., a kappa chain) of the F105 antibody can be constructed by using an Fd fragment without a stop codon and amplifying the segment by standard techniques, for example, by polymerase chain reaction (PCR). The upstream PCR primer preferably will correspond to the leader sequence of the immunoglobulin of the animal from which the cells of the delivery agent are to be used. For example, where the target cell is a human cell a human immunoglobulin leader sequence comprising amino acids 1-6 (see, e.g., human immunoglobulin heavy chain GenBank accession No. CAA28307, version GI:683576), wherein an additional convenient cloning site such as a HindIII site can be added. The cloning site can be added, for example, by adding the sequence of the restriction enzyme recognition site to the PCR amplification primer. The downstream PCR primer for the F105 can be designed to correspond to amino acids by the carboxyl terminus of the heavy chain constant region. For example, when the antibody is based upon F105, amino acids 226-233 of human immunoglobulin heavy chain, including the first constant region domain (CHI, also known as CH1, also known as $C_H1$ domain, see, e.g., nucleic acid sequence for human gene and mRNA for IgG chain constant and hinge regions with GenBank accession No. X04646, gi: 33061). A convenient cloning site can be added into the downstream primer as well to facilitate cloning of the nucleic acid into an appropriate vector. The PCR reaction is performed according to standard means well known to one skilled in the art.

In another preferred embodiment, the targeting moiety of the present invention is a single chain antibody fragment, ML39 scFv, that recognizes the ErbB2 receptor (Li et al. "Single-chain antibody-mediated gene delivery into ErbB2-positive human breast cancer cells" Cancer Gene Ther. 2001; 8:555-65). ML39 scFV recognizes the ErbB2 receptor and as such is useful as a targeting moiety in the methods of the present invention for targeting and delivery to cells expressing ErbB2, for example, breast cancer cells. Methods for producing a fusion protein containing an ML39 scFv targeting moiety are described below and in Li et al. 2001 (supra).

Other useful targeting moieties are a single chain antibody fragment to the transferrin receptor described in, for example, Xu et al. (Mol Cancer Ther. 2002, 1(5):337-46) and the single chain antibody fragment recognizing prostate specific membrane antigen described in, for example, Li et al. (Intl J Oncology. 2003, 23: 1329-1332).

Any antibody with a known sequence can be used to prepare a similar construct as described above.

As described, the second portion of the fusion protein is the binding moiety. Preferably, one uses a single vector containing gene segments that will express both the targeting moiety and the binding moiety. However, one can use a vector system to co-transfect a cell with at least two vectors and select for cells expressing the fusion protein. Preferably, one uses a single vector. One preferably attaches the sequence encoding the target moiety to a gene, or gene segment, encoding the binding moiety by standard means. For example, a gene for human protamine (Balhorn, J. of Cell. Biol. 93:298-305 (1982)).

Ligands for particular target cell receptors or enzymes present on cell surface may be used as a targeting moiety. For example, if the target cell is a T lymphocyte, one possible target is the CD4 receptor or its co-receptors, such as CCR5 or CXCR4, which may also serve as targets, and a preferable ligand is an HIV envelope protein gp120 or a fragment of gp120 that is known to bind the CD4 receptor or its co-receptors, such as CCR5 or CXCR4. Alternatively, if the target is cell-surface glycosyltransferase, such as galactosyltransferase, the ligand can be selected, for example, from D-galactose, N-acetyl-D-glucosamine, and uridine. The ligands can be conjugated to the RNA-binding motif using known methods in the art.

If antibodies are used as a targeting moiety, the use of single chain antibodies as the target moiety is preferable. However, when the target cell is not readily accessible, such as when the cell is part of a large solid tumor mass with a poor blood supply and high interstitial pressure, the serum half-life is important to consider. In such instances, the full antibody and $(Fab')_2$ segments are typically preferred. In a preferred embodiment, one could synthesize the fusion protein so that the binding moiety is attached to the carboxy-terminus of the light or heavy chain of an intact immunoglobulin, such as $IgG_1$.

In order to limit antigenic reaction, the targeting moiety is preferably selected to take into account the host animal whose cells will be targeted. Thus, if the target animal is a mouse, one preferably uses murine antibodies, whereas if the target animal is a human, one preferably uses a human antibody or a humanized antibody.

In one embodiment, a vector encoding siRNA is delivered into a specific target cell. As used herein, the term "vector" is used in reference to nucleic acid molecules that transfer DNA segment(s) from one cell to another. Vectors are often derived from plasmids, bacteriophages, or plant or animal viruses. The term "expression vector" as used herein refers to a recombinant DNA molecule containing a desired siRNA coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

One can also use localization sequences to deliver the released RNA interference-inducing molecule intracellularly to a cell compartment of interest. Typically, the delivery system first binds to a specific receptor on the cell. Thereafter, the targeted cell internalizes the delivery system, which is bound to the cell.

For example, membrane proteins on the cell surface, including receptors and antigens can be internalized by receptor mediated endocytosis after interaction with the ligand to the receptor or antibodies. (Dautry-Varsat, A., et al., Sci. Am. 250:52-58 (1984)). This endocytic process is exploited by the present delivery system. Because this process can damage the RNA interference-inducing molecule as it is being internalized, it may be desirable to use a segment containing multiple repeats of the RNA interference-inducing molecule of interest. One can also include sequences or moieties that disrupt endosoines and lysosomes. See, e.g., Cristiano, R. J., et al., Proc. Natl. Acad. Sci. USA 90:11548-11552 (1993); Wagner, E., et al., Proc. Natl. Acad. Sci. USA 89:6099-6103 (1992); Cotten, M., et al., Proc. Natl. Acad. Sci. USA 89:6094-6098 (1992).

Short interfering RNA (siRNA)-complex or micro interfering RNA (miRNA)-complex as referred to herein is a complex wherein a target moiety is complexed or mixed with the RNA interference, such as siRNA. Suitable siRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DE AE-albumin and DEAE-dextran, polymethylacrylate, polyhexylacrylate, poly(D,L-lactic acid), poly(DL-lactic-co-glycolic acid (PLGA), alginate, and polyethyleneglycol (PEG), and polyethylenimine. In one embodiment, the interference RNA-binding domain is selected from the nucleic acid binding domains present in proteins selected from the group consisting of GCN4, Fos, Jun, TFIIS, FMRI, yeast protein HX, Vigillin, Mer1, bacterial polynucleotide phosphorylase, ribosomal protein S3, and heat shock protein.

In one preferred embodiment, the siRNA complexing agent is protamine or an RNA-binding domain, such as an siRNA-binding fragment of protamine. Protamine is a polycationic peptide with molecular weight about 4000-4500 Da. Protamine is a small basic nucleic acid binding protein, which serves to condense the animal's genomic DNA for packaging into the restrictive volume of a sperm head (Warrant, R. W., et al., Nature 271:130-135 (1978); Krawetz, S. A., et al., Genomics 5:639-645 (1989)). The positive charges of the protamine can strongly interact with negative charges of the phosphate backbone of nucleic acid, such as RNA resulting in a neutral and, as shown here, stable interference RNA protamine complex.

In one embodiment, the protamine fragment useful according to the present invention is encoded by a nucleic acid sequence SEQ ID NO: 1, or a homolog thereof capable of encoding the same amino acids as the SEQ ID NO: 1:

```
                                           (SEQ ID NO: 1)
GCGGCCGCACGCAGCCAGAGCCGGAGCAGATATTACCGCCAGAGACAAAG

AAGTCGCAGACGAAGGAGGCGGAGCTGCCAGACACGGAGGAGAGCCATGA

GATCTCATCATCACCACCACCATTAA.
```

In one embodiment, the protamine fragment useful according to the present invention is encoded by a nucleic acid sequence SEQ ID NO: 2, or a homolog therefore capable of encoding the same amino acids as the SEQ ID NO: 2:

```
                                           (SEQ ID NO: 2)
GCGGCCGCAATGGCCAGGTACAGATGCTGTCGCAGCCAGAGCCGGAGCAG

ATATTACCGCCAGAGACAAAGAAGTCGCAGACGAAGGAGGCGGAGCTGCC

AGACACGGAGGAGAGCCATGAGATCTCATCATCACCACCACCATTAA.
```

In one embodiment, the protamine fragment useful according to the present invention is encoded by a nucleic acid sequence SEQ ID NO: 3, or a homolog therefore capable of encoding the same amino acids as the SEQ ID NO: 3:

```
                                           (SEQ ID NO: 3)
GCGGCCGCACGCAGCCAGAGCCGGAGCAGATATTACCGCCAGAGACAAAG

AAGTCGCAGACGAAGGAGGCGGAGCTGCCAGACACGGAGGAGAGCCATGA

GGTGTTGTCGCCCCAGGTACAGACCGAGATGTAGAAGACACAGATCTCAT

CATCACCACCACCATTAA
```

In one embodiment, the protamine fragment useful according to the present invention is encoded by a nucleic acid sequence SEQ ID NO: 4, or a homolog therefore capable of encoding the same amino acids as the SEQ ID NO: 4:

```
                                           (SEQ ID NO: 4)
GCGGCCGCACGCAGCCAGAGCCGGAGCAGATATTACCGCCAGAGACAAAG

AAGTCGCAGACGAAGGAGGCGGAGCAGATCTCATCATCACCACCACCATT

AA
```

In one embodiment, the protamine fragment useful according to the present invention is encoded by a nucleic acid sequence SEQ ID NO: 5, or a homolog therefore capable of encoding the same amino acids as the SEQ ID NO: 5:

```
                                           (SEQ ID NO: 5)
GCGGCCGCCGGCGGAGGAGGATCTCATCATCACCACCATTAA
```

In one embodiment, the protamine fragment useful according to the present invention is encoded by a nucleic acid sequence SEQ ID NO: 6, or a homolog therefore capable of encoding the same amino acids as the SEQ ID NO: 6:

```
                                           (SEQ ID NO: 6)
GCGGCCGCAATGGCCAGGTACAGATGCTGTCGCAGCCAGAGCCGGAGCAG

ATATTACCGCCAGAGACAAAGAAGTCGCAGACGAAGGAGGCGGAGCAGAT

CTCATCATCACCACCACCATTAA.
```

In the most preferred embodiment, the full length protamine is conjugated with gp160 antibody.

The methods, reagents and references that describe a preparation of a nucleic acid-protamine complex in detail are disclosed in the U.S. Patent Application Publication Nos. US2002/0132990 and US2004/0023902, and are herein incorporated by reference in their entirety.

The siRNA complex can be delivered using any delivery system such as topical administration, subcutaneous, intramuscular, intraperitoneal, intrathecal and intravenous injections, catheters for delivering the siRNA complexes into, for example, a specific organ, such as brain, liver, heart or kidneys, or into, for example, a specific location having been affected with malignant growth or viral infection. The siRNA complex can also be administered vaginally.

The "pharmaceutically acceptable carrier" means any pharmaceutically acceptable means to mix and/or deliver the siRNA-complexes to a subject. For the clinical use of the methods of the present invention, the siRNA-complex of the invention are formulated into pharmaceutical formulations for oral, rectal, vaginal, parenteral, topical, intravenous or other mode of administration. The pharmaceutical formulation contains a compound of the invention in combination with one or more pharmaceutically acceptable ingredients. The carrier may be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration.

In the preparation of pharmaceutical formulations containing the siRNA-complex of the present invention in the form of dosage units for oral administration the compound selected may be mixed with solid, powdered ingredients, such as lactose, saccharose, sorbitol, mannitol, starch, arnylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatin capsules may be prepared with capsules containing a mixture of the active compound or compounds of the invention in vegetable oil, fat, or other suitable vehicle for soft gelatin capsules. Hard gelatin capsules may contain granules of the active compound. Hard gelatin capsules may also contain the siRNA-complex including the target moiety and the RNA-binding moiety as well as the target siRNA in combination with solid powdered ingredients such as lactose, saccharose, sorbitol, mannitol, potato starch, corn starch, arnylopectin, cellulose derivatives or gelatin.

Dosage units for rectal or vaginal administration may be prepared (i) in the form of suppositories which contain the active substance, i.e. the siRNA-complex, mixed with a neutral fat base; (ii) in the form of a gelatin rectal capsule which contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol. If desired, such liquid preparations may contain coloring agents, flavoring agents, saccharin and carboxymethyl cellulose or other thickening agents. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

The methods of the present invention to deliver RNA interference can also be used to deliver RNA interference orally in granular form including sprayed dried particles, or complexed to form micro or nanoparticles.

The subject or individual as referred to herein and throughout the specification includes mammals, such as murine, specifically mice and rats, bovine, and primates, such as human.

The in vivo delivery as used herein means delivery of the siRNAs into a living subject, including human.

The in vitro delivery as used herein means delivery of siRNAs into cells and organs outside a living subject.

The invention also provides a method for screening targets of pharmaceutical intervention comprising the steps of delivering a plurality of different siRNAs into cells in parallel cell culture environments using a fusion protein comprising a target moiety and an siRNA binding moiety that is mixed with the specific different siRNAs, and measuring the effects of silencing the siRNA targeted genes. The measurement of effects can be performed either by detecting target RNA molecules using traditional Northern blot analysis or more quantitative methods such as RT-PCR-based RNA quantification or other RNA quantification methods well known to one skilled in the art. Alternatively, silencing can be detected using traditional immunohistochemical methods to determine presence and/or absence of the protein produced by the target RNA.

The references cited throughout the specification are herein incorporated by reference in their entirety.

EXAMPLES

Example 1

Recent studies have demonstrated a promising therapeutic potential of duplex small interfering RNAs (siRNA) in prevention and treatment of infectious disease, cancer and neurodegenerative disease in vitro. However, the major hurdle in therapeutic application of siRNA is how to steer the molecule into a desired cell population to achieve maximal therapeutic effect and avoid non-specific silencing or other toxicity in bystander cells.

Since duplex siRNAs cannot choose their own cellular targets, it is necessary to design a "guiding missile" to deliver the molecules. Cell surface receptors have been explored as potential targets for gene delivery. A fusion protein composed of a human single-chain antibody fragment (ScFv) at the N-terminus with full length or truncated human protamine polypeptide at the C-terminus can bind RNA and deliver it into target cells expressing the corresponding cell surface protein recognized by the antibody (US 2004/0023902). Alternatively, the fusion protein can be generated from separate heavy and light chains with the C-terminus of the heavy chain fused to protamine or a fragment of protamine.

We used the following siRNA and protamine constructs:

(SEQ ID NO: 1)
GCGGCCGCACGCAGCCAGAGCCGGAGCAGATATTACCGCCAGAGACAAAG

AAGTCGCAGACGAAGGAGGCGGAGCTGCCAGACACGGAGGAGAGCCATGA

GATCTCATCATCACCACCACCATTAA.

Nucleic acids encoding the targeting moiety. We used protamine or fragments thereof:

(SEQ ID NO: 2)
GCGGCCGCAATGGCCAGGTACAGATGCTGTCGCAGCCAGAGCCGGAGCAG

ATATTACCGCCAGAGACAAAGAAGTCGCAGACGAAGGAGGCGGAGCTGCC

AGACACGGAGGAGAGCCATGAGATCTCATCATCACCACCACCATTAA;

(SEQ ID NO: 3)
GCGGCCGCACGCAGCCAGAGCCGGAGCAGATATTACCGCCAGAGACAAAG

AAGTCGCAGACGAAGGAGGCGGAGCTGCCAGACACGGAGGAGAGCCATGA

GGTGTTGTCGCCCCAGGTACAGACCGAGATGTAGAAGACACAGATCTCAT

CATCACCACCACCATTAA;

(SEQ ID NO: 4)
GCGGCCGCACGCAGCCAGAGCCGGAGCAGATATTACCGCCAGAGACAAAG

AAGTCGCAGACGAAGGAGGCGGAGCAGATCTCATCATCACCACCACCATT

AA;

(SEQ ID NO: 5)
GCGGCCGCCGGCGGAGGAGGATCTCATCATCACCACCATTAA;

(SEQ ID NO: 6)
GCGGCCGCAATGGCCAGGTACAGATGCTGTCGCAGCCAGAGCCGGAGCAG

ATATTACCGCCAGAGACAAAGAAGTCGCAGACGAAGGAGGCGGAGCAGAT

CTCATCATCACCACCACCATTAA.

The results shown were obtained using the full length protamine conjugated with gp160 antibody (F105-P).

In our present study, we adapted this system to determine if the antibody-protamine fusion protein could specifically and effectively deliver siRNAs into cells via cell surface receptors. The same idea can in principle be modified to design fusion proteins with receptor ligands substituting for antibodies. As proof of principle, we used a modified antibody protein (F105-protamine) composed of the light chain and modified heavy chain from a human antibody recognizing HIV gp120 (F105) to target siRNAs to HIV-infected cells or to cells transfected to express HIV gp160. The antibody heavy chain was fused at the C-terminus to full-length protamine. We have been able to show that the fusion protein complexed to siRNA efficiently and specifically delivers siRNA into infected, but not uninfected, cells; the targeting is highly efficient; and delivered siRNA can silence specific mRNA. Moreover, these delivered siRNAs inhibit HIV replication.

Using the described delivery method, we successfully tested the following siRNAs to inhibit gene expression:

C-myc #1: 5-GAACAUCAUCAUCCAGGAC-3 (sense, SEQ ID NO: 13); CUUGUAGUAGUAGGUCCUG (antisense, SEQ ID NO: 14, FEBS Lett. 2004 Feb. 27; 560(1-3): 210-4);

C-myc #2: 5-ACUCGAACAGCUUCGAAAC-3 (sense, SEQ ID NO: 15); UGAGCUUGUCGAAGCUUUG (antisense, SEQ ID NO: 16, Id)

VEGF: 5-CGAUGAAGCCCUGGAGUGC-3 (sense, SEQ ID NO: 17); GCACUCCAGGGCUUCAUCG (antisense, SEQ ID NO: 18, Mol Vis. 2003 May 30; 9: 210-6).

MDM2: 5'GCUUCGGAACAAGAGACUCdTdT (sense, SEQ ID NO: 7); 3'dTdTGGUUGUGACGAAUGCGAAU (antisense, SEQ ID NO: 8);

Apex1: 5'-CCAACACUGCUUACGCUUAdTdT-3' (sense, SEQ ID NO: 9); 3'-dTdTGGUUGUGACGAAUGCGAAU (antisense, SEQ ID NO: 10);
and pp32: 5'-AAGAAGCUUGAAUUAAGCGdTdT-3' (sense, SEQ ID NO: 11); 3'-dTdTUUCUUCGAACUUAAUUCGC-5' (antisense, SEQ ID NO: 12).

Protein purification. The fusion protein is expressed in COS cells from a bicistronic plasmid and purified over an L-protein column that binds the light chain of human immunoglobulin. COS cells were transfected stably with F105 or F105-protamine expressing plasmids (PCMV-F105, pCMV-F105-protamine). Supernatants were collected from the stably transfected COS cells and F105 or F105-P were purified by passing the supernatants through an L-protein column. The protein could be eluted from the column as a single specific peak and yielded a band corresponding to 55 kDa in nonreducing gels, identical in size to F105 or F105-P. In reducing gels, two proteins of approximately 22 and 25 kDa, corresponding to the light and the heavy chain of the antibody, were seen. We also confirmed the identity of the proteins by Western Blot analysis probed with human Fab or protamine antibodies.

Binding capacity to siRNA. We then evaluated whether F105-P can bind siRNA by immunoprecipitating F105-P pre-incubated with FITC-labeled siRNA using protein A,G beads complexed with anti-protamine antibody.

F105-P was mixed with the beads at doubling dilutions starting from 30 pmol up to 0.9375 pmol and rotated at 4 degree for overnight. FITC-siRNA (200 pmol) was added to the mixture, and rotated for another 1 hr. and then washed thoroughly. To determine the ratio of siRNA carried by F105-P, the absorbance values for the bound siRNA at different concentrations of F105-P was determined on a spectrophotometer and plotted against the standard curve. About 5% of the loaded siRNA could be recovered after co-precipitation with the fusion protein, suggesting that F105-P can concentrate siRNA. The molar ratio of F105-P to siRNA required for optimal binding was found to be 1:6 which was used in all experiments evaluating functional silencing by svFv-delivered siRNA (FIG. 1).

Figure 3:
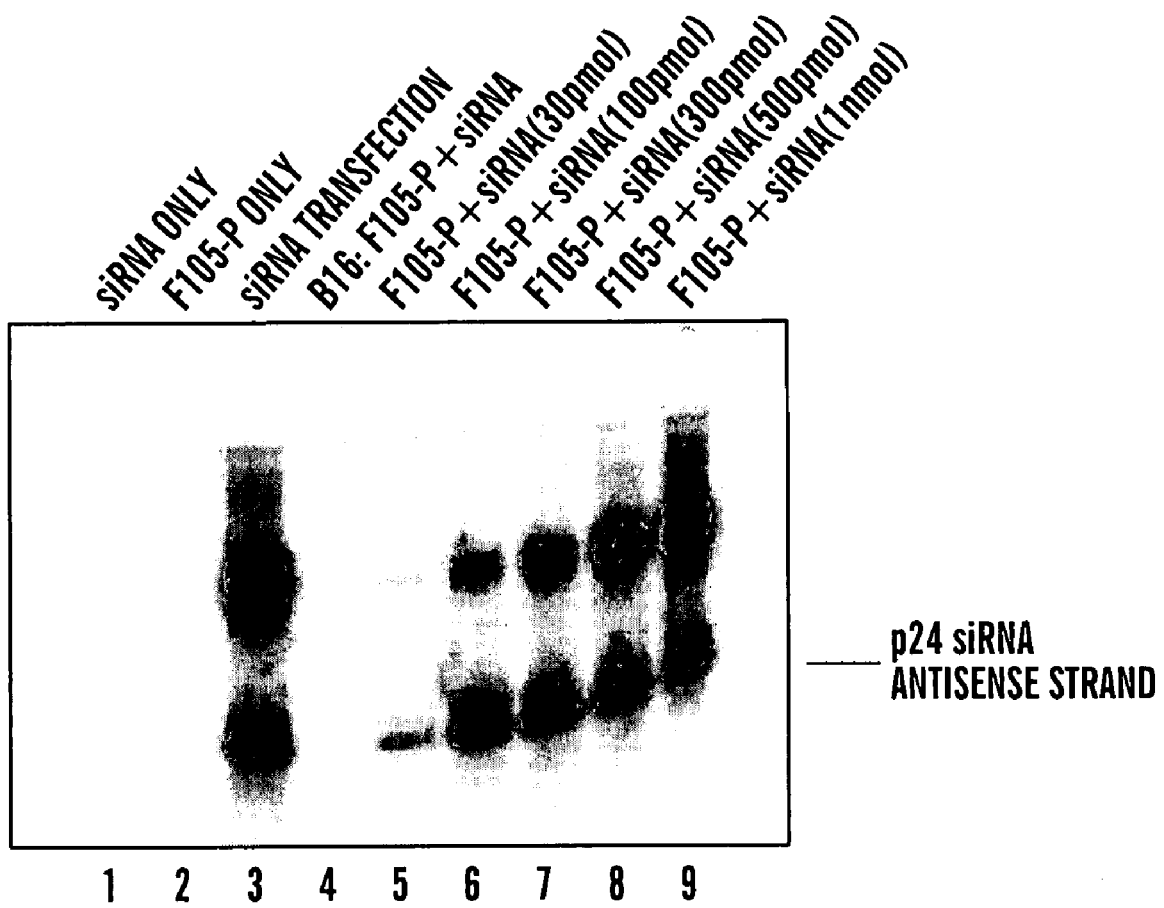
FIG. 3 shows that F105-protamine delivers siRNA into gp160 stably transfected B16 cells. Mouse melanoma B16 cells were transfected stably with gp160, and treated with siRNA alone, F105-P alone, transfected with siRNA, or F105-P complexed with different amounts of siRNA at a molar ratio of 1:6. Untransfected B16 cells not expressing the gp160 receptor serve as control (lane 4). Two days after treatment, cells were harvested and RNA was extracted for modified Northern blotting.

Targeting siRNA into mouse melanoma cells expressing gp160. Mouse melanoma B16 cells were transfected stably with gp160, and treated with siRNA alone, F105-P alone, transfected with siRNA, or F105-P complexed with different amount of siRNA at a molar ratio of 1:6. Untransfected B16 cells not expressing the gp160 receptor serve as control (lane 4). Two days after treatment, cells were harvested and RNA was extracted for modified Northern blotting (FIG. 3).

Figure 2A:
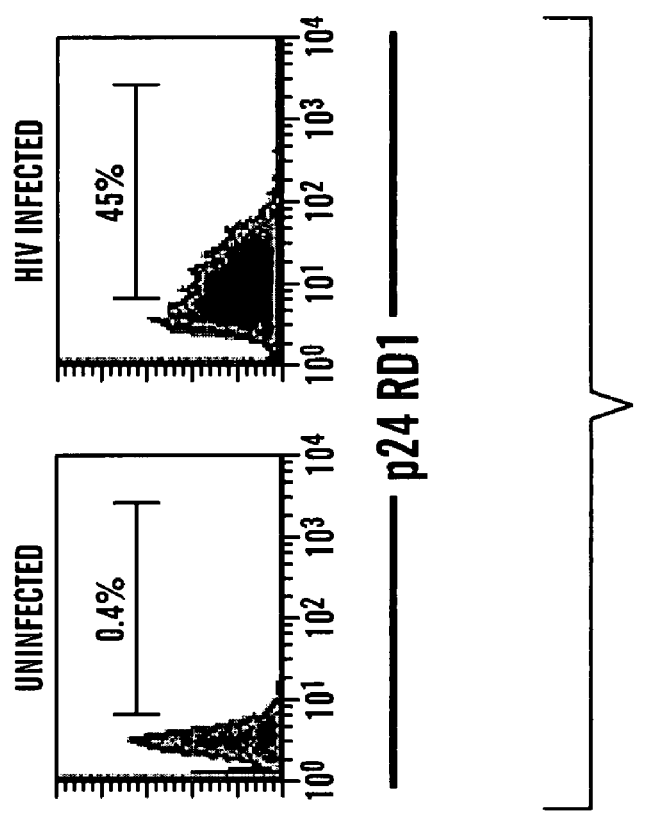
FIGS. 2A-2B demonstrate that F105-protamine delivers siRNA only into infected Jurkat cells.
Figure 2B:
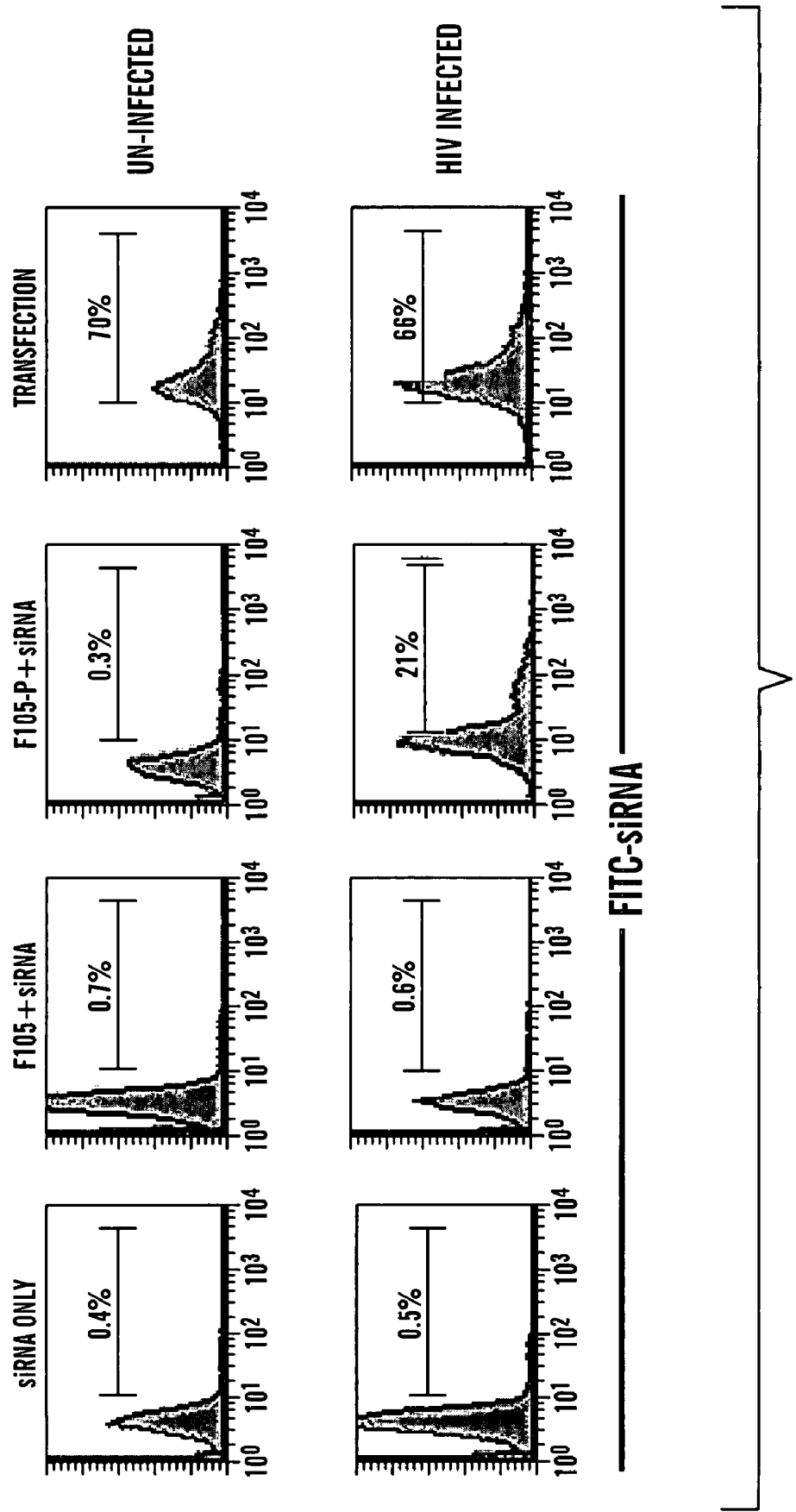

Targeting siRNA to HIV-infected cells. Next, we evaluated whether F105-P can deliver siRNA into target HIV-infected cells. Jurkat cells were infected with HIV$_{IIIB}$, with 40% of the cells infected by intracellular p24 staining after 48 hr. Cells were then treated with F105-P mixed with FITC-CD4 siRNA at a molar ratio of 1:6. Twenty-four hours after treatment, 21% of the cells took up the labeled siRNA. (FIG. 2)

To determine whether siRNA delivered by F105-P can effectively silence target genes, HeLa-GFP cells were transfected with HIV HXB.2 plasmid and exposed to F105-P bound to siRNA targeting GFP. GFP expression was reduced approximately 5 fold in cells expressing p24, while untransfected and uninfected cells did not show any reduction in GFP expression. Similarly, GFP expression was unchanged in controls where F105 alone, GFP-siRNA alone, or F105-P mixed with an irrelevant siRNA (mouse Fas siRNA) were used.

Figure 4:
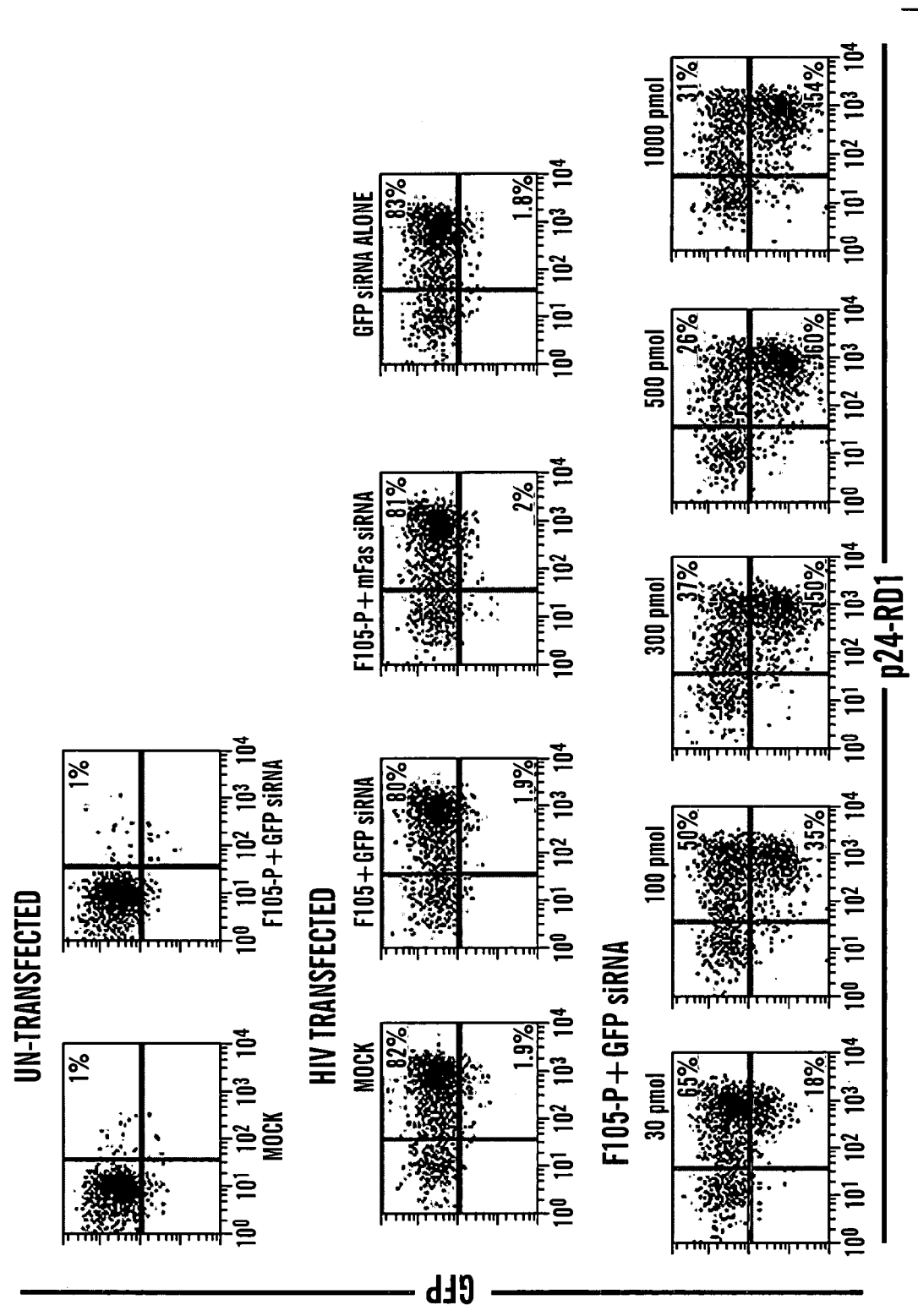
FIG. 4 shows that GFP-siRNA delivered by F105-protamine silences GFP expression. HeLa-GFP cells were transfected with HIV HXB plasmid DNA for two days and then treated with GFP siRNA alone, F105-protamine alone, F105 plus GFP-siRNA, F105-protamine plus control mouse Fas-siRNA, or F105-protamine loaded with various amounts of GFP siRNA. GFP expression is silenced only in infected cells, which stain for intracellular HIV p24, treated with GFP-siRNA complexed with F105-protamine. Silencing is dose-dependent and plateaus at about 300-500 pmol siRNA.

We also showed that GFP-siRNA delivered by F105-protamine silences GFP expression (FIG. 4). HeLa-GFP cells were transfected with HIV HXB plasmid DNA for two days and then treated with GFP siRNA alone, F105-protamine alone, F105 plus GFP-siRNA, F105-protamine plus control mouse Fas-siRNA, or F105-protamine loaded with various amount of GFP siRNA. GFP expression is silenced only in infected cells, which stain for intracellular HIV p24, treated with GFP-siRNA complexed with F105-protamine. Silencing is dose-dependent and plateaus at about 300-500 pmol siRNA. (FIG. 4)

Figure 5:
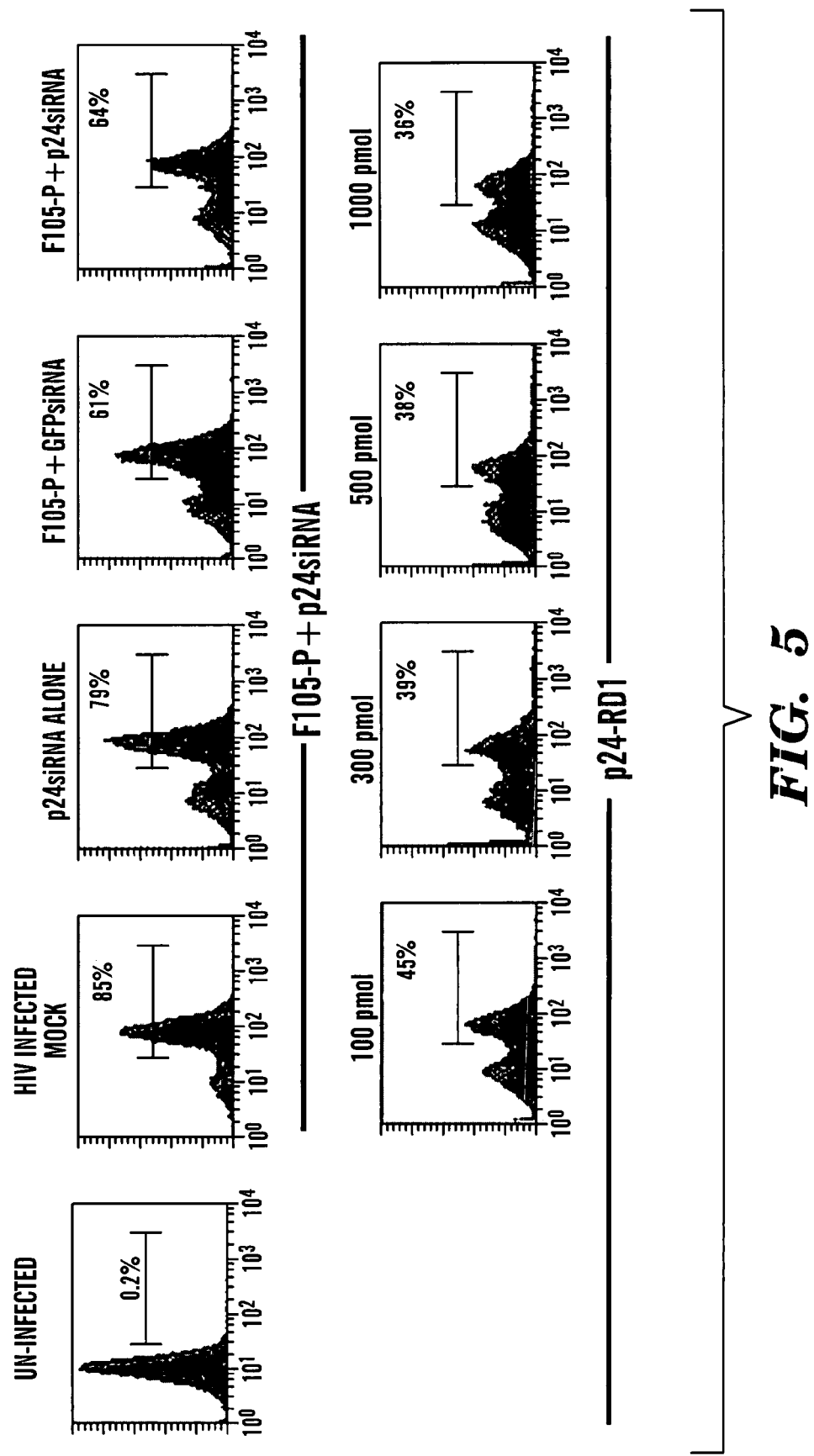
FIG. 5 shows that HIV replication is inhibited in primary CD4 cells treated with F105-protamine to deliver HIV gag-siRNA. Cultures in which 60-85% of activated CD4 T cells were infected with HIV (assessed by intracellular p24 staining) were mock-treated or treated with p24-siRNA alone, F105-protamine (F105-P) plus GFP-siRNA, F105 plus p24-siRNA, or F105-protamine plus p24-siRNA at the indicated concentrations. Cultures were evaluated 2 days later for intracellular p24 staining. HIV infection was reduced only in cells treated with F105-protamine complexed with p24-sRNA. About 40% of the treated cells had detectable p24 staining, compared to 61-85% of control cells.

To determine whether F105-P-mediated siRNA delivery can reduce replication of HIV, we infected PHA-activated primary CD4 T cells with $HIV_{IIIB}$. Primary T cells are difficult to transfect with siRNAs using conventional methods. When most of the cells became productively infected (77% of the cells stained for HIV p24), the cells were exposed to F105-complexed to HIV gag-siRNA. Control cells had modest reductions in HIV p24 expression compared to mock-treated cells (61-79% vs 85% p24+), but HIV replication above background was detected in only 36-45% of cells after treatment with gag-siRNA delivered by F105-protamine. FIG. 5 shows that HIV replication is inhibited in primary CD4 cells treated with F105-protamine to deliver HIV gag-siRNA. Cultures in which 60-85% of activated CD4 T cells were infected with HIV (assessed by intracellular p24 staining) were mock-treated or treated with p24-siRNA alone, F105-protamine (F105-P) plus GFP-siRNA, F105 plus p24-siRNA, or F105-protamine plus p24-siRNA at the indicated concentrations. Cultures were evaluated 2 days later for intracellular p24 staining. HIV infection was reduced only in cells treated with F105-protamine complexed with p24-sRNA. About 40% of the treated cells had detectable p24 staining, compared to 61-85% of control cells.

Figure 6A:
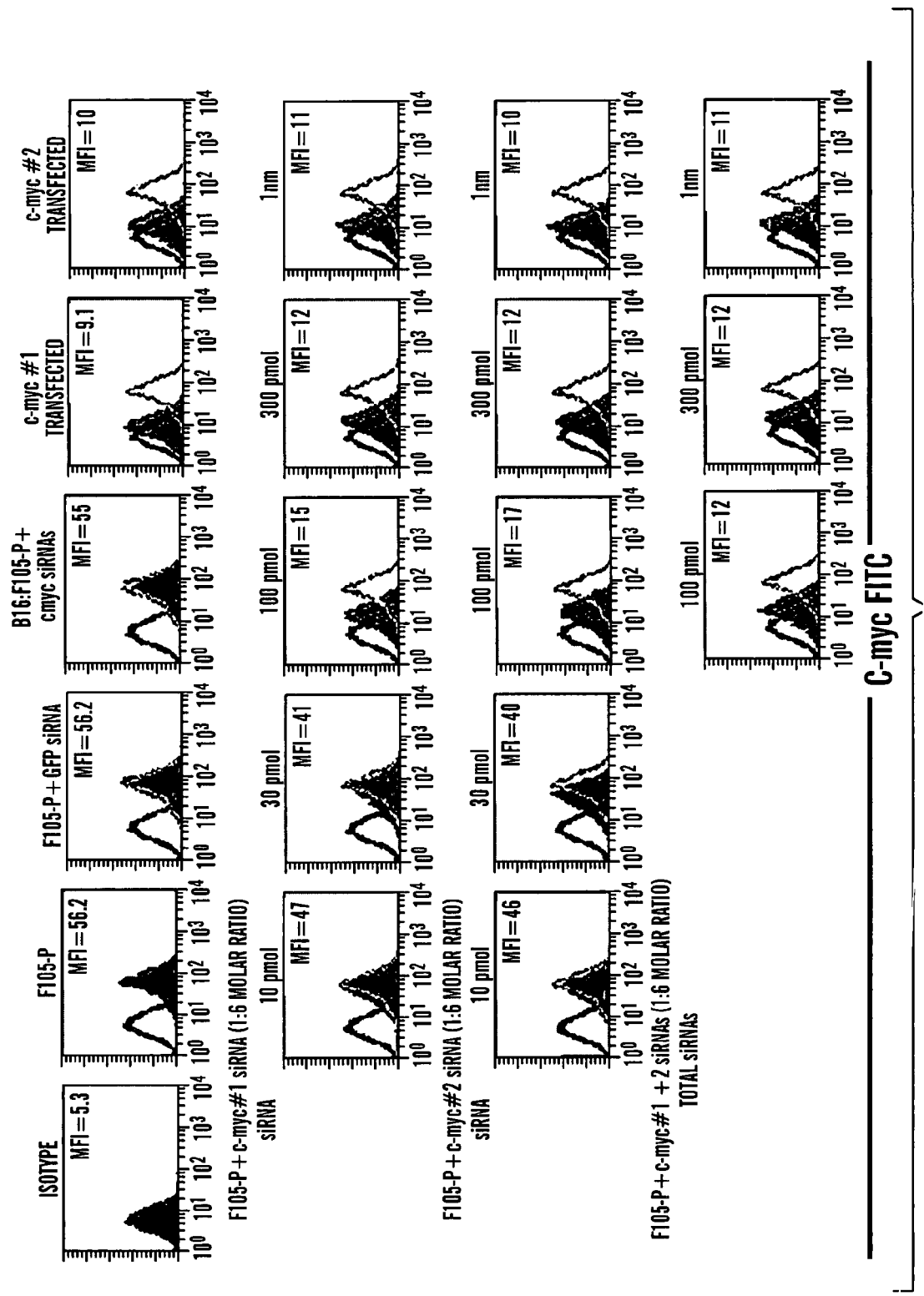
FIGS. 6A-6B show that c-myc siRNAs and VEGF siRNA delivered by F105-protamine silence target gene expression. Mouse melanoma B16 cells were transfected stably with gp160 plasmid DNA and then treated with F105-protamine alone, F105-protamine plus control GFP-siRNA, or F105-protamine loaded with various amounts of c-myc siRNAs (FIG. 6A) or VEGF siRNA (FIG. 6B). B16 cells without gp160 expression were used as a control for F105-P delivery. c-myc (FIG. 6A) or VEGF (FIG. 6B) expression is silenced in gp160-B16 cells, treated with corresponding siRNA complexed with F105-protamine. Silencing is dose-dependent and plateaus at about 300 pmol siRNA.
Figure 6B:
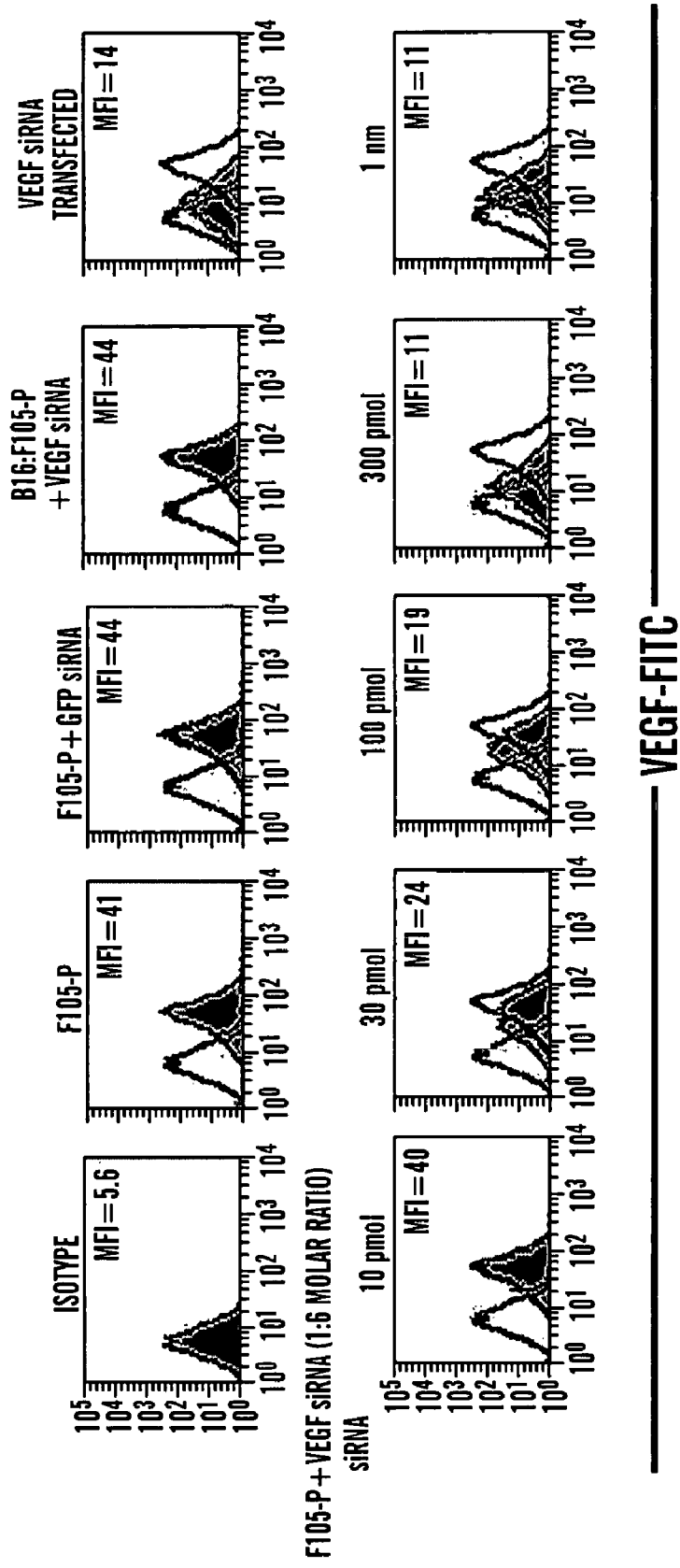

We showed that c-myc siRNAs (FIG. 6A) and VEGF siRNA (FIG. 6B) delivered by F105-protamine silence target gene expression. Mouse melanoma B16 cells were transfected stably with gp160 plasmid DNA and then treated with F105-protamine alone, F105-protamine plus control GFP-siRNA, or F105-protamine loaded with various amount of c-myc siRNAs (FIG. 6A) or VEGF siRNA (FIG. 6B). B16 cells without gp160 expression were used as a control for F105-P delivery. c-myc (FIG. 6A) or VEGF (FIG. 6B) expression is silenced in gp160-B16 cells, treated with corresponding siRNA complexed with F105-protamine. Silencing is dose-dependent and plateaus at about 300 pmol siRNA.

Figure 7A:
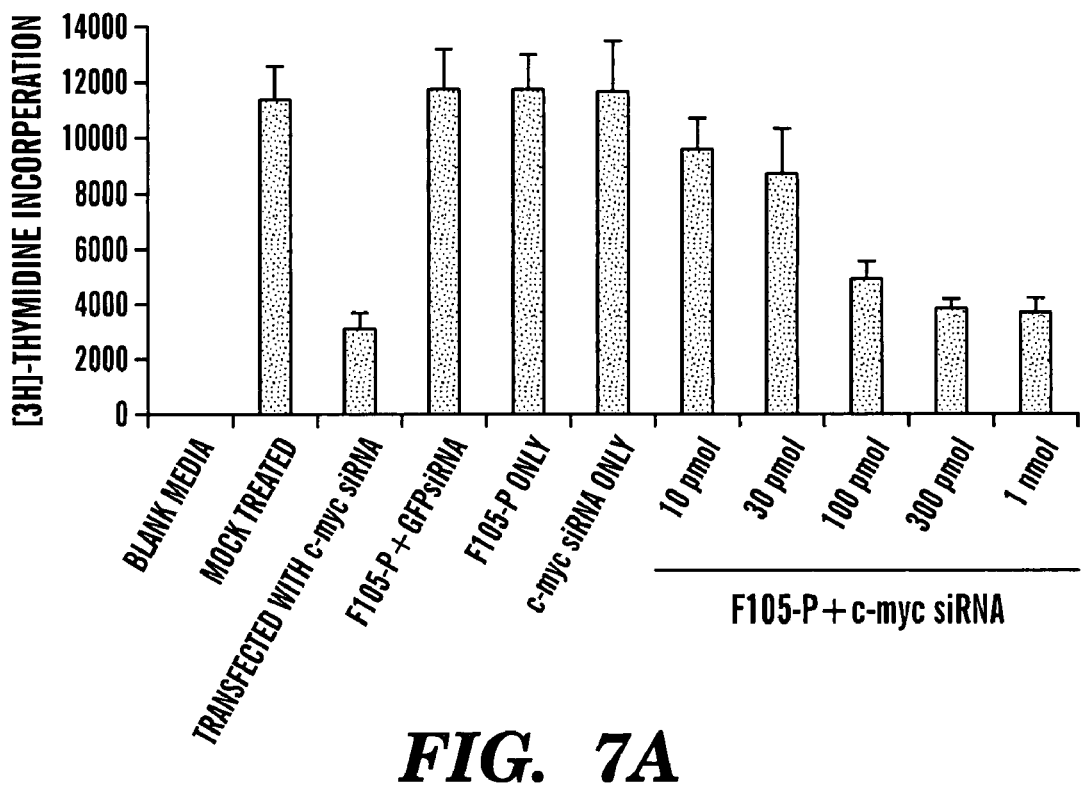
FIGS. 7A-7F show that tumor proliferation is inhibited in mouse melanoma B16 cells stably expressing gp160 treated with F105-protamine to deliver siRNAs targeting tumor specific genes. Gp160 expressing B16 cells were untreated, treated with F105-Protamine alone, F105-Protamine plus GFP-siRNA (1 nmol) (FIGS. 7A-7D, 7F), c-myc-siRNA (1 nmol) (FIG. 7A), mdm2-siRNA (1 nmol) (FIG. 7B), VEGF-siRNA (1 nmol) (FIG. 7C) or pp32-siRNA (1 nmol)(FIG. 7D) alone, or F105-Protamine loaded with various amount of c-myc-siRNAs (FIG. 7A), mdm2-siRNA (FIG. 7B), VEGF-siRNA (FIG. 7C), pp32-siRNA (FIG. 7D) individually or in combination (FIG. 7F) (numbers in bracket represent the siRNA amount in pmol). Cultures were evaluated 2 days later for cell growth using [$^3$H]-thymidine incorporation assay. Parent B16 cells lacking gp160 expression, untreated, or treated with F105-Protamine alone or F105-Protamine loaded with 1 mmol of c-myc-siRNA, mdm2-siRNA, VEGF-siRNA, pp32-siRNA, or GFP-siRNA, were used as a control (FIG. 7E). pp32 is used as a negative control, since it has been reported to be a tumor suppressor gene.
Figure 7B:
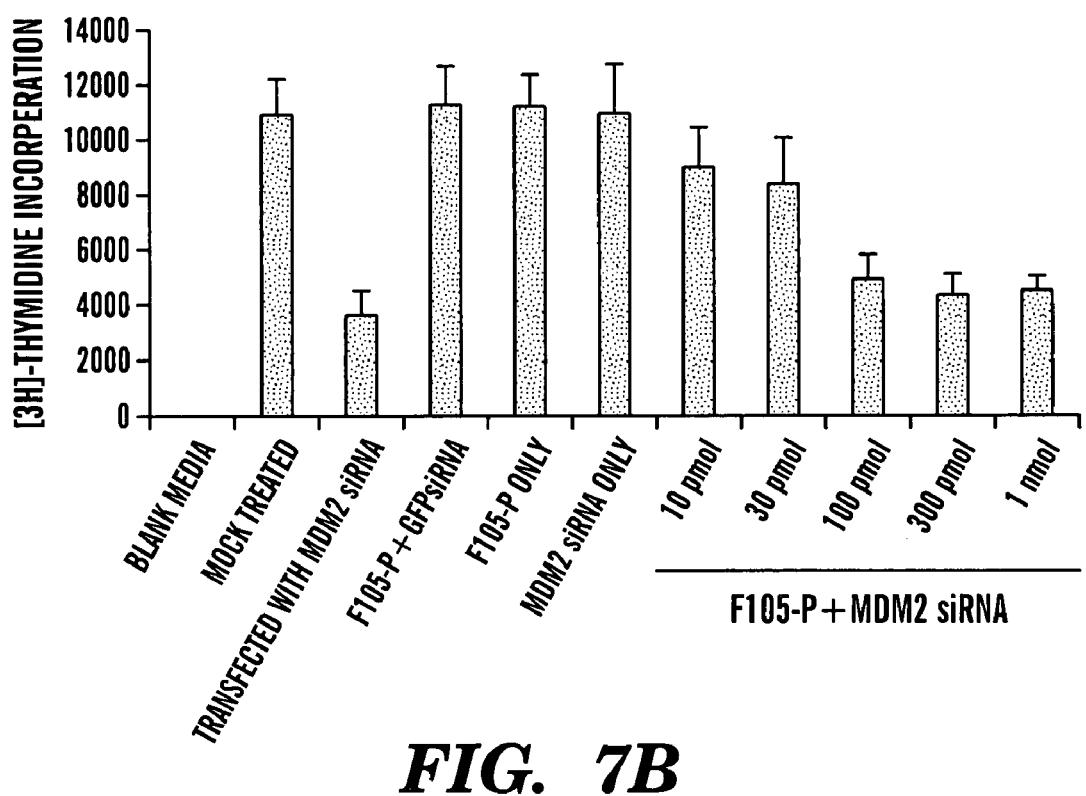
Figure 7C:
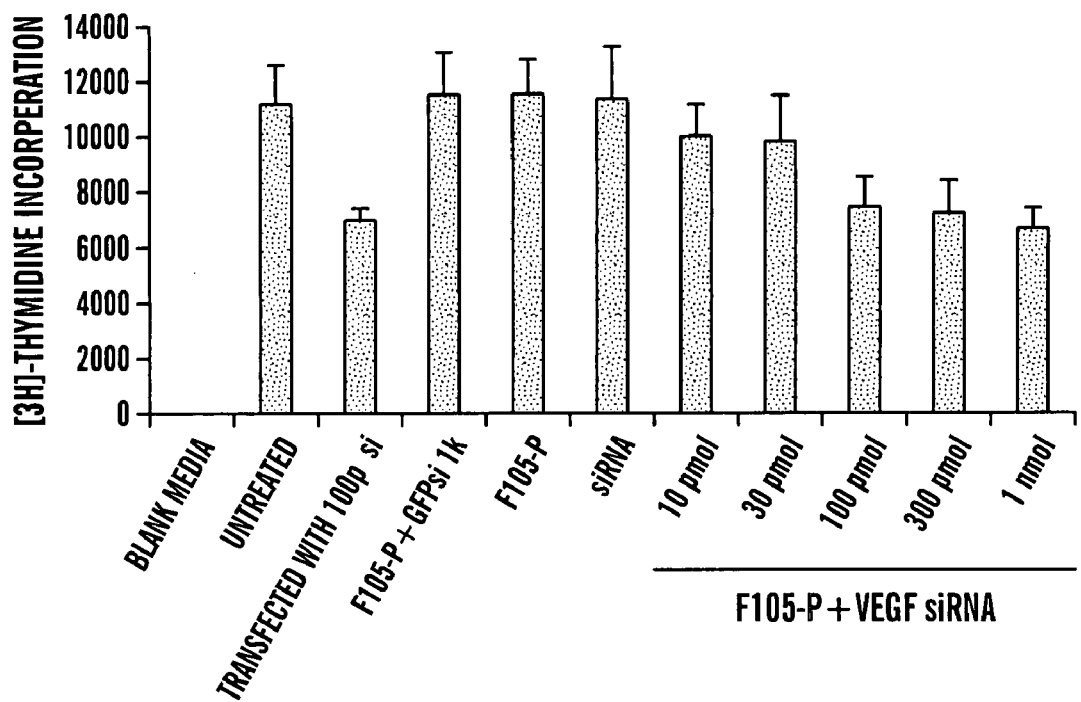
Figure 7D:
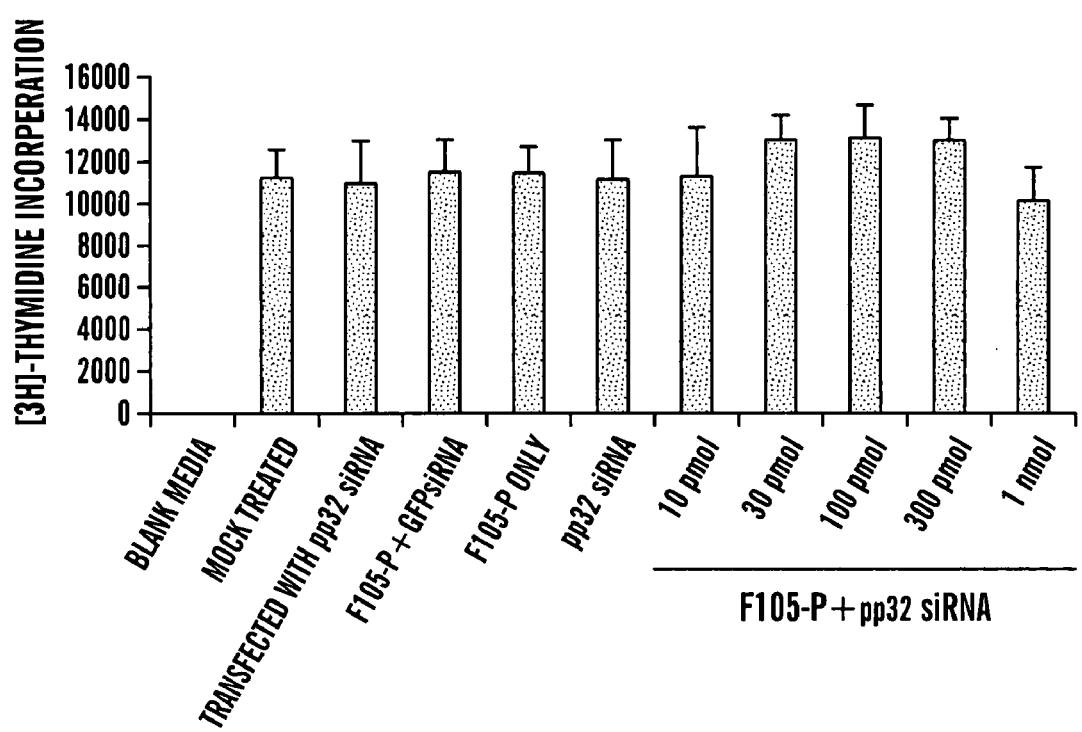
Figure 7E:
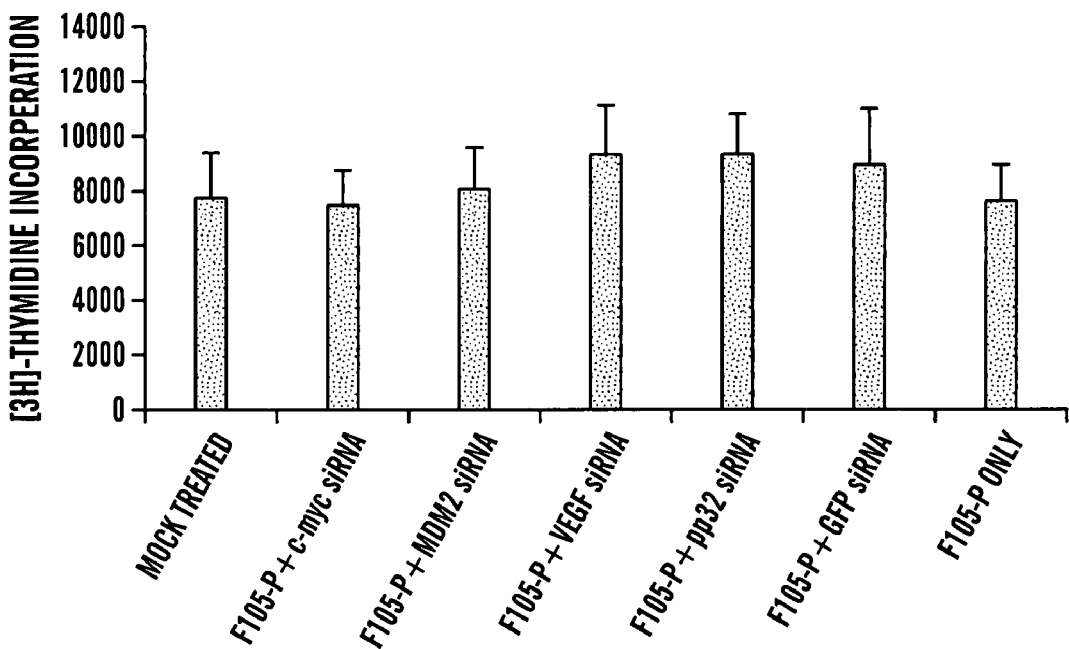
Figure 7F:
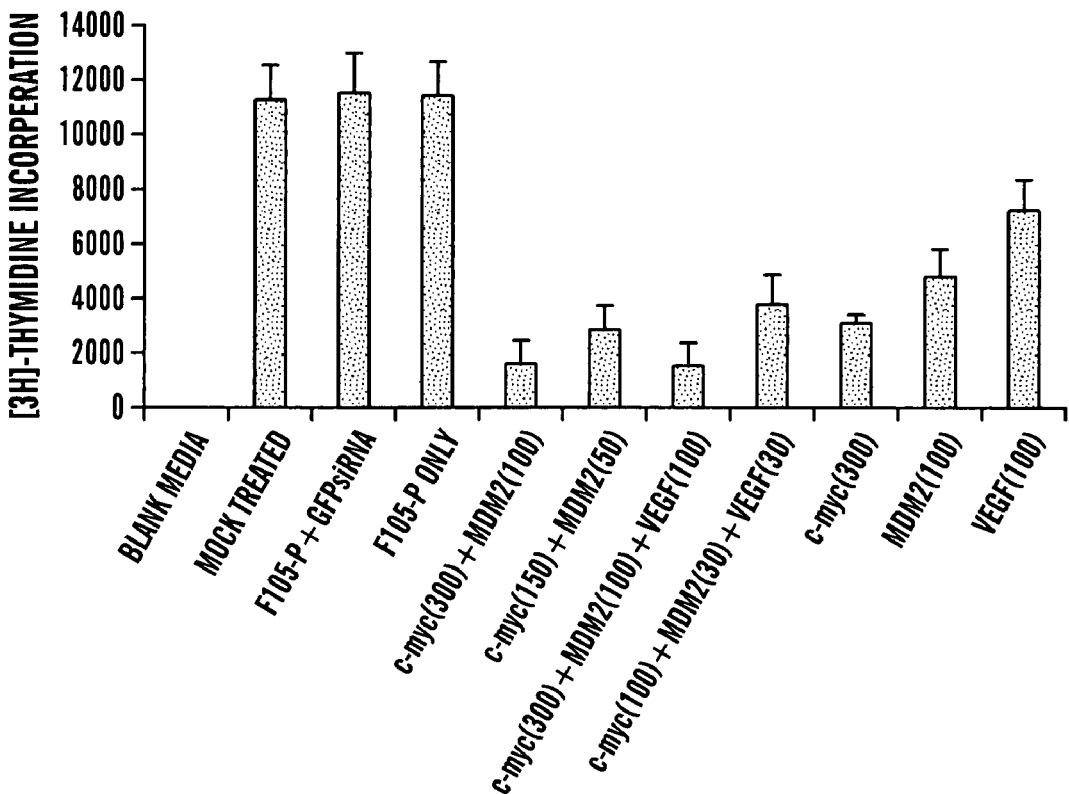

We showed that tumor proliferation is inhibited in mouse melanoma B16 cells stably expressing gp160 treated with F105-protamine to deliver siRNAs targeting tumor specific genes. Gp160 expressing B16 cells were untreated, treated with F105-Protamine alone, F105-Protamine plus GFP-siRNA (1 nmol) (FIGS. 7A-7D, 7F), c-myc-siRNA (1 nmol) (FIG. 7A), mdm2-siRNA (1 nmol) (FIG. 7B), VEGF-siRNA (1 nmol) (FIG. 7C) or pp32-siRNA (1 nmol)(FIG. 7D) alone, or F105-Protamine loaded with various amount of c-myc-siRNAs (FIG. 7A), mdm2-siRNA (FIG. 7B), VEGF-siRNA (FIG. 7C), pp32-siRNA (FIG. 7D) individually or in combination (FIG. 7F) (numbers in bracket represent the siRNA amount in pmol). Cultures were evaluated 2 days later for cell growth using [$^3$H]-thymidine incorporation assay. Parent B16 cells lacking gp160 expression, untreated, or treated with F105-Protamine alone or F105-Protamine loaded with 1 nmol of c-myc-siRNA, mdm2-siRNA, VEGF-siRNA, pp32-siRNA, or GFP-siRNA, were used as a control (FIG. 7E). pp32 was used as a negative control, since it has been reported to be a tumor suppressor gene.

Figure 8A:
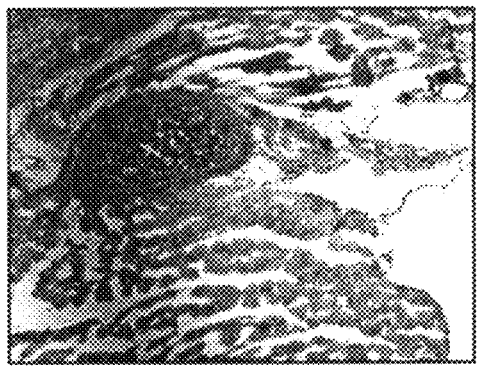
FIGS. 8A-8F show that F105-Protamine delivers siRNA into gp160-positive B16 tumors in mice. Gp160 stably expressing B16 melanoma cells were inoculated subcutaneously into the right flanks of C57/B6 mice at 1×10$^6$ cells per mouse. Nine days later, F105-P (FIGS. 8C, 8D) or oligofectamine (FIGS. 8E, 8F) loaded with FITC-labeled siRNA was injected into the tumor tissue, and tumors were harvested after 16 hr for fluorescence microscopy. Hematoxylin/Eosin (HE) staining indicated inoculated tumor nests (FIGS. 8A, 8B). F105-P specifically delivers FITC-siRNA into gp160-B16 tumor tissue while oligofectamine delivers FITC-siRNA into both tumor and neighboring tissues surrounding the tumor nest.
Figure 8B:
Figure 8C:
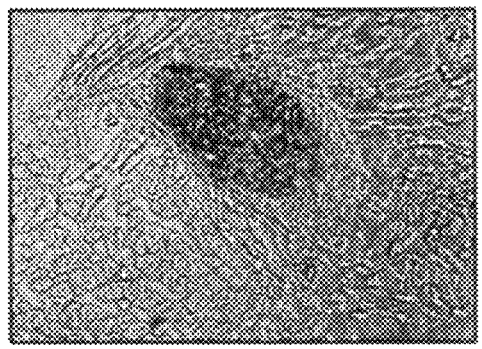
Figure 8D:
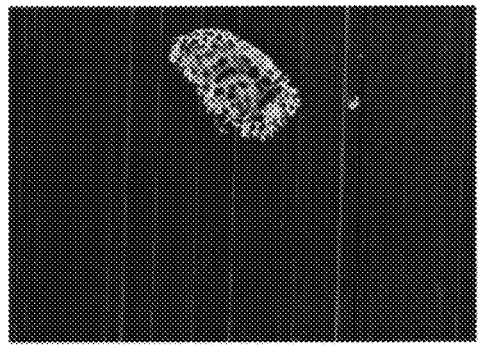
Figure 8E:
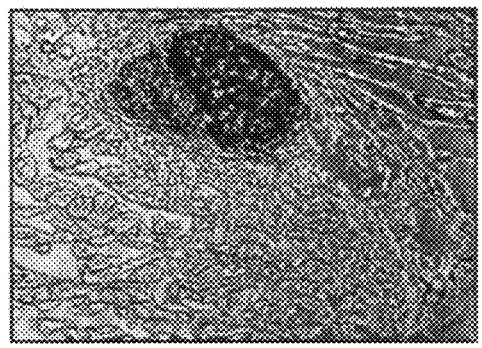
Figure 8F:
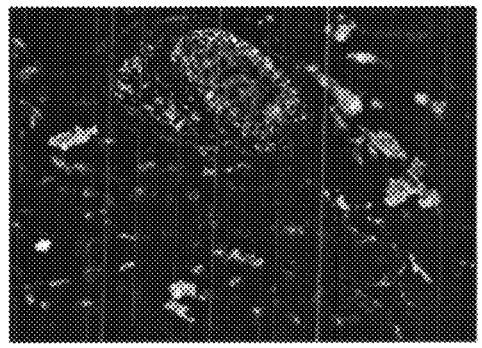

We showed that F105-Protamine delivers siRNA into gp160-positive B16 tumors in mice. Gp160 stably expressing B16 melanoma cells were inoculated subcutaneously into the right flanks of C57/B6 mice at $1 \times 10^6$ cells per mouse. Nine days later, F105-P (FIGS. 8C, 8D) or oligofectamine (FIGS. 8E, 8F) loaded with FITC-labeled siRNA was injected into the tumor tissue, and tumors were harvested after 16 hr for fluorescence microscopy. HE staining indicated inoculated tumor nests (FIGS. 8A, 8B). F105-P specifically delivers FITC-siRNA into gp160-B16 tumor tissue while oligofectamine delivers FITC-siRNA into both tumor and neighboring tissues surrounding the tumor nest.

Example 2

Figure 9A:
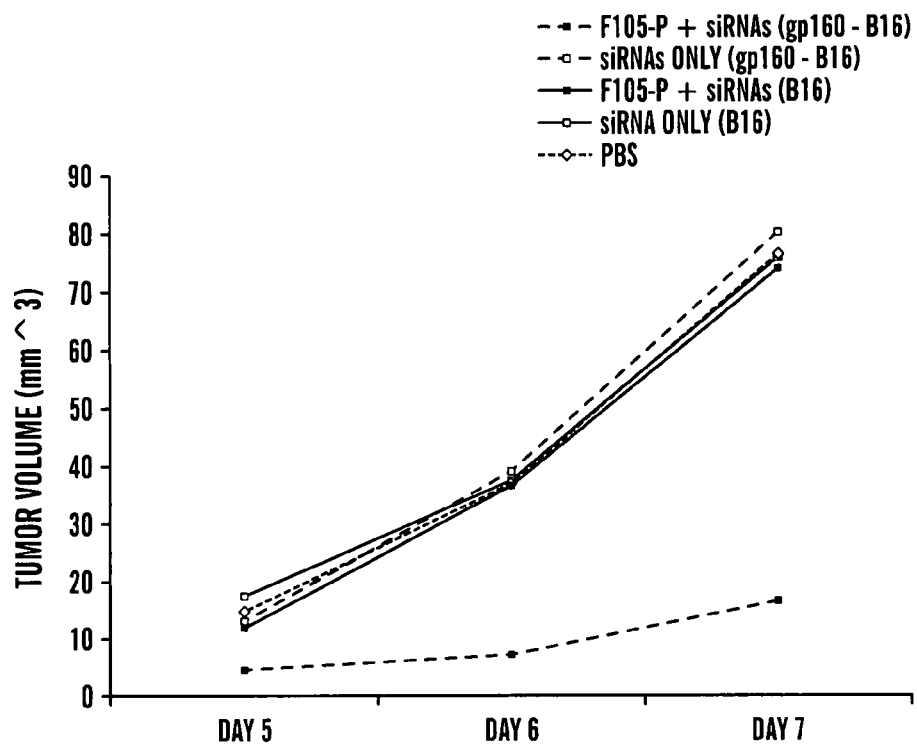
FIGS. 9A-9B show that F105-P delivers c-myc, MDM2 and VEGF siRNAs into gp160-B16 tumors in vivo by intratumoral (FIG. 9A) and intravenous (FIG. 9B) injection and reduces tumor growth. Mouse melanoma B16 cells engineered to express gp160 stably were inoculated subcutaneously (s.c.) into the right flank of C57/BL6 mice at $5 \times 10^6$ cells per mouse. On day 0, 1, and 3 after cell inoculation, mice were injected s.c.
Figure 9B:
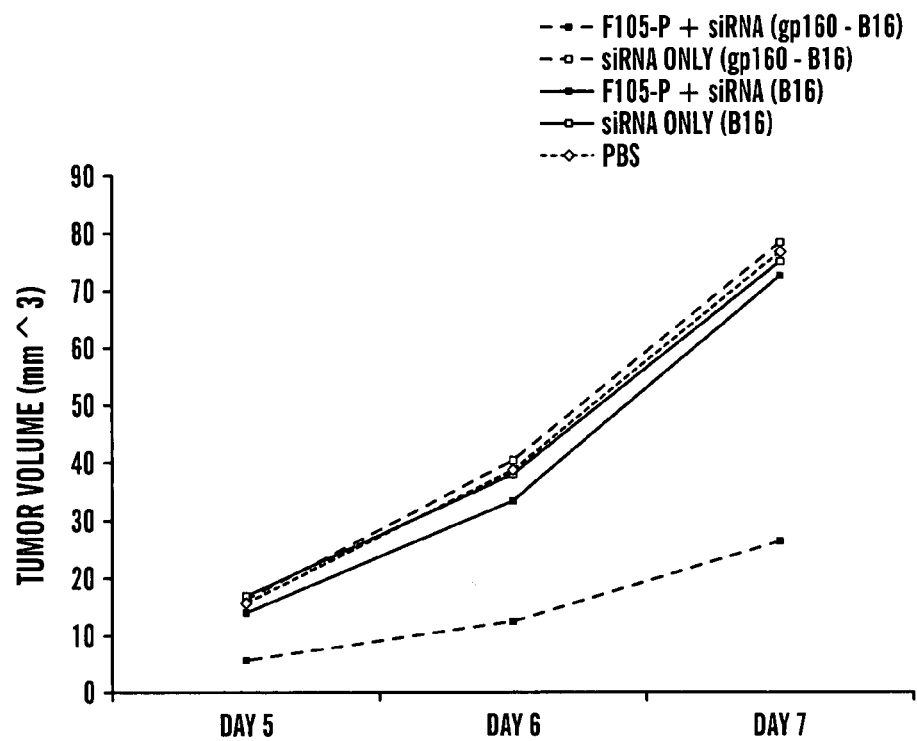

We evaluated the feasibility of applying F105-protamine to deliver siRNA into specific cell population not only in vitro but also in vivo. This evaluation was performed in a melanoma mouse model, but any other model animal could have been used for this first step evaluation, and the results are readily applicable to, for example, delivering siRNAs to humans in need of specifically targeted gene silencing. FIGS. 9A and 9B show that F105-P delivers c-myc, MDM2 and VEGF siRNAs into gp160-B16 tumors in vivo by intratumoral (FIG. 9A) and intravenous (FIG. 9B) injection and reduces tumor growth.

We engineered mouse melanoma B16 cells to express gp160 stably and inoculated them subcutaneously (s.c.) into the right flank of C57/BL6 mice at $5 \times 10^6$ cells per mouse. On day 0, 1, and 3 after cell inoculation, mice were injected s.c. (FIG. 9A) into the right flank, where the tumor cells were implanted, or i.v. (FIG. 9B) with either a combination of siRNA (2 duplexes of c-myc siRNA, mdm2 siRNA and VEGF siRNA at 20 µg/duplex) complexed with F105-P at 6:1 molar ratio, or with siRNAs alone or PBS at a volume of 100 µl. Tumor size was followed daily from day 5 after inoculation. Parental B16 cells not expressing gp160 were not inhibited.

Our results showed that both tumor size and tumor weight in mice treated with siRNA complexed with F105-P were smaller as compared to the controls.

Therefore, our results show that F105-P enhances in vivo delivery of siRNA into gp160 positive cells. These data demonstrate that the F105-P system is an effective way of delivering functional siRNA into cells both in vitro and in vivo. This novel delivery system has broad implications for targeted delivery of siRNA into, for example, human cells. Because of the possibility to target the inhibitory RNAs into a specific population of cells, the occurrence of undesired side effects can be minimized and the effectiveness of the treatment enhanced.

Example 3

Materials and Methods siRNAs siRNAs were synthesized using 2'-O-ACE-RNA phosphoramidites (A4 grade, Dharmacon Research). siRNAs directed against fas and EGFP were as previously described[6]. The sense and anti-sense strands of siRNAs were:

```
c-myc #1²⁷:5 -GAACAUCAUCAUCCAGGAC-3' (sense, SEQ
ID NO: 13);

3'-CUUGUAGUAGUAGGUCCUG-5' (antisense,
SEQ ID NO: 14);

c-myc #2²⁷: 5'-ACUCGAACAGCUUCGAAAC-3' (sense, SEQ
ID NO: 15);

3'-UGAGCUUGUCGAAGCUUUG-5' (antisense,
SEQ ID NO: 16)

VEGF²⁸: 5'-CGAUGAAGCCCUGGAGUGC-3' (sense, SEQ ID
NO: 17);

3'-GCACUCCAGGGCUUCAUCG-5' (antisense,
SEQ ID NO: 18);

MDM2²⁶: 5'-GCUUCGGAACAAGAGACUCdTdT-3' (sense, SEQ
ID NO: 7);

3'-dTdTGGUUGUGACGAAUGCGAAU-5' (antisense, SEQ ID
NO:, SEQ ID NO: 8);
and pp32 (ANP32A)²⁹: 5'-AAGAAGCUUGAAUUAAGCGdTdT-3'
(sense, SEQ ID NO: 11);

3'-dTdTUUCUUCGAACUUAAUUCGC-5' (antisense,
SEQ ID NO: 12)

Ku70: 5'-ACGGAUCUGACUACUCACUCAdTdT-3' (sense,
SEQ ID NO: 19);

3'-dTdTUGCCUAGACUGAUGAGUGAGU-5' (antisense,
SEQ ID NO: 20)
```

Fluorescent siRNAs directed against CD4 labeled with FITC at the 5' end of the sense strand as described[6] were from Dharmacon.

Cell lines COS, B16, Jurkat, SKBR3 and MCF7 cells (ATCC) were grown in RPMI1640 supplemented with 10% fetal bovine serum. HeLa cells stably expressing EGFP (HeLa-GFP) were previously described[30]. Culture supernatants from COS cells stably transfected with pCMV-F105-P[8] and grown in 500 mL rolling bottles at 37° C. were purified using protein L-agarose as described[8]. Stable transfectants of B16 cells expressing HIV env were produced using pcDNA3.1-EAC-1[31] by G418 selection and single-cell cloning.

F105-P binding assay To evaluate the binding capacity of F105-P, 200 pmol FITC-siRNA was added to dilutions of F105-P previously complexed to anti-protamine (Pharmingen)-coated protein A,G beads (Pierce). After overnight incubation at 4° C. and thorough washing, absorbance at 488 nm was determined and plotted against a standard curve. Background binding to beads in the absence of F105-P was negligible.

siRNA delivery The indicated siRNAs were mixed with protamine, F105, F105-P, ML39 ScFv, ML39 ScFv-P or PBS at a molar ratio of 6:1 (siRNA concentration, 300 nM) in PBS for 30 min at 4° C. before adding to cells. Nonadherent cells ($4\times10^5$ cells in 400 µl cell culture medium) were treated in 24-well plates. HeLa-GFP and B16 cells were similarly treated at ~75% confluency in 800 µl in 6 well plates. For controls, cells were transfected with Oligofectamine (Invitrogen) or TransIT-siQUEST (Mirus) following the manufacturers' protocol. Cells were analyzed for gene expression, HIV infection, or proliferation 2 days following siRNA treatment.

HIV infection, transfection and detection CD4 T cells, isolated from normal donor PBMCs by selection with CD4 immunomagnetic beads (Miltenyi Biotec), were stimulated with phytohemagglutinin (4 µg/mL, Difco) for 4 days and infected with HIV strain IIIB (NIH AIDS Reagent Repository) at an MOI of 0.1. Seven days later, cells were treated with siRNAs as indicated. Similarly, Jurkat cells were infected with HIV strain IIIB at an MOI of 0.01 and treated with siRNAs 3 days later. HeLa-GFP cells in 6-well plates were transfected with □HXB3 (NIH AIDS Reagent Repository) using an Effectine Transfection Kit (Qiagen) according to the manufacturer's protocol. Two days later, transfected cultures were treated with siRNAs as indicated and analyzed for HIV and GFP expression 2 days after treatment. GFP expression was analyzed by Northern blot and by flow cytometry. Cells replicating HIV were identified by flow cytometry analysis of intracellular staining of permeabilized cells for RD1-conjugated anti-p24 as described[13]. Viral production was also assayed by p24 Ag ELISA (Perkin Elmer Life Science Inc.) of culture supernatants.

Flow cytometry Trypsinized B16 cells were permeabilized using 0.1% Triton X-100 (Beckman Coulter) and stained with a rabbit anti-mouse c-myc or VEGF primary antibody (R&D Systems, Inc.) followed by PE-labeled goat anti-rabbit secondary antibody (BD Pharmingen). Ku70 expression in breast cancer cell lines was similarly analyzed using PE-conjugated Ku70 antibody (Santa Cruz). Flow cytometry was performed on a FACScalibur with CellQuest software (Becton Dickinson).

Northern blot Total RNA was harvested from treated HeLa-GFP cells using Trizol (Invitrogen Life Technologies) and analyzed by Northern blot probed for GFP and β-actin as described[30]. Delivery of siRNA into B16 cells was analyzed by modified Northern blot designed to capture small RNAs efficiently as described[13].

Interferon Assay gp160-B16 cells ($1\times10^6$/2 ml) were mock treated or treated with F105-P and GFP siRNA (300 pmol) or 5 µg/ml poly(I:C). After 24 h RNA was isolated and analyzed by quantitative RT-PCR for induction of IFN or interferon responsive genes as described below.

Quantitative PCR Total RNA (1 µg) isolated with Trizol was reverse transcribed using Superscript III (Invitrogen) and random hexamers, according to the manufacturer's protocol. Real-time PCR was performed on 0.2 µl of cDNA, or a comparable amount of RNA with no reverse transcriptase, using Platinum Taq Polymerase (Invitrogen) and a Biorad iCycler. SYBR green (Molecular Probes) was used for the detection of PCR products. All reactions were done in a 25 µl reaction volume in triplicate. Primers for mouse c-myc and GAPDH are:

```
                             (SEQ ID NO: 21)
GAPDH-fwd      5'-TTCACCACCATGGAGAAGGC-3'

(SEQ ID NO: 22)
GAPDH-rev      5'-GGCATGGACTGTGGTCATGA-3'

(SEQ ID NO: 23)
c-myc-fwd      5'-CCCCTGGTGCTCCATGAG-3'

(SEQ ID NO: 24)
c-myc-rev      5'-TCCTCCTCAGAGTCGC-3'

(SEQ ID NO: 25)
STAT1-fwd      5'-TTTGCCCAGACTCGAGCTCCTG-3'

(SEQ ID NO: 26)
STAT1-rev      5'-GGGTGCAGGTTCGGGATTCAAC-3'
```

-continued

```
                                        (SEQ ID NO: 27)
OAS1-fwd         5'-GGAGGTTGCAGTGCCAACGAAG-3'

(SEQ ID NO: 28)
OAS1-rev         5'-TGGAAGGGAGGCAGGGCATAAC-3'

(SEQ ID NO: 29)
Interferon β-fwd 5'-CTGGAGCAGCTGAATGGAAAG-3'

(SEQ ID NO: 30)
Interferon β-rev 5'-CTTGAAGTCCGCCCTGTAGGT-3'
```

PCR parameters consisted of 5 min of Taq activation at 95° C., followed by 40 cycles of PCR at 95° C.×20 sec, 60° C.×30 sec, and 69° C.×20 sec. Standard curves were generated and the relative amount of target gene mRNA was normalized to GAPDH mRNA. Specificity was verified by melt curve analysis and agarose gel electrophoresis.

Cell proliferation $^3$H-thymidine (1 μCi) was added for 6 hr to treated B16 or gp160-B16 cells (2×10$^4$) in microtiter wells. Cells were harvested and analyzed by scintillation counting using a Top Count microplate reader (Packard).

Tumor implantation and treatment in mice All animal experiments were approved by the CBR Institute Animal Care and Use Committee. Female C57/BL6 mice, 8-10 wk of age weighing 20-25 g, were purchased from Jackson Laboratories. To evaluate in vivo delivery of siRNA, B16 or gp160-B16 cells (2×10$^6$) were injected s.c. into the right flank. The day following the first detection of tumors (day 9), mice were injected either directly into the tumor or i.v. with 50 μg of FITC-labeled siRNA in PBS or mixed with Oligofectamine or F105-P. Mice were sacrificed 16 hr later and tumors were snap-frozen for cryosectioning. Distribution of FITC-siRNA in tumor and adjacent tissue was evaluated by fluorescence microscopy and hematoxylin and eosin staining of consecutive sections. For treatment studies, B16 or gp160-B16 cells (5×10$^6$ cells) were implanted s.c. into the right flank of groups of 8 mice on day 0, and tumors were detected by day 5. F105-P complexed with c-myc siRNAs #1 and #2, MDM2 siRNA and VEGF siRNA (80 μg siRNA in an injection volume of 100 μl) at a molar ratio of F105-P:total siRNA of 1:6 was injected either directly into the tumor or intravenously on day 0, 1 and 3 after tumor implantation. Tumor size was measured daily by calipers from day 5 until day 9 after implantation. The mice were sacrificed on day 9 and the tumor dissected and weighed.

Anti-ErbB2 ML39 ScFv and ScFv-P Baculovirus vectors expressing His-tagged anti-ErbB2 ML39 ScFv and ScFv-protamine fragment (amino acids 8-29) (ScFv-P) were expressed and purified as previously described[10]. Briefly, ML39 ScFv was purified by Ni$^{++}$ chromatography after ammonium sulfate precipitation of culture supernatants of SF9 cells infected with recombinant viruses expressing ML39 ScFv, generated using BaculoGold (Pharmingen). ML39 ScFv-P was similarly expressed from baculovirus, but extracted from SF9 cells using 6 M guanidine hydrochloride (GuanHCl) followed by Ni$^{++}$ chromatography in 6 M Guan-HCl. The eluted protein was gradually dialyzed into PBS and then into PBS containing 5% glycerol, 0.5 M arginine, 1 mM EGTA, and 1 mM glutathione in reduced and oxidized form. Both proteins were finally dialyzed into PBS containing 5% glycerol, concentrated and stored at −70° C.

Delivery using ML39 ScFv-P To detect fusion protein binding, SKBR3 and MCF7 cells were detached using enzyme-free cell dissociation buffer (Life Technologies), washed with PBS containing 5% FBS, and incubated (5×10$^5$ cells/ml) for 30 min at 4° C. with ML39 ScFv-P (1 μg/ml) before further incubation with FITC-conjugated His tag monoclonal antibody (Babco) for 30 min. Fixed cells were analyzed by flow cytometry. For delivery and silencing experiments, the indicated proteins were incubated with FITC-siRNA (300 nM) or Ku70 siRNA (indicated amounts) for 30 min at 4° C. before adding to cells. FITC-siRNA delivery was assessed 4 hr after culture at 37° C. and Ku70 silencing was assessed 3 days later.

Statistics All in vitro experiments were performed in triplicate, except for proliferation assay, which was performed in octuplicate. The results are described as mean±SEM. Statistical analysis was performed by one-way analysis of variance (ANOVA) and comparisons among groups were performed by independent sample t-test or Bonferroni's multiple-comparison t-test.

Results

Figure 10A:
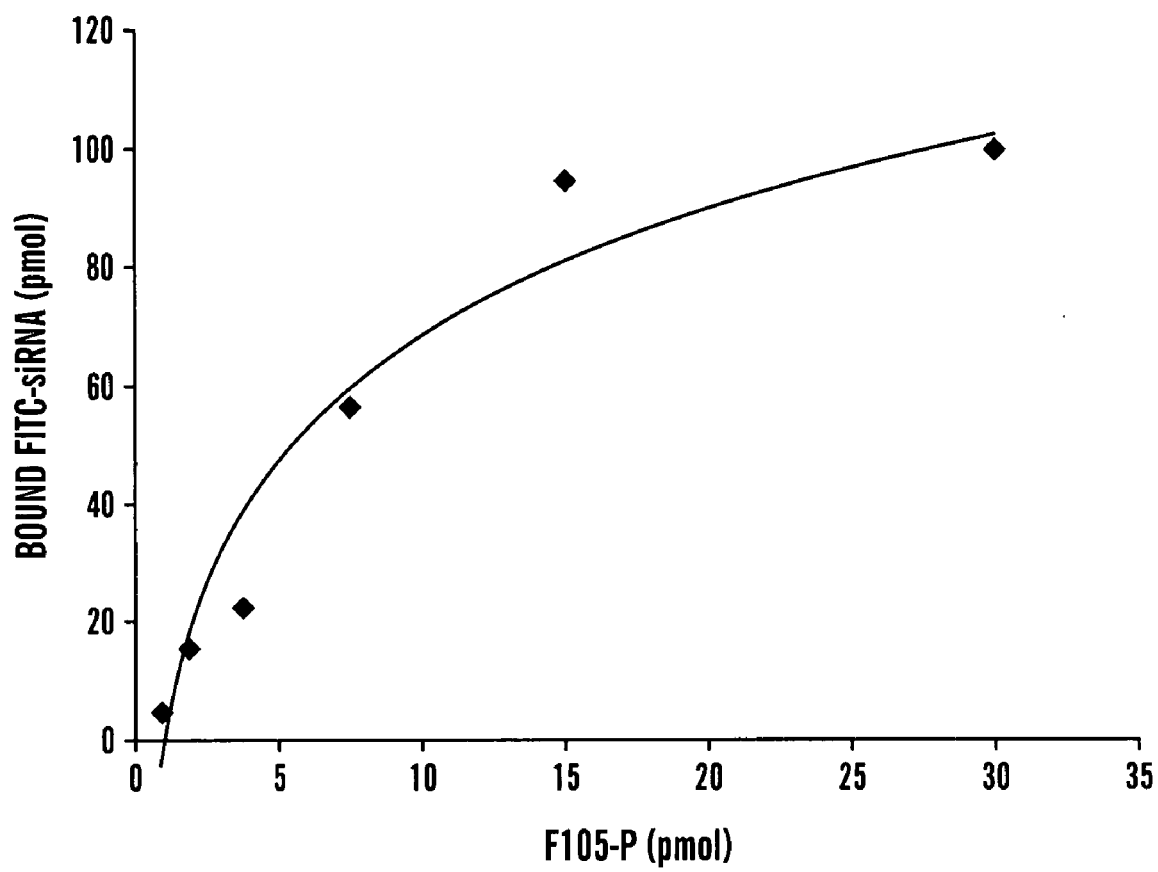
FIGS. 10A-10C show that F105-P binds and delivers siRNAs only into HIV env-expressing cells.
Figure 10B:
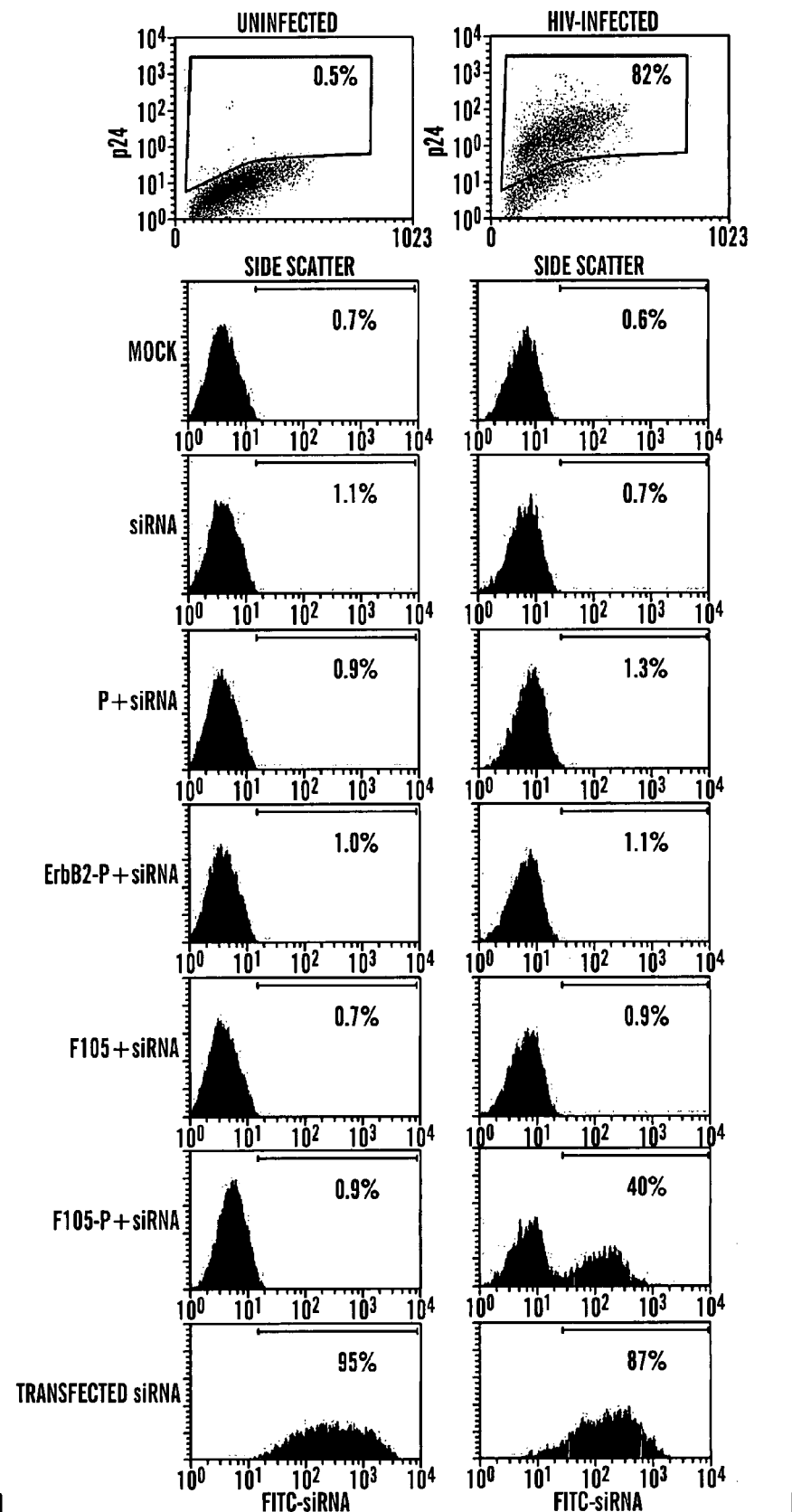
Figure 10C:
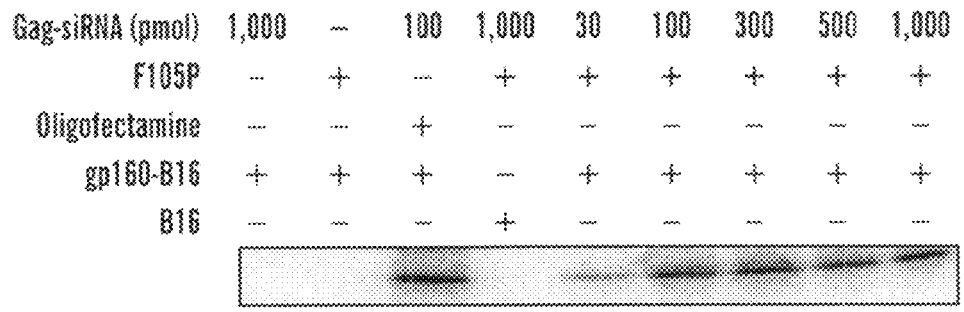

F105-P delivers siRNAs only to HIV env$^+$ cells F105-P was expressed and purified from COS cells transfected with a bicistronic plasmid encoding both the F105 Igκ light chain and the heavy chain Fab fragment fused at its C-terminus to protamine. To determine the capacity of F105-P to bind siRNA, a fixed amount of FITC-labeled siRNA was incubated with varying amounts of the fusion protein, precipitated with anti-protamine coupled beads, and the absorbance at 488 nm of captured siRNA measured. Each molecule of F105-P can bind ~6 siRNA molecules (FIG. 10A). To determine whether F105-P was able to deliver siRNA specifically into cells expressing HIV env, FITC-siRNA was added either alone or with the unmodified F105 antibody or with F105-P to an HIV-infected Jurkat cell culture. Lipid transfection was used as a positive control for delivery. Transfected FITC-siRNA was comparably taken up by ~70% of both uninfected and infected cells. Both infected and uninfected cells did not appreciably take up FITC-siRNA by itself or when mixed with the antibody fragment lacking protamine, with an irrelevant antibody-protamine fusion protein or with unmodified protamine. When mixed with F105-P, the uninfected cells still did not take up the siRNA, while 40% of the infected Jurkat cells did (FIG. 10B). Specific delivery of gag siRNA into cells expressing HIV env was verified by modified Northern blot using mouse melanoma B16 cells stably transfected with env (gp160-B16) or empty vector (B16) (FIG. 10C). gag siRNA was detected in gp160-B16 cells treated with gag siRNA mixed with F105-P, but not when gp160$^-$ B16 cells were incubated with the same mixture or in gp160-B16 cells incubated with uncomplexed gag-siRNA. Uptake plateaued when about 100 pmol of siRNA [100 nM] was added.

Figure 11A:
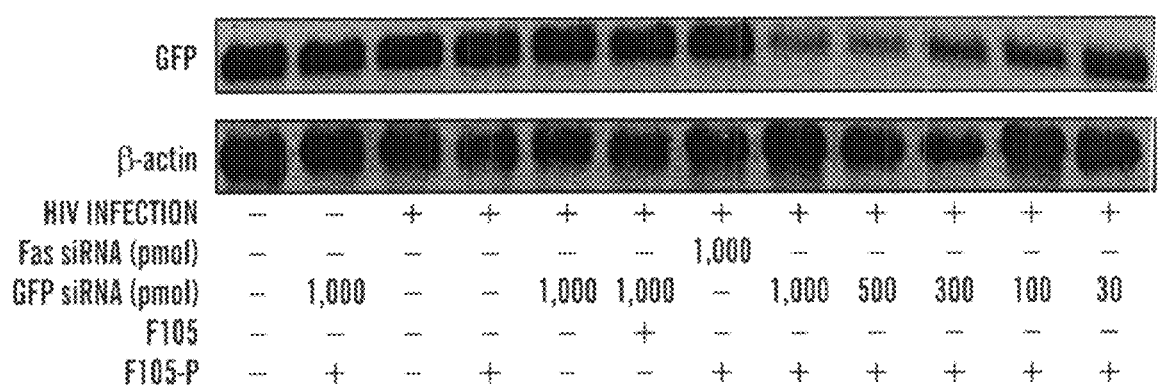
FIGS. 11A-11B show that GFP-siRNA delivered by F105-P reduces eGFP expression only in HeLa-GFP cells transfected with HIV λHXB3. HeLa-GFP cells that were transfected with HIV plasmid with ~80% efficiency or mock transfected were treated with GFP siRNA or Fas siRNA delivered by F105 or F105-P or medium and analyzed for EGFP mRNA (FIG. 11A) by Northern blot or protein (FIG. 11B) by flow cytometry. eGFP expression is silenced when GFP siRNA is complexed with F105-P only in infected cells, which stain for intracellular HIV p24. The p24-untransfected cells in each culture have not down-modulated eGFP and serve as an internal specificity control. Silencing increases in a dose-dependent manner.
Figure 11B:
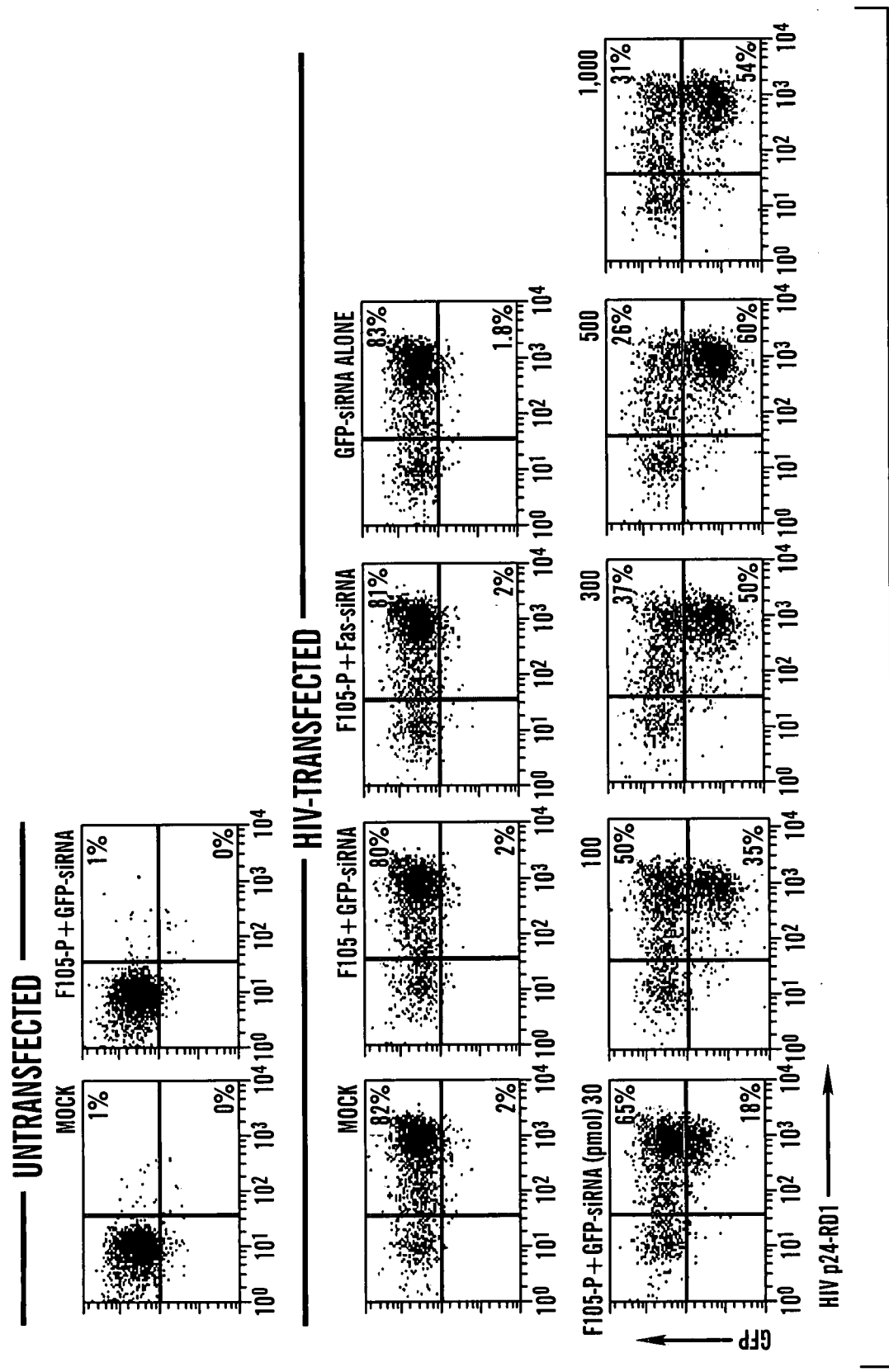

F105-P-delivered siRNA silences gene expression To evaluate whether F105-P-delivered siRNA can silence target gene expression, F105-P was used to introduce siRNAs targeting EGFP into HeLa cells stably expressing EGFP (HeLa-GFP). HeLa-GFP cells were transfected with HIV λHXB3 with about 80% efficiency. GFP siRNA delivered with F105-P reduced EGFP mRNA (FIG. 11A) and protein (FIG. 11B) in a dose-dependent manner only in transfected cells that stain for HIV gag antigen. Silencing plateaued at about 300 pmol [300 nM] of siRNA. Silencing by F105-P-delivered siRNA was specific since no reduction of EGFP expression was observed in untransfected p24$^-$ cells or with irrelevant fas siRNA or without antibody or with unmodified F105 in place of F105-P. The reduction in EGFP mRNA confirms that siRNA delivered by the fusion protein silences target gene expression via mRNA degradation.

Figure 12A:
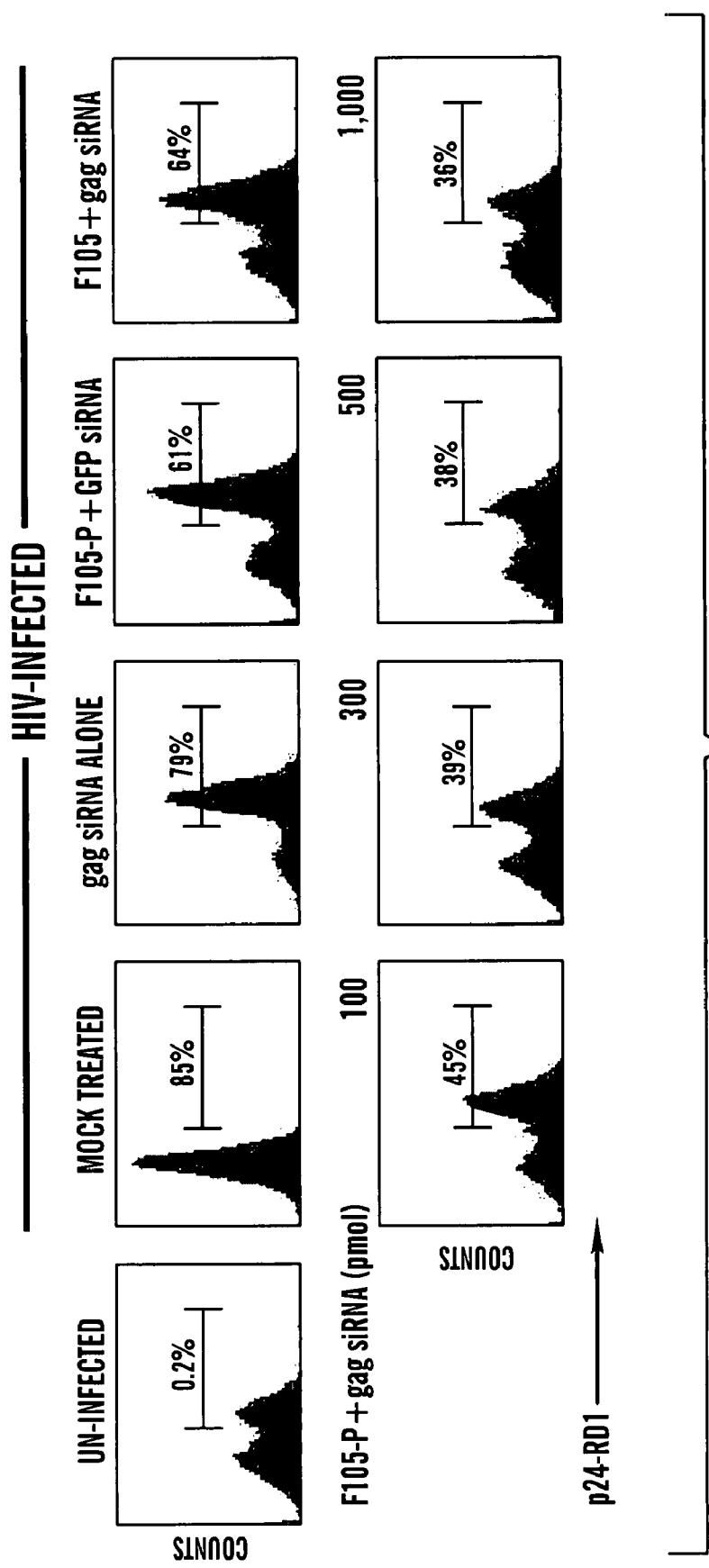
FIGS. 12A-12B show that F105-P complexed with gag-siRNA inhibits HIV production in infected primary CD4 cells. HIV-infected CD4 T cells (~85% infected by p24 staining), treated with gag siRNA or GFP siRNA with no delivery agent or complexed with F105 or F105-P, were analyzed 2 d later for viral replication by intracellular p24 staining (FIG. 12A) and by p24 Ag ELISA of culture supernatants (FIG. 12B). The env-specific antibody by itself (see F105-P+irrelevant GFP siRNA and F105+gag siRNA conditions) reduced HIV replication modestly (~25-28%) because of its viral neutralization activity, while F105-P-delivered gag siRNA reduced viral production by ~58% (by p24 staining) or by ~77% (ELISA) at the highest dose. These cells are resistant to lipid-mediated siRNA transfection and no inhibition of HIV was observed in transfected controls.
Figure 12B:
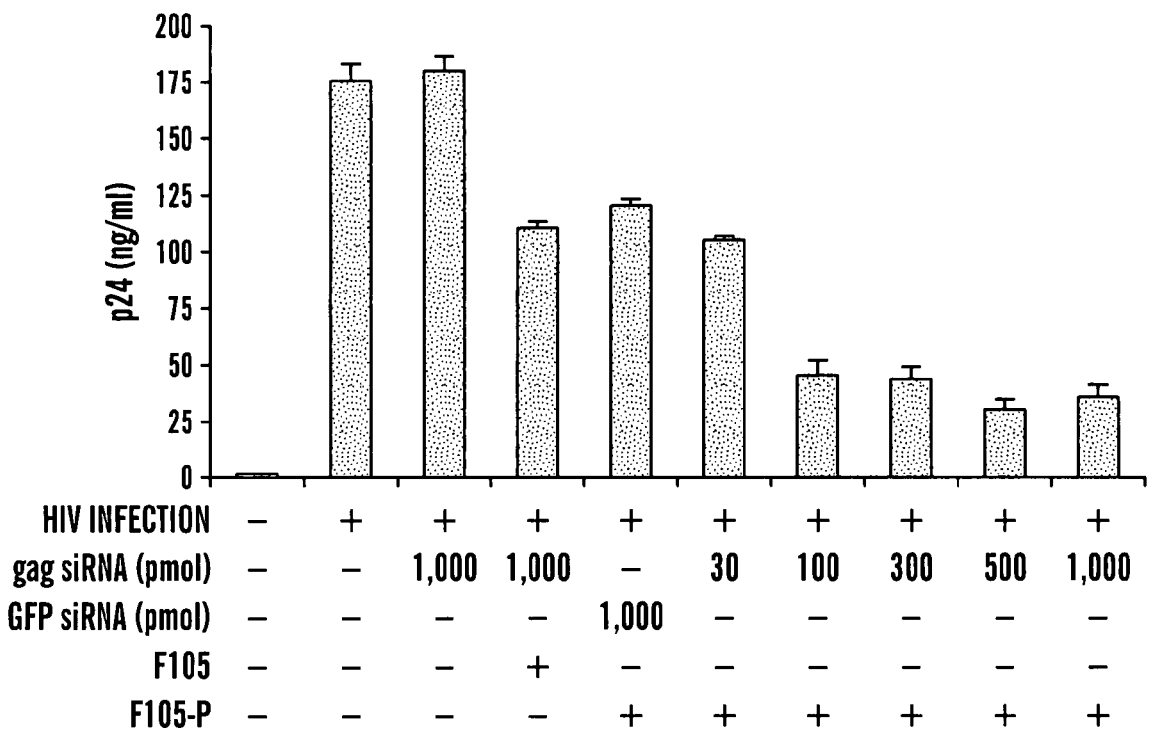

Delivered siRNA inhibits HIV in infected T cells Primary T cells are notoriously difficult to transfect with conventional lipid-based strategies. We therefore evaluated whether F105-P could deliver gag siRNA into HIV-infected CD4 T cells to reduce virus replication. F105-P loaded with gag siRNA reduced HIV replication in previously infected CD4 T cells in a dose-dependent manner (FIG. 12A). The proportion of productively infected cells declined from 85% in untreated cultures to 36% when 1 nmol of gag siRNA was added. Moreover, even with 10-fold less siRNA, the proportion of cells staining for HIV gag was only 45%. Release of viral particles from F105-P and gag-siRNA treated primary cells into culture supernatants, as measured by HIV p24 ELISA, was reduced from 170 ng/ml to <40 ng/ml provided at least 100 pmol of siRNA was used (FIG. 12B). In these experiments, infection was reduced by ~30% (from ~170 ng/ml to ~115 ng/ml) in the presence of either F105 or F105-P antibody in the absence of siRNA, due to the neutralizing activity of the antibody. Nonetheless, the siRNA-coated antibody more efficiently suppressed HIV replication in these difficult to transduce primary T cells. Moreover, suppression could be achieved even in cells that were already productively infected.

Figure 13A:
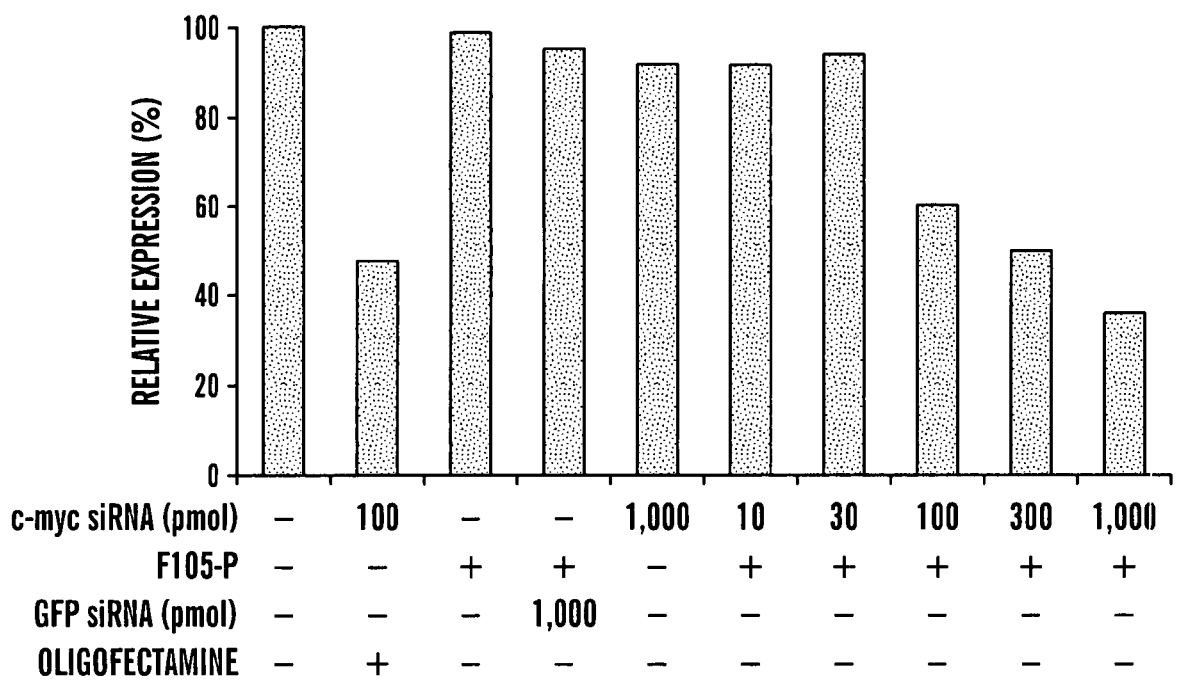
FIGS. 13A-13I show that F105-P delivers c-myc, MDM2 and VEGF siRNAs, silences gene expression, and inhibits tumor proliferation only in B16 melanoma cells expressing HIV env. gp160-B16 were treated with increasing concentrations of 2 siRNAs directed against c-myc (FIG. 13A, FIG. 13B) or an siRNA targeting VEGF (FIG. 13C). Gene expression was analyzed by quantitative PCR (FIG. 13A) or flow cytometry of permeabilized cells (FIG. 13B, FIG. 13C). In (FIG. 13B, FIG. 13C) delivery was via F105-P except in the points marked 100 T, which were via transfection of 100 pmol siRNA, a saturating concentration for transfection. Silencing in (FIG. 13B) was similar when similar concentrations of c-myc siRNA #1 (Δ), #2 (◇) or both ( ) were used. Controls in FIG. 13B and FIG. 13C also showed no reduction in mean fluorescence intensity by an irrelevant GFP-siRNA or in B16 cells not expressing gp160 (data not shown). Silencing requires gp160 expression on target cells and specific siRNA and is dose-dependent, reaching a plateau at about 100-1000 pmol siRNA. Gene silencing was comparable when siRNAs were either delivered by F105-P or transfected with Oligofectamine.
Figure 13B:
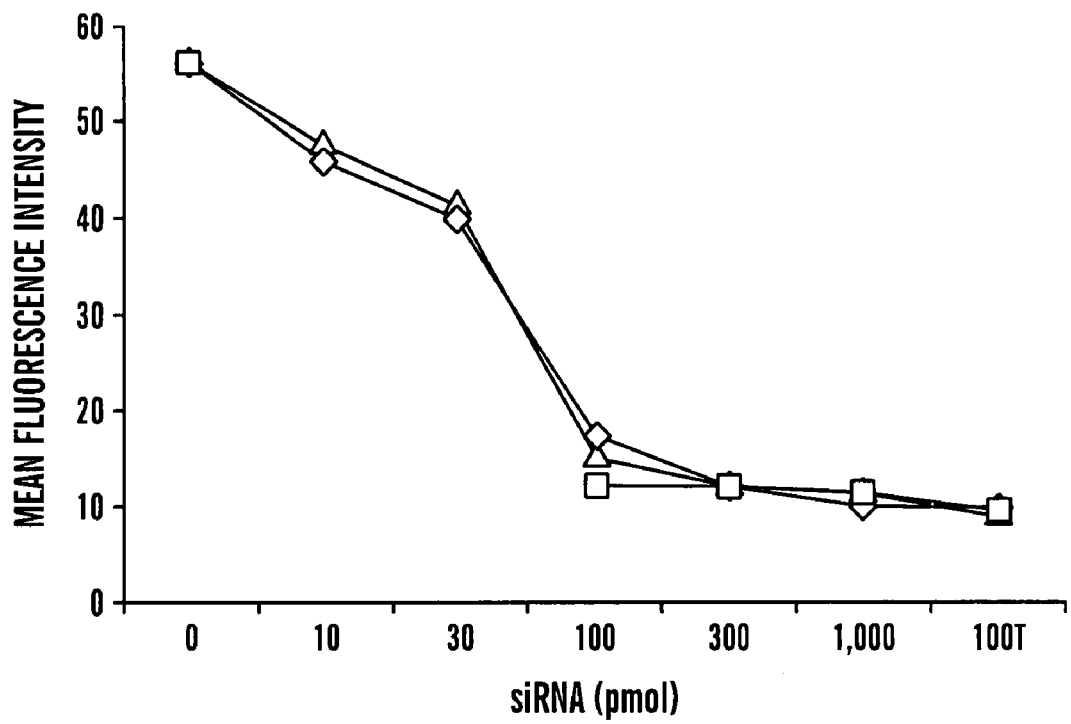
Figure 13C:
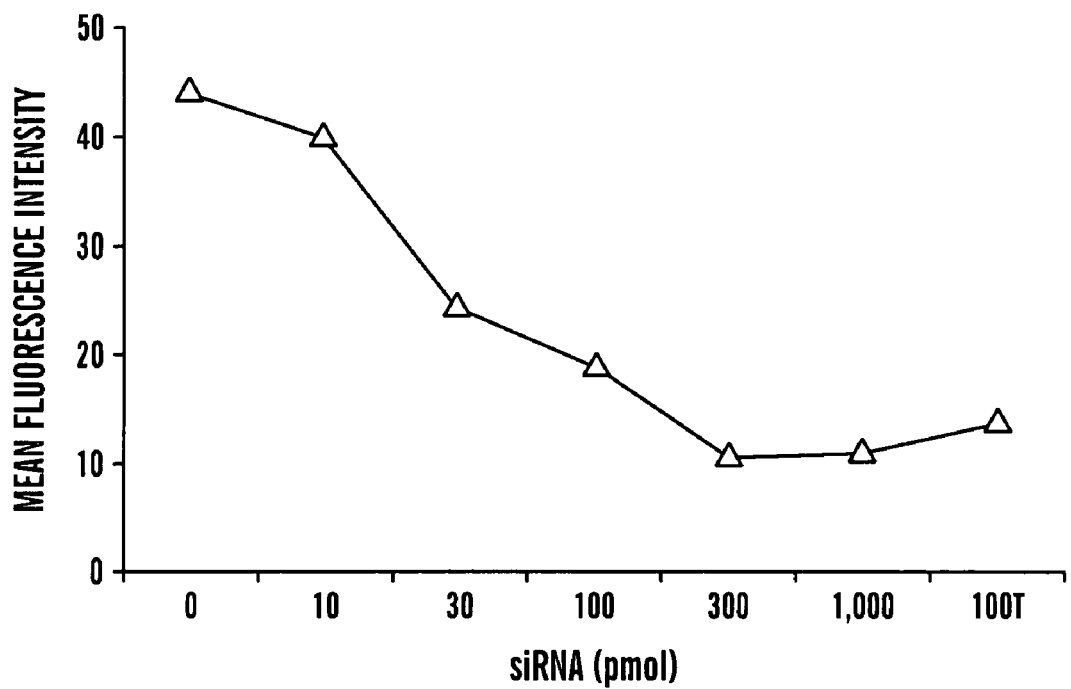
Figure 13D:
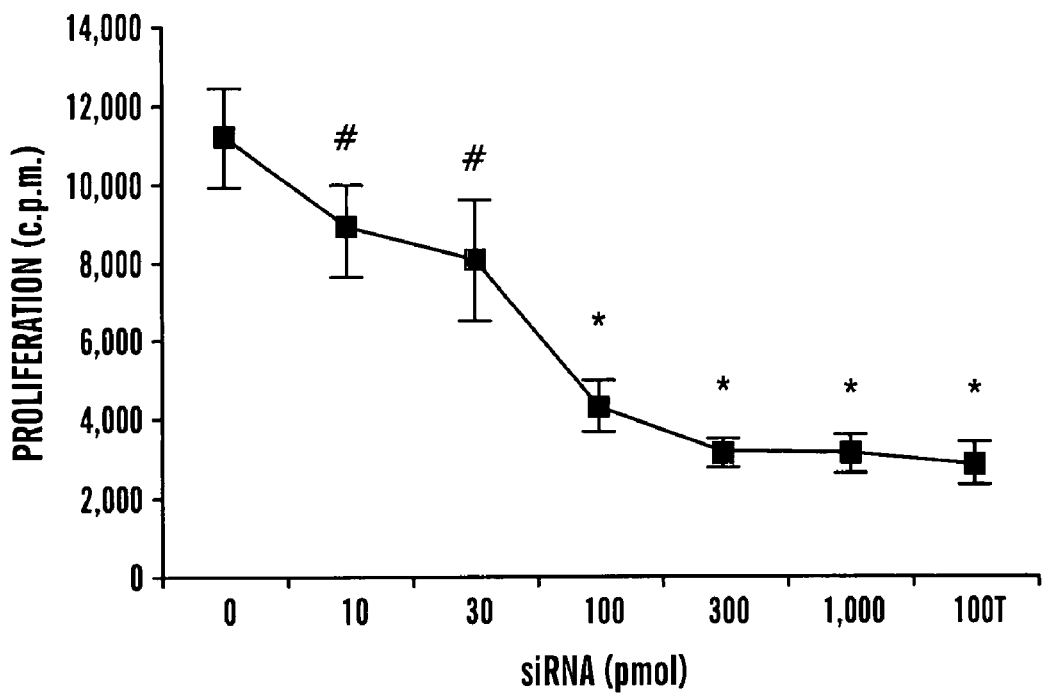
Figure 13E:
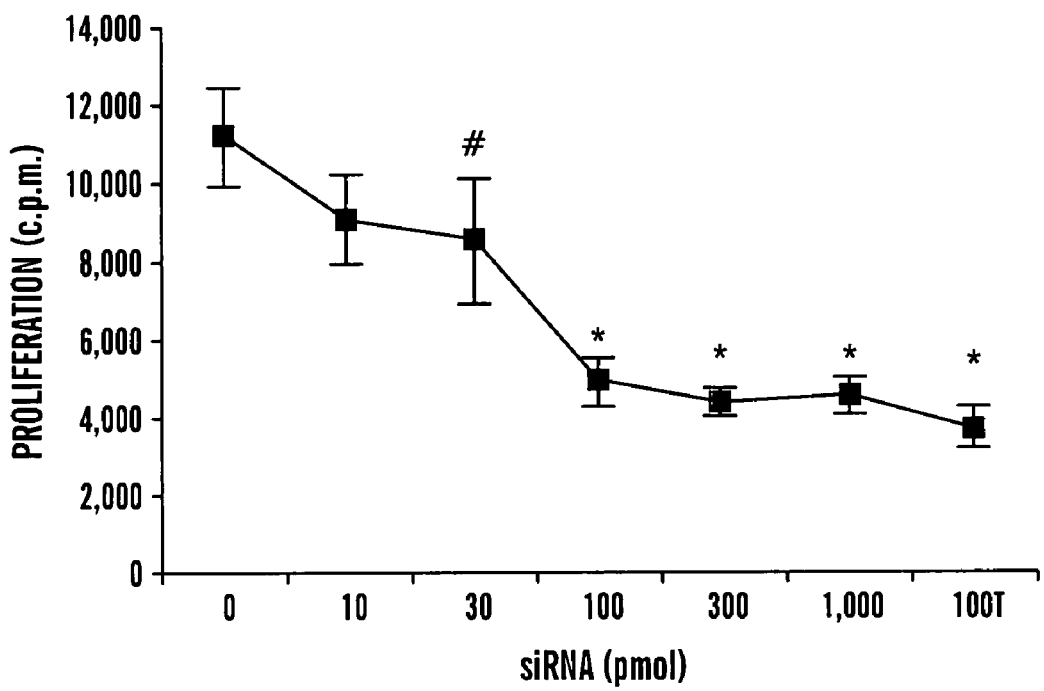
Figure 13F:
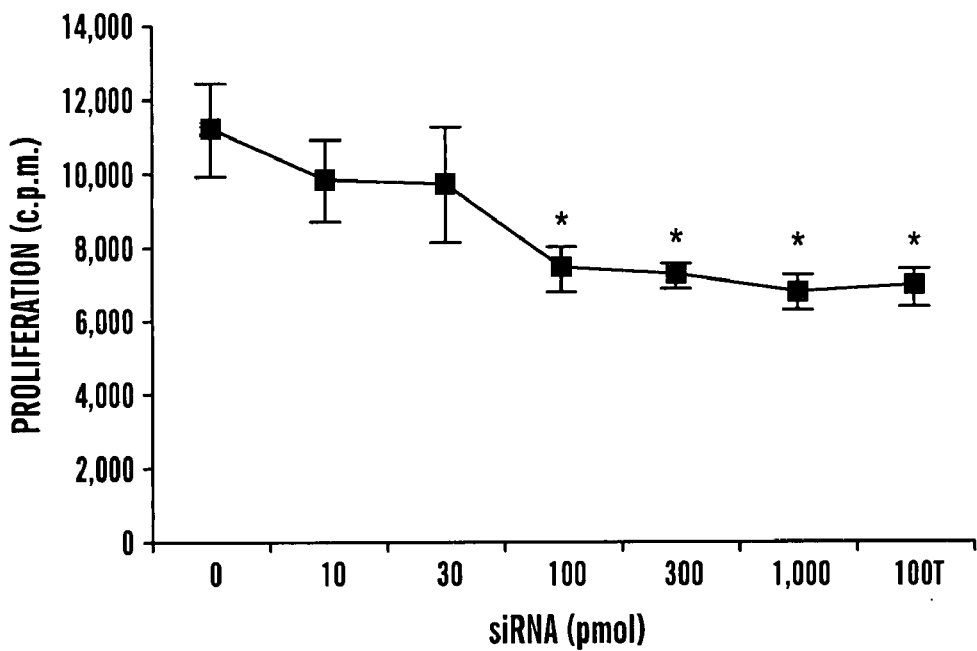
Figure 13G:
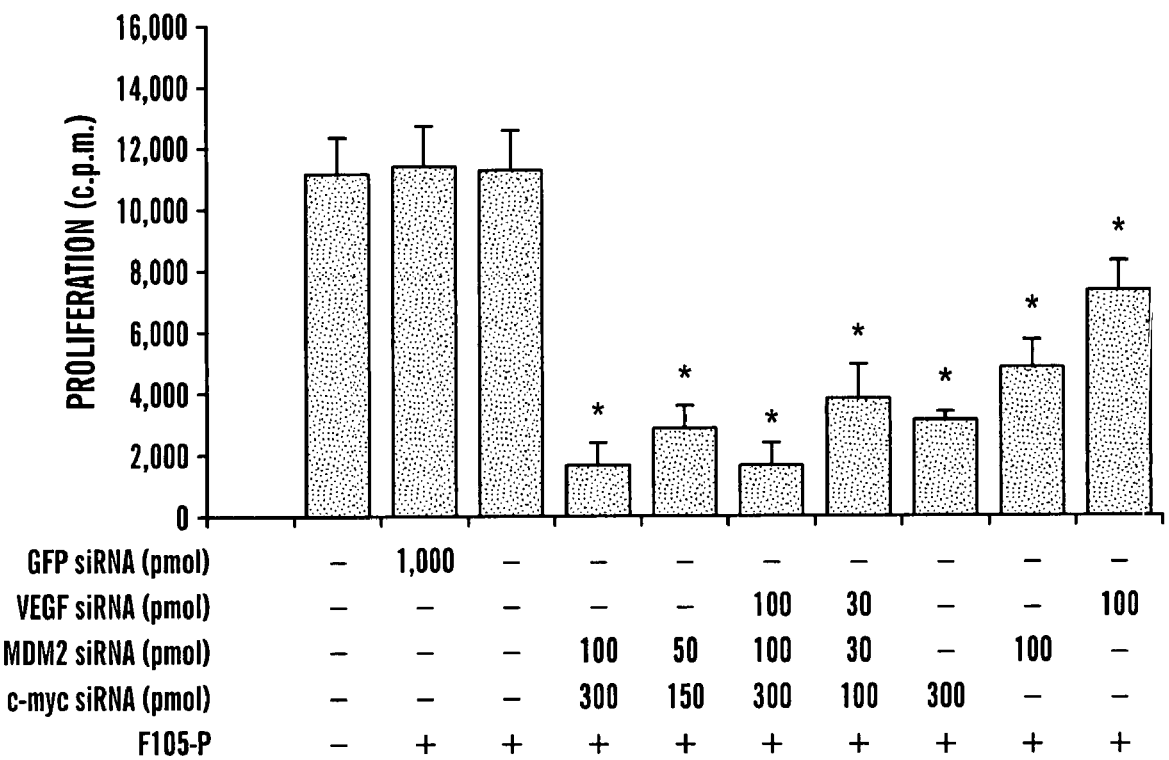
Figure 13H:
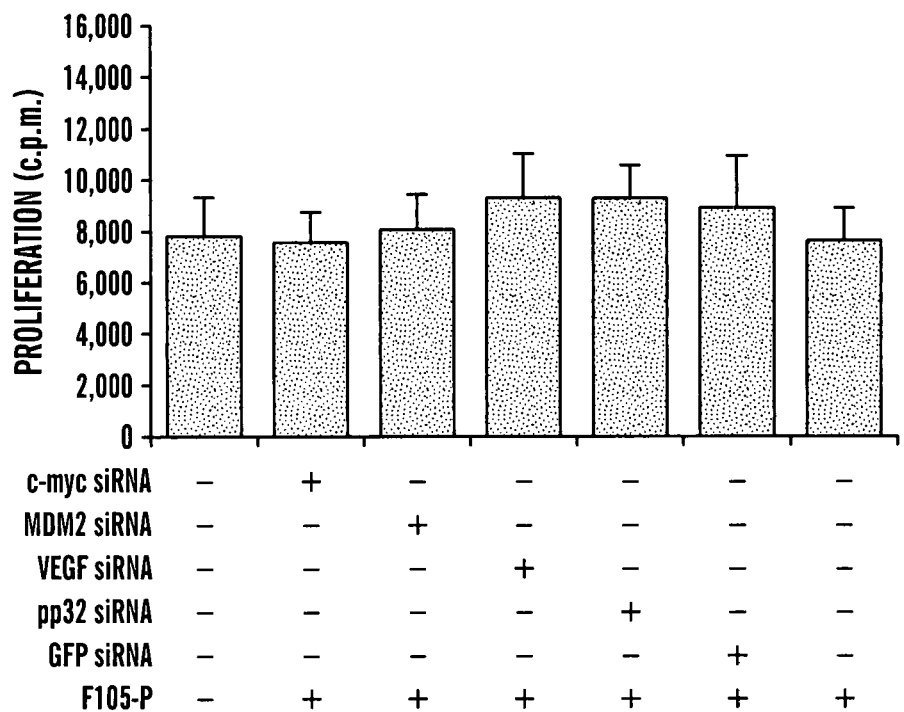

Delivered oncogene siRNAs inhibit proliferation Because there is no good mouse model for HIV, to test the ability of antibody-protamine fusion proteins to deliver siRNAs in vivo, we subcutaneously injected gp160-B16 cells as a tumor model. siRNAs targeting a variety of oncogenes, tumor growth factors, anti-apoptotic genes and drug resistance genes have been shown to suppress tumor growth, mostly in vitro[1]. If siRNAs could be specifically targeted to tumor cells, then any gene required for normal cell growth or survival could in principle be targeted. Previously identified siRNAs against c-myc, MDM2 and VEGF, alone and in combination, were tested for their ability to down-regulate gene expression and reduce gp160-B16 cell proliferation in vitro (FIG. 13). Two siRNAs directed against c-myc were effectively and specifically loaded only into HIV env-expressing B16 cells to reduce mRNA assessed by quantitative RT-PCR (FIG. 13A) and c-myc protein assessed by flow cytometry (FIG. 13B). F105-P and c-myc-siRNAs had no effect on B16 cells not expressing HIV env. When both c-myc siRNAs were loaded via F105-P into gp160-B16 cells, tumor cell proliferation was reduced in a dose-dependent manner, to a maximum 3-fold suppression at siRNA concentrations >100 nM (FIG. 13D). Proliferation was reduced to a similar extent by delivered siRNA and transfected siRNA at saturating siRNA concentrations of ~100 pmol. Similar gene silencing was obtained by delivering VEGF and MDM2 siRNAs (FIG. 13C), but VEGF siRNA had only a modest effect on inhibiting in vitro tumor cell growth (FIG. 13E, FIG. 13F). However, by blocking angiogenesis VEGF siRNA might have more of an effect in vivo. A control siRNA targeting the putative tumor suppressor pp32[9], though effective at silencing gene expression, did not inhibit, but may have slightly enhanced, tumor growth. Combining the siRNAs targeting c-myc and MDM2 or all three genes led to the greatest inhibition of gp160-B16 cell proliferation. Tumor growth was inhibited 7-fold by siRNAs targeting all 3 genes, compared to 3-fold inhibition by combining the two siRNAs targeting c-myc or 2-fold inhibition or less by each of the siRNAs against MDM2 or VEGF. (FIG. 13G). Moreover, none of these siRNAs delivered by F105-P had any significant effect on the growth of B16 tumor cells not expressing HIV env (FIG. 13H).

Figure 13I:
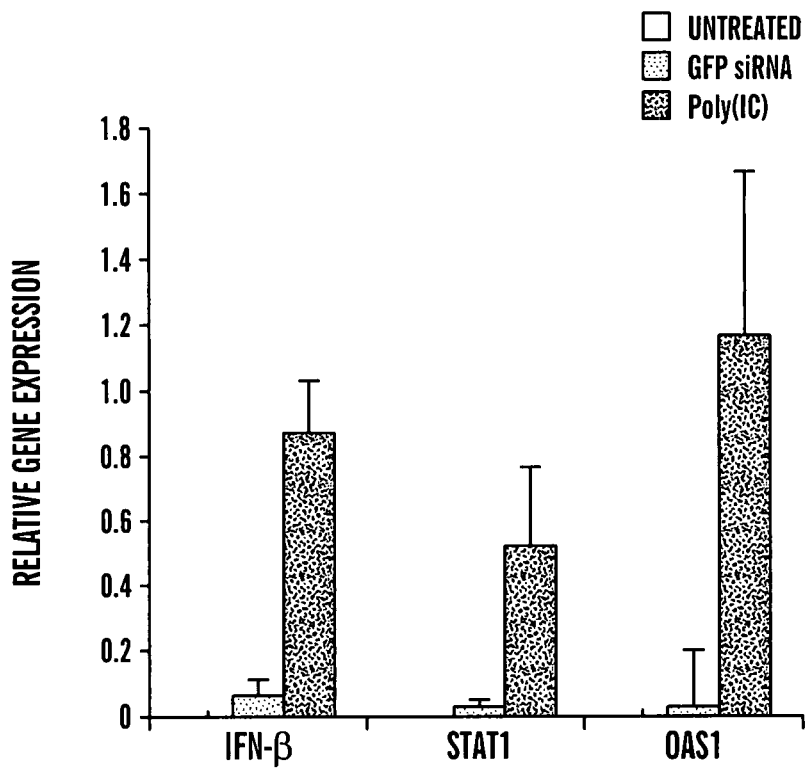

Delivered siRNAs do not trigger interferon responses Delivered siRNAs can potentially activate nonspecific inflammatory responses, which might cause toxicity, either because cytosolic double-stranded RNAs directly trigger an interferon response or do so indirectly via binding Toll-like receptors (TLR) that recognize RNA (TLR3, TLR7) on the cell surface or within endosomes. We therefore assayed by quantitative RT-PCR expression of interferon-β (IFN-β) and 2 key interferon responsive genes, 2',5'-oligoadenylate synthetase (OAS1) and Stat-1, around the expected peak response time (24 hr) in gp160-B16 cells that were either mock treated, exposed to irrelevant GFP siRNA delivered by F105-P, or treated with the interferon inducer poly(I:C) (FIG. 13I). Although poly(I:C) induced the expression of all 3 genes, treatment with F105-P-complexed siRNA had no statistically significant effect on the expression of any of these genes. Therefore, F105 delivery of siRNAs does not appear to trigger potentially toxic IFN responses.

Figure 14A:
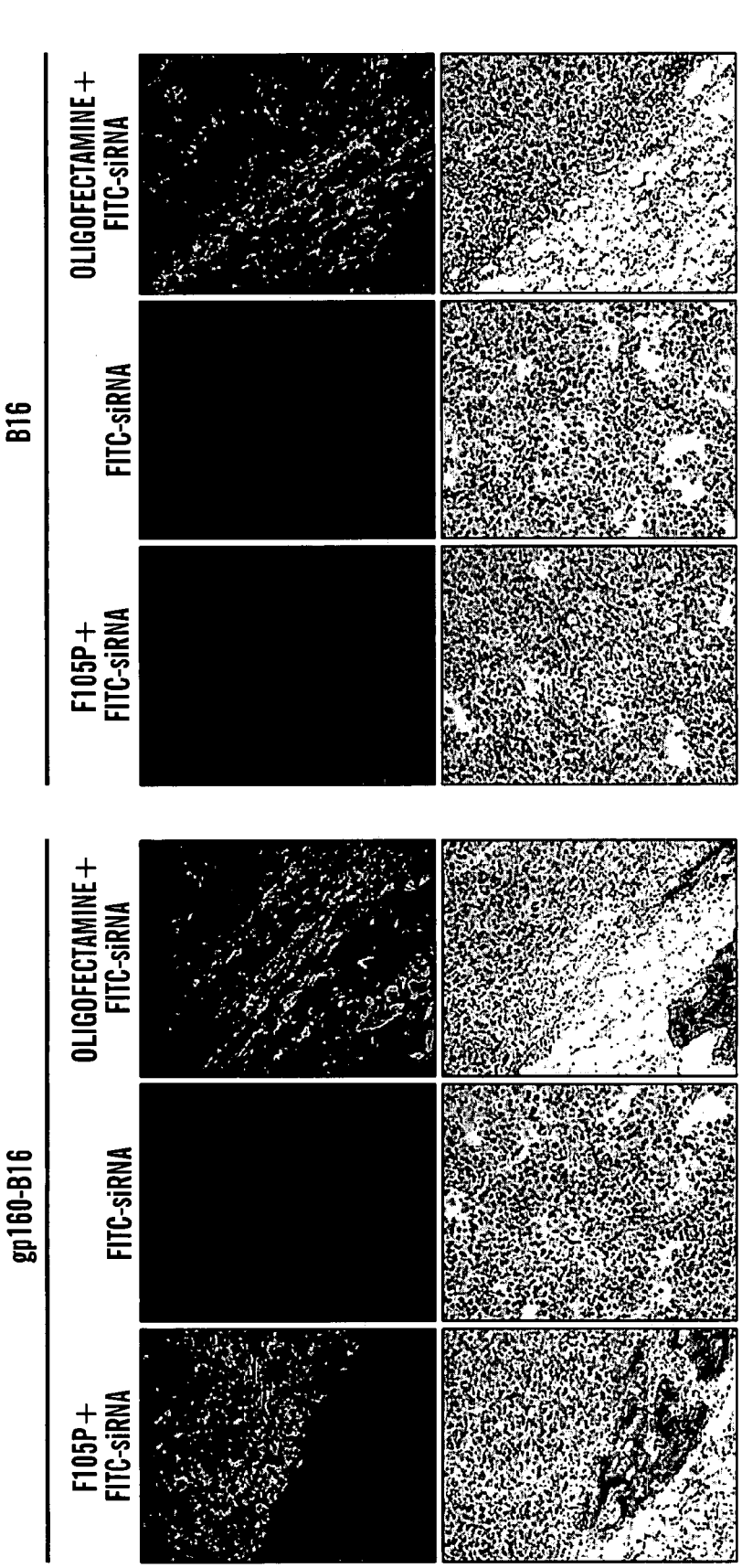
FIGS. 14A-G show intratumoral or intravenous injection of siRNAs complexed with F105-P delivers siRNAs only into env-bearing B16 tumors to suppress tumor growth.
Figure 14C:
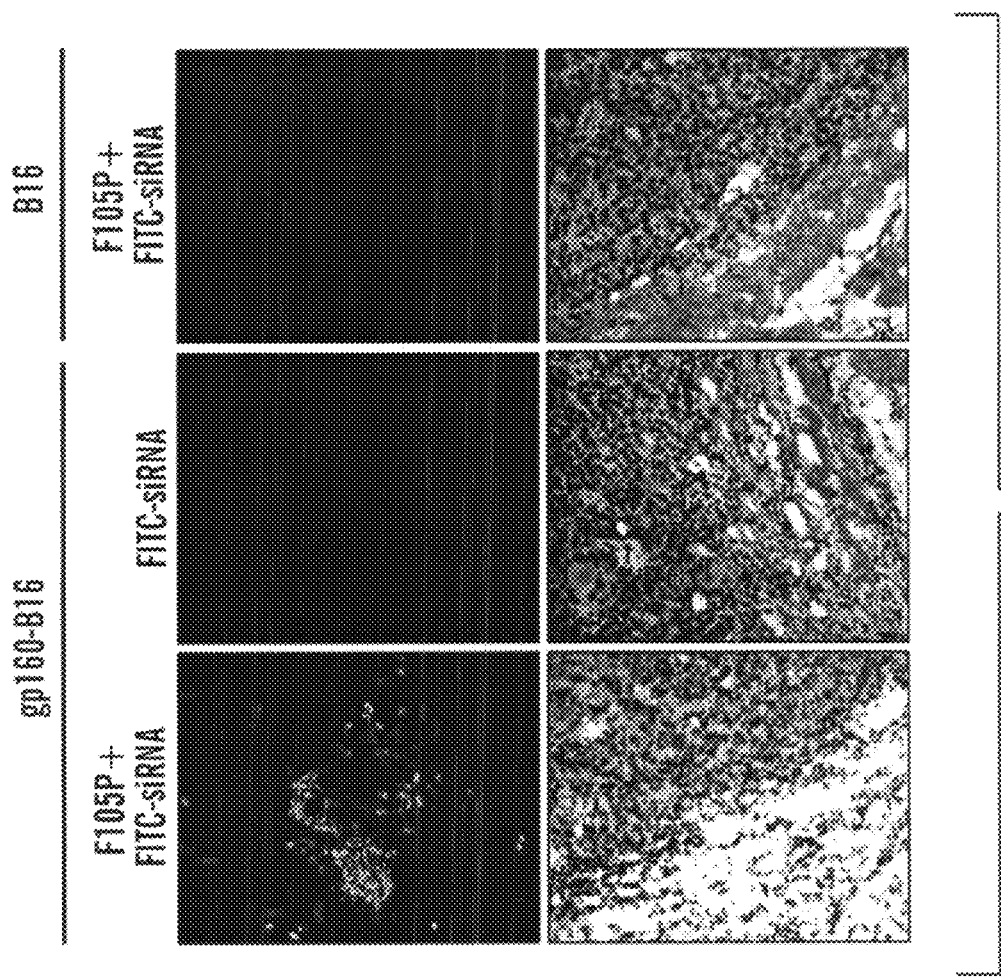
Figure 14B:
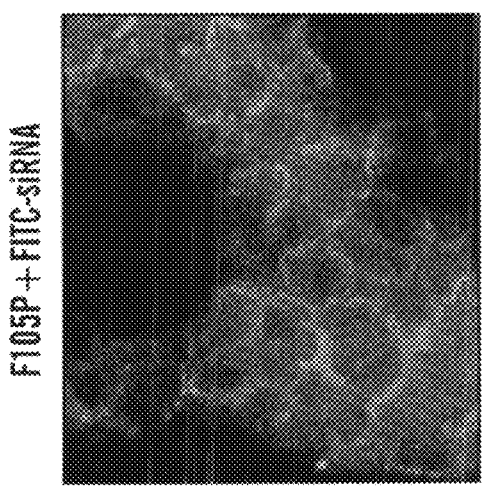
Figure 14D:
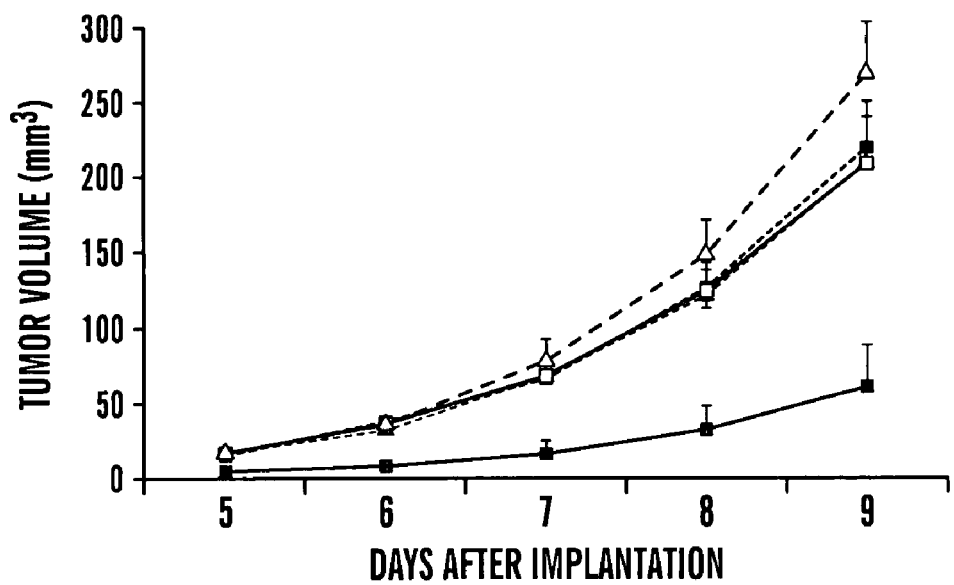
Figure 14E:
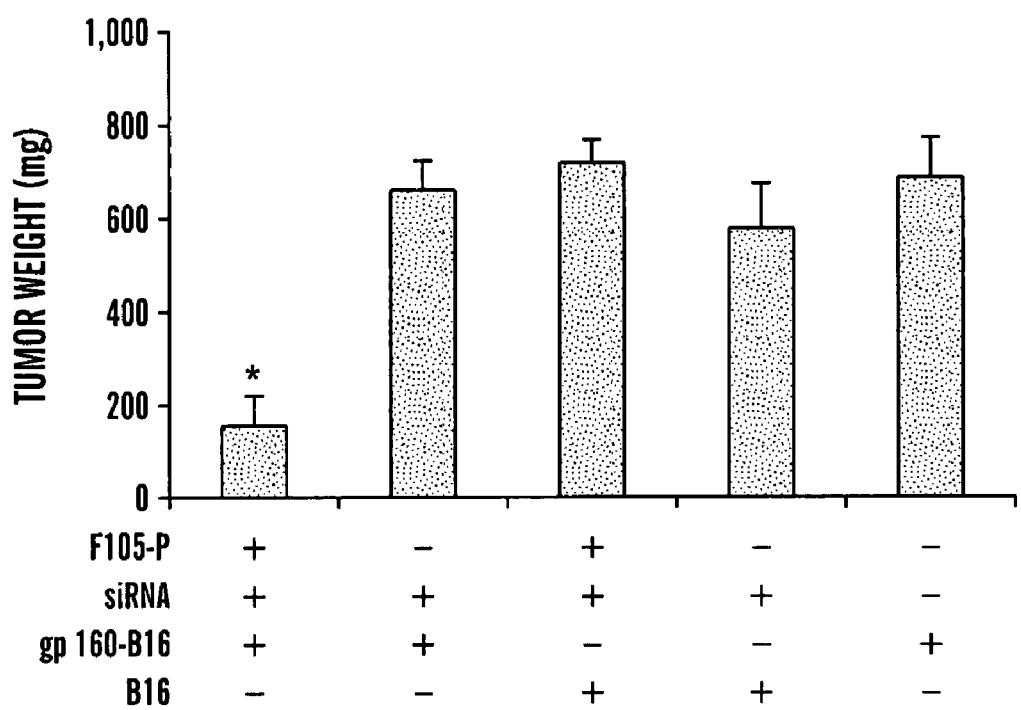
Figure 14F:
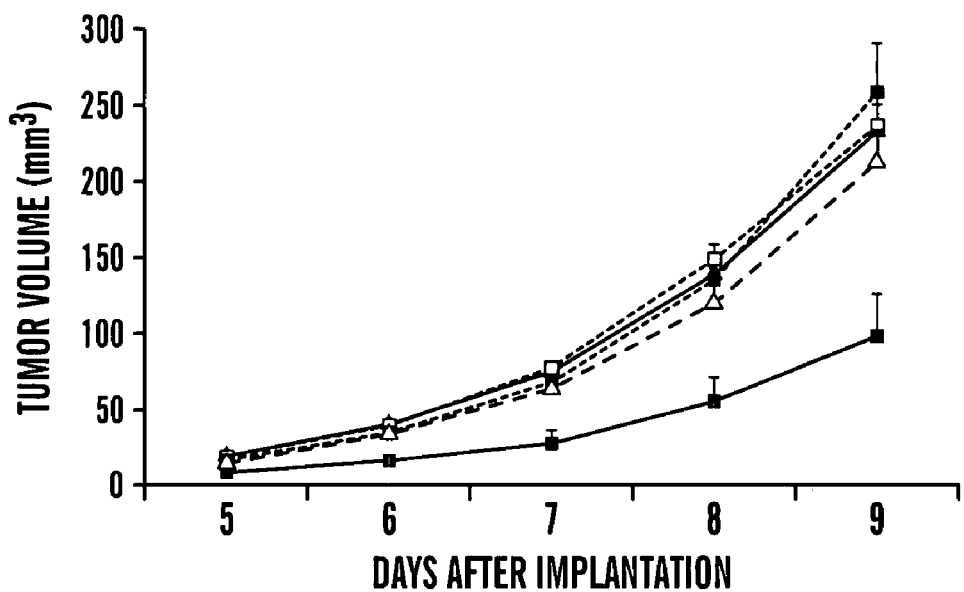
Figure 14G:
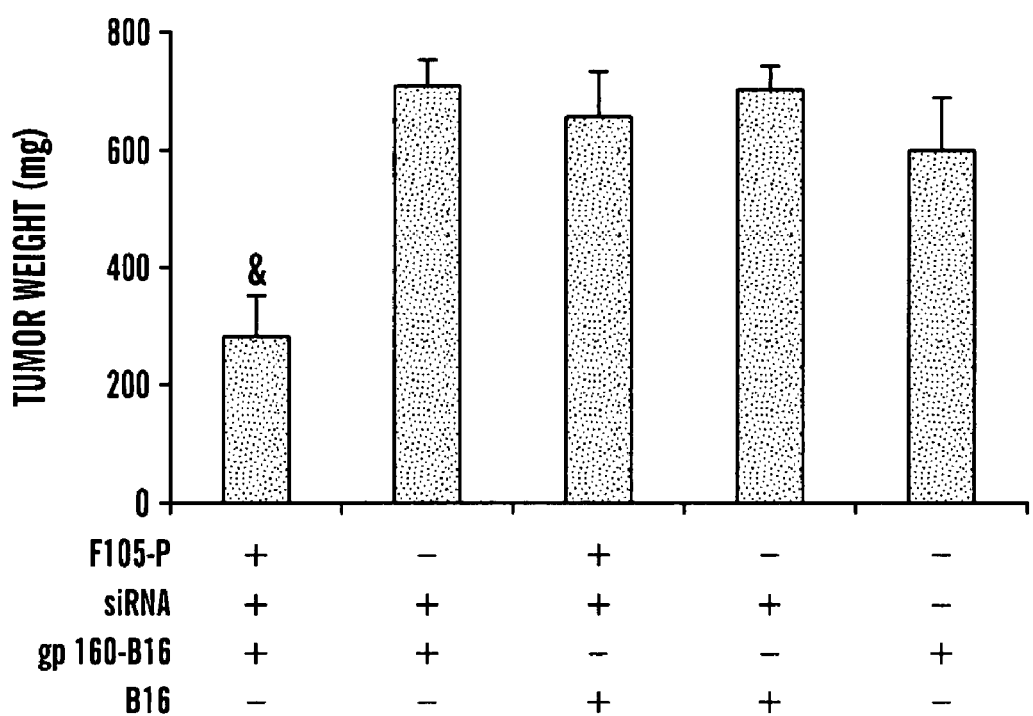

Specific systemic delivery of fluorescent siRNAs The next step was to determine whether F105-P could specifically deliver siRNA into gp160-B16 cells in vivo. Therefore, we implanted gp160-B16 cells subcutaneously into the right flanks of syngeneic C57/BL6 mice and evaluated the efficiency of F105-P to deliver fluorescent siRNA. When naked FITC-siRNA was injected into the tumor tissue, the tumor cells did not take up siRNA efficiently. When FITC-siRNA mixed with Oligofectamine was injected, the siRNA was taken up by the tumor and adjacent subcutaneous tissue. In contrast, F105-P specifically deposited FITC-siRNA into gp160+ tumor cells, but not to adjacent tissue (FIG. 14A). On higher magnification, the fluorescent signal was seen staining the cell membrane and diffusely in the cytoplasm, but not in the nucleus, of the tumor cells (FIG. 14B). F105-P delivery was specific since implanted B16 cells not expressing gp160 did not take up FITC-siRNA. Furthermore, about 30% of gp160-B16 cells, but none of the gp160⁻ B16 cells, took up FITC-siRNA when the F105-P-siRNA mixture was injected intravenously in a small (100 μl) volume (FIG. 14C). No FITC-siRNA was taken up by the tumor following intravenous injection without F105-P.

Delivered siRNAs inhibit melanoma growth in vivo To evaluate the therapeutic potential of antibody-mediated siRNA delivery, we injected F105-P complexed with a mixture of siRNAs against c-myc, MDM2 and VEGF either directly into the tumor or intravenously on days 0, 1 and 3 after implanting 5×10⁶ B16 or gp160-B16 tumor cells subcutaneously into the flank of groups of 8 mice. Tumor size was measured beginning on day 5 when the tumors became palpable, and the tumors were weighed when mice were sacrificed on day 9 (FIG. 14D-14G). The gp160-B16 tumors were significantly smaller in mice treated with intratumoral or intravenous injection of F105-P-siRNA complexes as compared to those treated with siRNAs alone. Mice treated with just F105-P had similar size tumors as mice treated with PBS. Intratumoral injection was somewhat more effective than systemic delivery. As expected, growth of B16 tumors lacking gp160 expression was unaffected by F105-P-siRNA treatment and neither B16 nor gp160-B16 tumors were reduced by injection of naked siRNAs. Therefore, F105-P was able to deliver siRNAs specifically to env-expressing tumor cells to suppress tumor growth even when administered systemically.

Figure 15A:
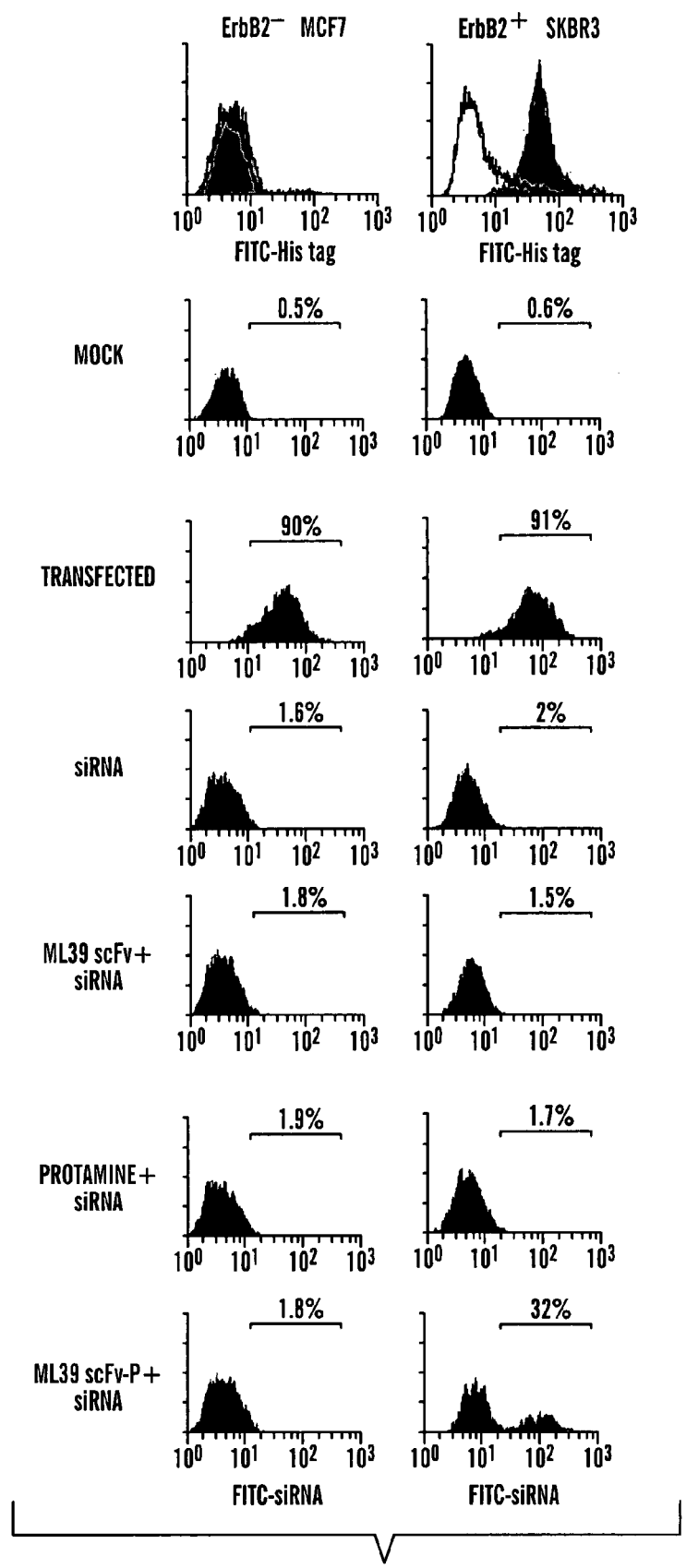
FIGS. 15A-15C show a single chain antibody fragment against ErbB2 fused to a protamine fragment specifically and effectively delivers siRNAs only to ErbB2+ breast cancer cells.
Figure 15B:
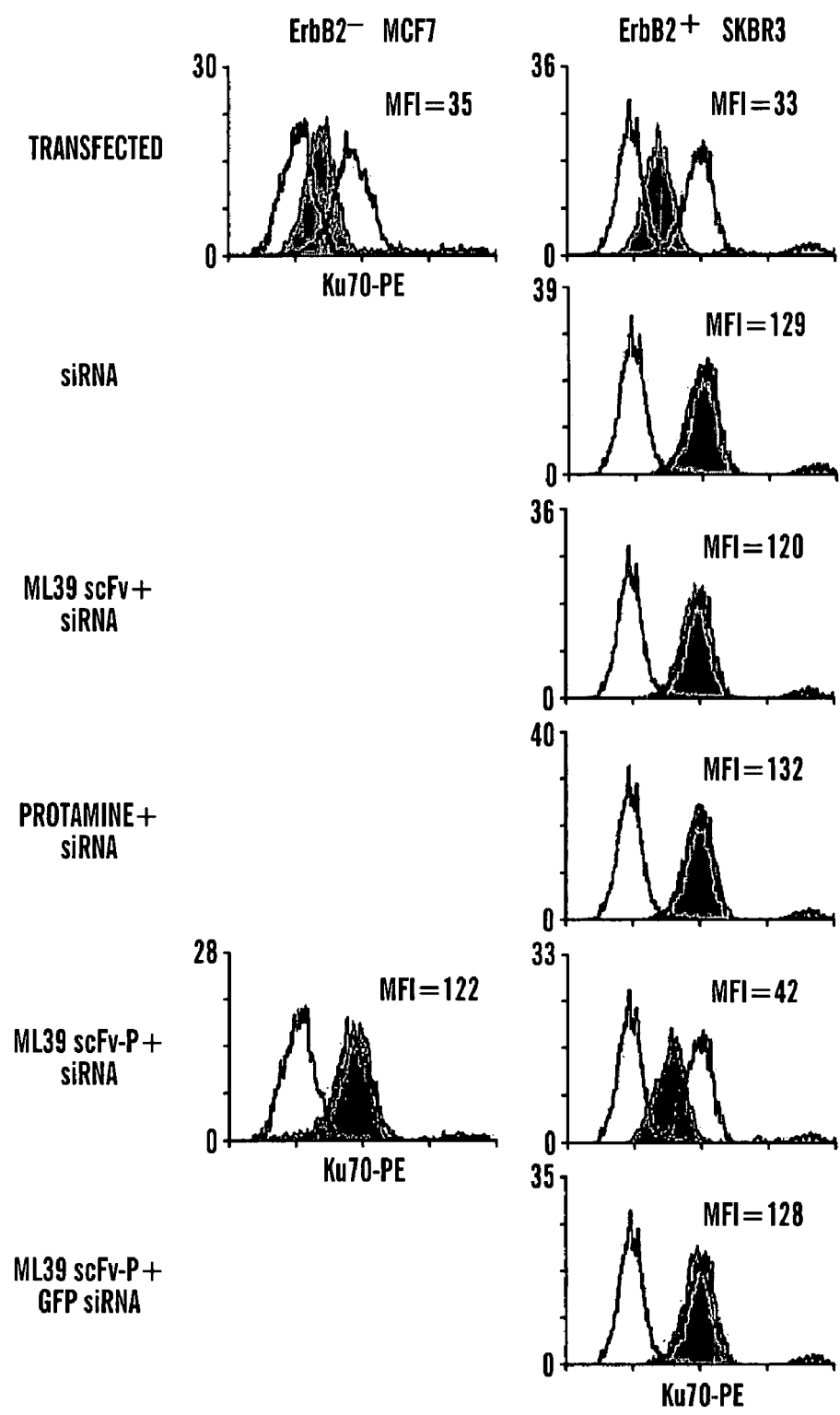
Figure 15C:
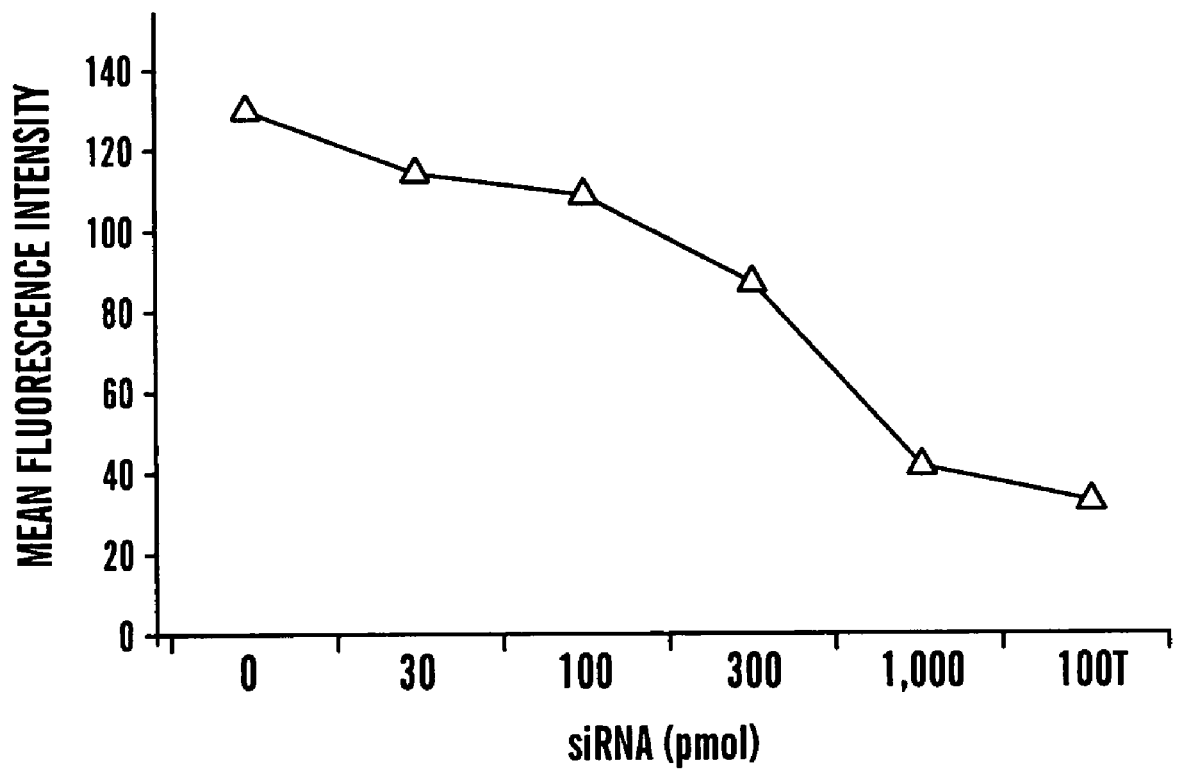

Delivery by single chain antibody fused to protamine To determine whether antibody-mediated delivery of siRNAs could be used to target other cell surface molecules besides gp120, we expressed from baculovirus a fusion protein composed of a single chain antibody fragment (ML39 ScVf) that recognizes the receptor ErbB2, expressed on many breast cancer cells, fused at its C terminus to a fragment of protamine corresponding to amino acids 8-29 (ML39 ScVf-P)[10]. ML39 ScVf-P has previously been shown to introduce plasmid DNA only into ErbB2+ cells[10]. Because the fusion protein was retained within insect cells, it was extracted in guanidine HCl and refolded by gradual renaturation. Nonetheless, the yield of the single chain antibody fusion protein from infected insect cells was much greater than the yield of F105-P expressed in mammalian cells. ML39 ScVf binds to ErbB2+ SKBR3 cells but not to ErbB2− MCF7 breast cancer cell lines (FIG. 15A). We first compared the ability of ML39 ScVf-P to introduce FITC-siRNA into SKBR3 versus MCF7 cells (FIG. 15A). ML39 ScVf-P delivered FITC-siRNA into 32% of ErbB2-expressing cells, but did not transduce ErbB2− cells above background. There was no delivery without a carrier protein or by using the single chain unmodified antibody or protamine alone. Because delivery was specific, we next looked at silencing of Ku70 by ML39 ScVf-P delivered siRNA (FIGS. 15B, 15C). Silencing of Ku70 occurred only in ErbB2+ SKBR3 cells, not in MCF7 cells, and required the fusion protein and Ku70 siRNA since protamine or ML39 ScFv mixed with Ku70 siRNA or ML39 ScVf-P mixed with irrelevant EGFP siRNA had no effect on Ku70 expression. The dose response for silencing by ML39 ScVf-P plateaued at approximately 1000 pmol of siRNA, about 3-10 fold more than is necessary for effective silencing with either transfection or F105-P delivery. Further work is needed to determine whether this could be improved by using full-length protamine (51 amino acids) fused to the single chain antibody or optimizing the renaturation conditions or the binding ratio for siRNA.

Discussion

We used HIV envelope protein as a model receptor for targeted delivery of siRNAs via an antibody Fab fragment fused to protamine. Delivery was specific to env-bearing cells both in vitro and in vivo and systemic delivery was possible by conventional intravenous administration. It was even possible to introduce siRNAs into hard-to-transfect primary CD4 T cells and to suppress HIV production in already infected cells. Targeted delivery of siRNAs should raise the therapeutic index for siRNAs, reduce the amount of drug required and minimize concerns about off-target effects.

The promising data in this proof of principle study lay the foundation for further improvements. As we showed for ErbB2, the fusion protein can be modified by replacing the Fab fragment with a single chain antibody. The antibody could also be replaced by a cell surface receptor ligand. In principle, full-length protamine or nucleic acid-binding protamine fragments or other nucleic acid-binding peptides could be fused to the targeting moiety at either the N or C termini of the antibody or ligand. Other expression systems could also be used to produce the fusion protein. We presented preliminary evidence that the antibody fusion protein delivered siRNA does not induce interferon[2] or activate other nonspecific inflammatory responses[4] when administered in vitro. However, this needs to be studied more carefully and verified in vivo. However, we did not observe any obvious toxicity or inflammatory infiltrate in our in vivo tumor model.

Pharmacokinetics of fusion antibody-delivered siRNAs remain to be determined. However, the fusion protein-complexed siRNAs will likely have a favorable half-life compared to unmodified siRNAs. Filtration of naked siRNAs by the kidney is the rate-limiting factor responsible for the short in vivo half-life of unmodified siRNAs. The estimated size of the complex (1 molecule of $V_H C_{H1}$ (233 aa)-protamine (51 aa), 30 kDa; 1 molecule of $V_\kappa C_\kappa$, 28 kDa; 6 molecules of siRNA, 6×7000 Da) is 100 kDa, well above the cut-off for kidney filtration. The fusion protein-siRNA complex is not likely to form particles that would be trapped in reticuloendothelial cells, such as tissue macrophages and dendritic cells, in filtering organs like the lung and spleen and interfere with systemic delivery. In fact no fluorescent siRNA uptake was noted in these organs (data not shown). Unmodified siRNAs have an in vitro serum half-life of ~1 hr due to endogenous RNase activity[11]. Binding to the fusion protein may protect complexed siRNAs from plasma RNases, but this needs to be determined. Chemical modification of the siRNA in the complex should reduce vulnerability to serum degradation, but whether modifications would enhance in vivo efficacy is uncertain, since chemical modifications appear to come at the price of efficiency for intracellular silencing[12].

Our delivery strategy targeted antiviral siRNAs specifically into cells actively replicating HIV-1. Since siRNA transport required gp160 expression, viral production was suppressed only in cells actively transcribing viral genes. Whether this would provide a feasible or optimal method for using siRNAs as small molecule antiretroviral drugs to target infected cells is hard to predict. More efficient silencing might be achieved using another shared cell surface receptor on the principal types of HIV-infected cells (CD4 T cells and macrophages), such as the HIV coreceptors CCR5 or CXCR4. Since our targeting strategy is flexible, the HIV env antibody component of the fusion protein could be replaced by a specific antibody to a chemokine receptor or by the receptor ligand, such as a chemokine or chemokine analog. This would target cells at an earlier stage to prevent infection. However, specific delivery to already infected cells could be used to silence essential genes required for cell survival to eliminate infected cells without harming normal cells. Because siRNAs do not need to be covalently coupled to the antibody-fusion protein, the same reagent can be flexibly used to deliver changing mixtures of different siRNAs. Targeting multiple viral and/or host genes using cocktails of siRNAs could likely improve suppression of HIV infection over what we achieved by just targeting HIV gag[13].

In this study we used an artificial system to target melanoma cells by transfecting them to express HIV env. This delivery strategy could be modified to target any of a variety of cells via different types of cell surface receptors. Specific tumor markers, often indicators of a poorly differentiated state or of lineage commitment, have been identified for many human tumor cells. Examples include c-erbB2 (Her2) on some breast cancer cells[14], the EBV-encoded LMP proteins on nasopharyngeal carcinoma, or surface immunoglobulin on B cell lymphomas. However, there is some likelihood that tumors might be able to down-modulate expression of any particular cell surface receptor to escape from therapy. A judicious choice of receptor to target (such as the receptor for a growth factor required for tumor proliferation, i.e. IL-6R on myeloma cells or IL-2R on T cell lymphoma cells) might reduce the chance of escape. Normal cells whose function needs to be regulated could also be targeted by this method. Examples might be T lymphocytes in autoimmune disease, dendritic cells or macrophages during inflammatory diseases or hepatocytes for hypercholesterolemia. The latter have been recently targeted in vivo by systemic administration of a chemically modified siRNA covalently linked to a cell receptor ligand (cholesterol binding to the apoB receptor)[12].

The trafficking pathway of F 105-P-delivered siRNAs into the cytoplasm remains to be understood. The most likely pathway following cell surface receptor binding is clathrin-mediated endocytosis. The efficiency of silencing compared to transfection suggests that if siRNAs are endocytosed, they are stable in the harsh endosomal milieu. How the siRNAs would exit from endosomes to the cytoplasm is unclear, but imaging (FIG. 15C) and silencing clearly show trafficking to the cytosol. A cell biology study to follow the delivery of fluorescent siRNAs is needed.

Overcoming the delivery obstacle is the greatest barrier for using siRNAs as small molecule drugs for most indications (reviewed in [1]). Although local delivery is possible via lipid-based methods, particularly at mucosal surfaces such as the skin or lung,[15-17] (and as demonstrated here using Oligofectamine for intratumoral delivery), systemic delivery is more challenging. The hydrodynamic injection method used in the first studies of in vivo protection from disease by siRNAs[6,18,19] is not practical for human use. For some indications, local injection into the vein draining an organ may provide an alternate approach that could be used in humans[20,21]. Approaches that have been reported to work in vivo include complexes with the polymer atelocollagen[22], polyethyleneimine containing nanoparticles, lipid complexes, and liposomes[23-25] and covalent linkage to cholesterol to target the liver[12]. However, these methods are not cell-type specific. Silencing using antibody-mediated delivery is highly efficient, requiring about 15-fold less siRNA than was needed for cholesterol conjugated siRNA silencing in vivo[10]. Because our method does not involve covalent linkage of siRNAs or specialized chemistry, it has the advantage of flexibility, allowing easy preparation and evaluation of varying siRNA mixtures with the same delivery reagent. The method can be readily adapted to target almost any cell type. Moreover the method is readily accessible for in vivo testing by academic laboratories. Immunoliposomes that have been reported to deliver siRNA-encoding plasmids to glioma cells might also be adapted for cell-specific targeting of siRNAs[26]. The method that works best in vivo may need to be tailor-made for the target cell and disease indication. Direct comparisons of different delivery approaches will be required to choose amongst possible strategies as they become available. However, this study and the recent report of Soutschek et al.[12] suggest that the delivery obstacle can be overcome.

It is evident that those skilled in the art, given the benefit of the foregoing disclosure may make numerous modifications thereof, and departures from the specific embodiments described herein, without departing from the inventive concepts, and the present invention is to be limited solely by the scope and spirit of the appended claims.

We claim:

1. A method of selectively delivering a siRNA into a target cell in a subject, the method comprising
administering systemically to said subject a fusion protein-double stranded RNA complex, the complex comprising:
a) a RNA molecule comprising a double stranded RNA segment of about 15-50 base pairs in length, wherein one of one strands is complementary and the other strand identical to a RNA interference target RNA; and
b) a fusion protein, comprising (1) an antibody that binds specifically to an antigen on the surface of a target cell, and (2) a protamine protein, or fragment thereof, capable of binding to double stranded RNA without chemical conjugation;
wherein the fusion protein-double stranded RNA complex selectively binds to the antigen on the surface of the target cell and selectively initiates RNA interference in the cell.

2. The method of delivering a siRNA of claim 1, wherein the antibody is an antibody to a viral envelope protein, a cellular receptor, or an extracellular domain of an activated receptor.

3. The method of delivering a siRNA of claim 1, wherein the antibody is a single chain antibody, a Fab portion of an antibody or a (Fab')$_2$ segment.

4. The method of claim 3, wherein the antibody recognizes gp120 or gp160.

5. The method of claim 1, wherein the-protamine protein, or portion thereof, is fused to the carboxyl portion of the antibody.

6. The method of claim 1, wherein the siRNA targets mRNA encoding c-myc, VEGF, CD4, CCR5, gag, MDM2, Apex, Ku70, or ErbB2.

7. The method of claim 1, wherein the cell is selected from the group consisting of hepatocytes, myocytes, neural cells, lipocytes, lymphocytes, macrophages, cardiac cells, endothelial cells, and epithelial cells.

8. The method of claim 1, wherein the target cell is a malignant cell.

9. The method of claim 8, wherein the malignant cell is selected from the group consisting of a lung cancer cell, a retinal cancer cell, a breast cancer cell, a ovarian cancer cell, a prostate cancer cell, a head and neck cancer cell, a lymphoma cell, a melanoma cell, a glioma cell, a bladder cancer cell, a genital-urinary cancer cell, a stomach cancer cell, a pancreatic cancer cell, a liver cancer cell, a kidney cancer cell, and a gastrointestinal cancer cell.

10. The method of claim 1, wherein the subject is human.

11. The method of claim 1, further comprising administering at least one additional fusion protein-double stranded RNA complex that interferes with an additional RNA interference target RNA within the same target cell.

12. A method of selectively delivering a siRNA into a target cell in a subject, the method comprising
administering systemically to said subject at least a first and a second fusion protein-double stranded RNA complex, each first and second complex comprising:
(a) a RNA molecule comprising a double stranded RNA segment of about 15-50 base pairs in length, wherein one of one strands is complementary and the other strand identical to a RNA interference target RNA; and
(b) a fusion protein, comprising (1) an antibody that binds specifically to an antigen on the target cell surface and (2) a protamine protein, or fragment thereof, capable of binding to double stranded RNA without chemical conjugation;
wherein the fusion protein-double stranded RNA complex binds to an antigen site on said target cell surface and selectively initiates RNA interference against at least a first and second target RNA within the same target cell.

13. A method of delivering a siRNA into a target primary cell, the method comprising contacting the target primary cell with a fusion protein-double stranded RNA complex comprising:
(a) a RNA molecule comprising a double stranded RNA segment, wherein one of the strands is complementary and the other strand identical to a RNA interference target RNA; and
(b) a recombinant protein comprising (1) an antibody that binds specifically to an antigen on the target primary cell surface, and (2) a protamine protein, or fragment thereof, capable of binding to double stranded RNA without chemical conjugation;
wherein said recombinant protein-double stranded RNA complex binds specifically to an antigen on the target primary cell; and
wherein said recombinant protein-double stranded RNA complex selectively initiates RNA interference within the target primary cell.

14. A method of delivering a siRNA into a target primary cell, the method comprising contacting the target primary cell with a fusion protein-double stranded RNA complex comprising:
(a) a RNA molecule comprising a double stranded RNA segment of about 15-50 base pairs in length, wherein one of the strands is complementary and the other strand identical to a RNA interference target RNA; and
(b) a fusion protein comprising (1) an antibody that binds specifically to an antigen on the target primary cell surface, and (2) a protamine protein, or fragment thereof, capable of binding to double stranded RNA without chemical conjugation;
wherein the double stranded RNA segment binds the fusion protein without chemical conjugation and wherein said fusion protein-double stranded RNA complex binds specifically to an antigen on the target primary cell; and
wherein said fusion protein-double stranded RNA complex selectively initiates RNA interference within the target primary cell.

15. A method of selectively delivering a siRNA into a target cell in a subject, the method comprising
administering systemically to said subject a fusion protein-double stranded RNA complex, the complex comprising:
a) a RNA molecule comprising a double stranded RNA segment of about 15-50 base pairs in length, wherein one of one strands is complementary and the other strand identical to a RNA interference target RNA; and
b) a fusion protein, comprising (1) an antibody that binds specifically to an antigen on the surface of a target cell, and (2) a full-length protamine protein, or fragment thereof, capable of binding to double stranded RNA without chemical conjugation, wherein the fragment thereof is encoded by a nucleic acid having a sequence selected from the group consisting of: SEQ ID NO:1, SEQ ID NO:2; SEQ ID NO:3, SEQ ID NO:4, SEQ ID NO:6, and nucleic acids 10-76 of SEQ ID NO:1; and
wherein the fusion protein-double stranded RNA complex selectively binds to the antigen on the surface of the target cell and selectively initiates RNA interference in the cell.

* * * * *